United States Patent
Takata et al.

(10) Patent No.: US 10,726,295 B2
(45) Date of Patent: Jul. 28, 2020

(54) CONTROL METHOD AND RECORDING MEDIUM

(71) Applicant: Panasonic Intellectual Property Management Co., Ltd., Osaka (JP)

(72) Inventors: Kazutoyo Takata, Fukui (JP); Kenji Kondo, Fukui (JP); Kazuki Kozuka, Osaka (JP); Hirohiko Kimura, Fukui (JP); Toyohiko Sakai, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 894 days.

(21) Appl. No.: 15/272,277

(22) Filed: Sep. 21, 2016

(65) Prior Publication Data

US 2017/0091582 A1    Mar. 30, 2017

(30) Foreign Application Priority Data

Sep. 30, 2015  (JP) .................................. 2015-193682

(51) Int. Cl.
  *G06F 16/30*    (2019.01)
  *G06K 9/62*    (2006.01)
  (Continued)

(52) U.S. Cl.
  CPC ............ *G06K 9/6212* (2013.01); *A61B 5/055* (2013.01); *A61B 6/5217* (2013.01);
  (Continued)

(58) Field of Classification Search
  CPC .............................. G06K 9/6212; G06F 16/30
  (Continued)

(56) References Cited

U.S. PATENT DOCUMENTS

| 7,155,043 B2 * | 12/2006 | Daw ...................... G01R 33/56 |
| | | 382/128 |
| 2011/0237938 A1 * | 9/2011 | Mizuno ................. G06T 7/0012 |
| | | 600/425 |

(Continued)

FOREIGN PATENT DOCUMENTS

JP    2009-045121    3/2009

OTHER PUBLICATIONS

Extended European Search Report dated Feb. 21, 2017 in corresponding European Application No. 16189902.6.

*Primary Examiner* — Irete F Ehichioya
*Assistant Examiner* — Johnese T Johnson
(74) *Attorney, Agent, or Firm* — Wenderoth, Lind & Ponack, L.L.P.

(57) ABSTRACT

A control method includes: receiving, from a case search system, a plurality of data including a plurality of images corresponding to a plurality of similar medical images having a certain similarity with a target medical image to be interpreted; displaying on a display a display screen including a first display area that displays thumbnails of the plurality of similar medical images; sensing one similar medical image selected from among the plurality of similar medical images displayed as thumbnails in the first display area; if the one selected similar medical image is a diffuse lesion, displaying the other plurality of medical images in a second display area included on the display screen; and if the one selected similar medical image is a localized lesion, successively displaying, in the second display area and in a first direction, the plurality of medical images including the localized lesion.

3 Claims, 56 Drawing Sheets

(51) Int. Cl.
  *G16H 40/63*   (2018.01)
  *G16H 50/70*   (2018.01)
  *G16H 30/40*   (2018.01)
  *A61B 5/055*   (2006.01)
  *A61B 6/00*    (2006.01)
  *G06F 19/00*   (2018.01)
  *G06F 3/0482*  (2013.01)

(52) U.S. Cl.
  CPC ........... *G06F 19/321* (2013.01); *G16H 30/40* (2018.01); *G16H 40/63* (2018.01); *G16H 50/70* (2018.01); *G06F 3/0482* (2013.01); *G06K 2009/6213* (2013.01); *G06K 2209/051* (2013.01)

(58) Field of Classification Search
  USPC ........................................................ 707/705
  See application file for complete search history.

(56) References Cited

U.S. PATENT DOCUMENTS

2014/0350395 A1* 11/2014 Shachaf ................ G06T 7/0012
                                                      600/431
2015/0173684 A1   6/2015 Takata et al.

\* cited by examiner

FIG. 8

| DISEASE LIST | 730 | |
|---|---|---|
| MYCOSIS | 14 | 731 |
| ASPERGILLOSIS | 8 | 732 |
| CRYPTOCOCCOSIS | 6 | 733 |
| NEOPLASTIC | 13 | 734 |
| LUNG CANCER | 10 | 735 |
| METASTATIC LUNG CANCER | 3 | 736 |
| NON-NEOPLASTIC | 6 | 737 |
| LUNG ABSCESS | 4 | 738 |
| SARCOIDOSIS | 1 | 739 |
| SEPTIC EMBOLI | 1 | 740 |
| MYCOBACTERIOSIS | 6 | 741 |
| NTM | 4 | 742 |
| TUBERCULOSIS | 2 | 743 |
| OTHER | 2 | 744 |
| BRONCHIECTASIS | 1 | 745 |
| ... | 1 | |

FIG. 14

LESION DISTRIBUTION  /750

☑ DIFFUSE /751   ☐ MULTIPLE /755

▨ SEGMENTAL /752   ▨ SUBPLEURAL /756

☐ BRONCHIAL /753   ☑ HEMATOGENOUS /757

☐ BILATERAL /754

| 1100 | PATIENT ID | 123456 |
|---|---|---|
| 1200 | NAME | PANA, TARO |
| 1300 | AGE | 28 |
| 1400 | SEX | MALE |
| 1500 | MEDICAL HISTORY | N/A |
| 1600 | FAMILY HISTORY | N/A |
| 1700 | CHIEF COMPLAINT | COUGHING |
| 1800 | EXAMINATION INFORMATION | (SEE FIG. 17) |
| 1900 | DEFINITE DIAGNOSIS | MYCOPLASMA PNEUMONIA |

FIG. 17

| | 1800 | |
|---|---|---|
| 1810 | EXAMINATION ID | 13227895 |
| 1820 | EXAMINATION DATE | 20XX／2／5 10:00 |
| 1830 | EXAMINATION TYPE | BLOOD TEST |
| 1840 | EXAMINATION RESULT | YYYY1 |
| | EXAMINATION ID | 13227903 |
| | EXAMINATION DATE | 20XX／2／5 11:00 |
| | EXAMINATION TYPE | PLAIN X-RAY (CHEST) |
| | EXAMINATION RESULT | YYYY2 |
| | EXAMINATION ID | 13227989 |
| | EXAMINATION DATE | 20XX／2／9 9:00 |
| | EXAMINATION TYPE | CT (CHEST) |
| | EXAMINATION RESULT | YYYY3 |

⋮

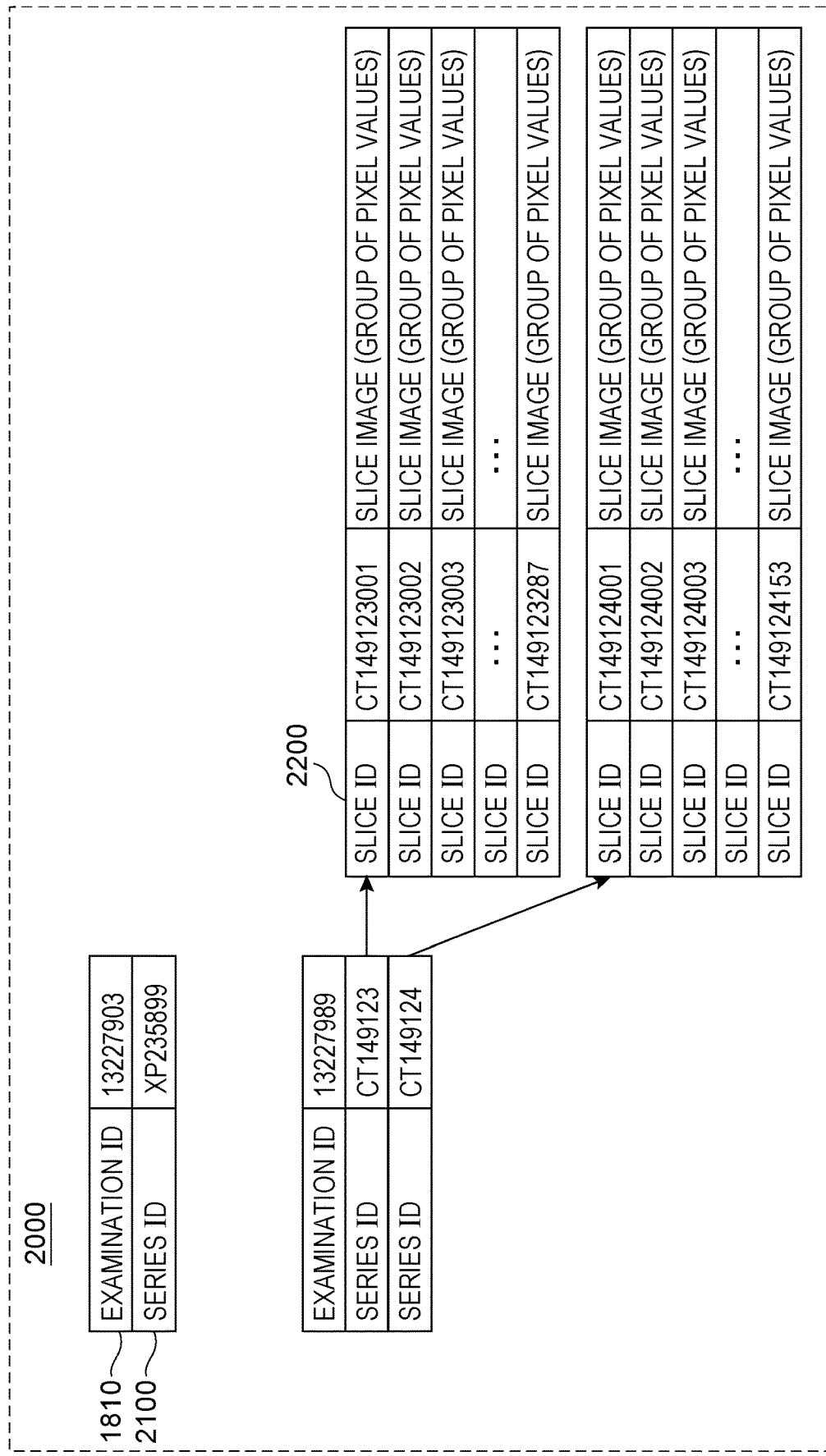

FIG. 19

| 1810 | EXAMINATION ID | 132277989 |
| 3100 | OBSERVATIONS | MULTIPLE NODULES FROM 0.5 cm TO 1 cm IN SIZE IN RIGHT LUNG FIELD... |
| 3200 | DIAGNOSIS | INFLAMMATORY NODULES OR TUBERCULOSIS SUSPECTED. |

| 4000 | |
|---|---|
| 4100 SIMILAR CASE ID | SIM5232 |
| 4200 SLICE ID | CT149391025 |
| 4300 ROI INFORMATION | $x_t, y_t, x_r, y_b$ |
| 4400 IMAGE FEATURE DATA | $f_1, f_2, f_3, ..., f_N$ |
| 4500 THUMBNAIL IMAGE DATA | $I_{0,0}, I_{0,1}, ..., I_{0,0}, ..., I_{w-1,h-1}$ |
| 4600 LESION DISTRIBUTION INFORMATION | |
| 4700 DEFINITE DIAGNOSIS (MAJOR DISEASE CLASSIFICATION) | PNEUMONIA |
| 4800 DEFINITE DIAGNOSIS (FINE DISEASE CLASSIFICATION) | BACTERIAL PNEUMONIA |
| 4900 LESION ATTRIBUTE | DIFFUSE |
| 4910 SUMMARY IMAGES | CT149391007<br>CT149391025<br>CT149391043 |

| DIFFUSE | SEGMENTAL | BRONCHIAL | BILATERAL | MULTIPLE | SUBPLEURAL | HEMATOGENOUS |
|---|---|---|---|---|---|---|
| 1 | 0 | 0 | 0 | 0 | 0 | 0 |
| 4610 | 4620 | 4630 | 4640 | 4650 | 4660 | 4670 |

FIG. 21A

| 4000 | | |
|---|---|---|
| 4100 | SIMILAR CASE ID | SIM32356 |
| 4200 | SLICE ID | CT149391025 |
| 4300 | ROI INFORMATION | $x_l, y_t, x_r, y_b$ |
| 4400 | IMAGE FEATURE DATA | $f_1, f_2, f_3, ..., f_N$ |
| 4500 | THUMBNAIL IMAGE DATA | $I_{0,0}, I_{0,1}, I_{0,0}, ..., I_{w-1,h-1}$ |
| 4600 | LESION DISTRIBUTION INFORMATION | |
| 4700 | DEFINITE DIAGNOSIS (MAJOR DISEASE CLASSIFICATION) | NEOPLASTIC |
| 4800 | DEFINITE DIAGNOSIS (FINE DISEASE CLASSIFICATION) | LUNG CANCER |
| 4900 | LESION ATTRIBUTE | LOCALIZED |
| 4910 | SUMMARY IMAGES | CT149391023<br>CT149391024<br>CT149391025<br>CT149391026<br>CT149391027 |

| | |
|---|---|
| DIFFUSE | 0 | (4610)
| SEGMENTAL | 0 | (4620)
| BRONCHIAL | 0 | (4630)
| BILATERAL | 0 | (4640)
| MULTIPLE | 0 | (4650)
| SUBPLEURAL | 0 | (4660)
| HEMATOGENOUS | 1 | (4670)

FIG. 21B

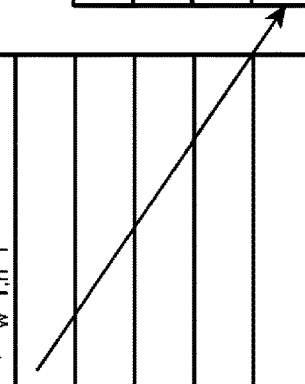

| | | |
|---|---|---|
| 4100 | SIMILAR CASE ID | SIM32356 |
| 4200 | SLICE ID | CT149391025 |
| 4300 | ROI INFORMATION | $x_l, y_t, x_r, y_b$ |
| 4400 | IMAGE FEATURE DATA | $f_1, f_2, f_3, ..., f_N$ |
| 4500 | THUMBNAIL IMAGE DATA | $I_{0,0}, I_{0,1}, ..., I_{0,0}, ..., I_{w-1,h-1}$ |
| 4600 | LESION DISTRIBUTION INFORMATION | |
| 4700 | DEFINITE DIAGNOSIS (MAJOR DISEASE CLASSIFICATION) | NEOPLASTIC |
| 4800 | DEFINITE DIAGNOSIS (FINE DISEASE CLASSIFICATION) | LUNG CANCER |
| 4900 | LESION ATTRIBUTE | LOCALIZED |
| 4940 | REGION | MIDDLE LOBE |

| | |
|---|---|
| 4610 DIFFUSE | 0 |
| 4620 SEGMENTAL | 0 |
| 4630 BRONCHIAL | 0 |
| 4640 BILATERAL | 0 |
| 4650 MULTIPLE | 0 |
| 4660 SUBPLEURAL | 0 |
| 4670 HEMATOGENOUS | 1 |

FIG. 24

| PATIENT ID | PATIENT NAME | EXAMINATION DATE | EXAMINATION ID | EXAMINATION TYPE |
|---|---|---|---|---|
| 443982 | YAMADA, ICHIRO | 20XX/12/1 | 23982874 | MR (HEAD) |
| 123456 | PANA, TARO | 20XX/5/8 | 13227989 | CT (CHEST) |
| 345455 | ... | ... | ... | ... |
| 235982 | ... | ... | ... | ... |

800

| SERIES ID | DEFINITION | IMAGE |
|---|---|---|
|  |  |  |
|  |  |  |
|  |  |  |

| PATIENT ID | PATIENT NAME | EXAMINATION DATE | EXAMINATION ID | EXAMINATION TYPE |
|---|---|---|---|---|
| 443982 | YAMADA, ICHIRO | 20XX/12/1 | 23982874 | MR (HEAD) |
| 123456 | PANA, TARO | 20XX/5/8 | 13227989 | CT (CHEST) |
| 345455 | ... | ... | ... | ... |
| 235982 | ... | ... | ... | ... |

800

| SERIES ID | DEFINITION | IMAGE |
|---|---|---|
| CT152729 | LUNG FIELD CONDITION SLICE THICKNESS: 5 mm | |
| CT152730 | LUNG FIELD CONDITION SLICE THICKNESS: 1 mm | |
| CT152731 | MEDIASTINUM CONDITION SLICE THICKNESS: 5 mm | |

| DISEASE ID | MAJOR DISEASE CLASSIFICATION | FINE DISEASE CLASSIFICATION | NO. OF CASES | SIMILAR CASE IDs |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NON-NEOPLASTIC | LUNG ABSCESS | 4 | ... |
| ... | MYCOBACTERIOSIS | NTM | 4 | ... |
| ... | ... | ... | ... | |

FIG. 31

DISEASE LIST     730

| | |
|---|---|
| LUNG CANCER | 10 |
| ASPERGILLOSIS | 8 |
| CRYPTOCOCCOSIS | 6 |
| LUNG ABSCESS | 4 |
| NTM | 4 |
| METASTATIC LUNG CANCER | 3 |
| TUBERCULOSIS | 2 |
| INFLAMMATORY NODULES | 1 |
| SEPTIC EMBOLI | 1 |
| BRONCHIECTASIS | 1 |
| UNKNOWN | 1 |

FIG. 32

DISEASE LIST     730

| | |
|---|---|
| MYCOSIS | 14 |
| NEOPLASTIC | 13 |
| NON-NEOPLASTIC | 6 |
| MYCOBACTERIOSIS | 6 |
| OTHER | 2 |

FIG. 33

| DISEASE LIST | 730 |
|---|---|
| MYCOSIS | 14 |
|   ASPERGILLOSIS | 8 |
|   CRYPTOCOCCOSIS | 6 |
| NEOPLASTIC | 13 |
|   LUNG CANCER | 10 |
|   METASTATIC LUNG CANCER | 3 |
| NON-NEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NTM | 4 |
|   TUBERCULOSIS | 2 |
| OTHER | 2 |
|   BRONCHIECTASIS | 1 |
|   ... | 1 |

FIG. 35

| DISTRIBUTION NAME | NO. OF CASES | SIMILAR CASE IDs |
|---|---|---|
| DIFFUSE | 3 | SIM2521, SIM4123, SIM5225 |
| SEGMENTAL | 0 | N/A |
| BRONCHIAL | 2 | SIM0006, SIM1892, SIM4399 |
| BILATERAL | 12 | ... |
| MULTIPLE | 22 | ... |
| SUBPLEURAL | 0 | N/A |
| HEMATOGENOUS | 5 | ... |

| USER ID | NUMBER OF COLUMNS | NUMBER OF ROWS | POSITION OF CASE TO BE DIAGNOSED |
|---|---|---|---|
| U01 | 2 | 2 | (1,1) |
| U02 | 3 | 2 | (2,1) |
| U03 | 3 | 3 | (2,2) |
| ... | ... | ... | ... |

FIG. 37

| 4410 | |
|---|---|
| NUMBER OF ROWS | 2 |
| NUMBER OF COLUMNS | 2 |

4411

| POSITION | SLICE ID |
|---|---|
| ROW 1 COLUMN 1 | CT12353515 |
| ROW 1 COLUMN 2 | — |
| ROW 2 COLUMN 1 | — |
| ROW 2 COLUMN 2 | — |

| | 4000 | |
|---|---|---|
| 4100 | SIMILAR CASE ID | SIM5232 |
| 4200 | SLICE ID | CT149391025 |
| 4300 | ROI INFORMATION | $x_l, y_t, x_r, y_b$ |
| 4400 | IMAGE FEATURE DATA | $f_1, f_2, f_3, ..., f_N$ |
| 4500 | THUMBNAIL IMAGE DATA | $I_{0,0}, I_{0,1}, I_{0,0}, ..., I_{w-1,h-1}$ |
| 4600 | LESION DISTRIBUTION INFORMATION | |
| 4700 | DEFINITE DIAGNOSIS (MAJOR DISEASE CLASSIFICATION) | PNEUMONIA |
| 4800 | DEFINITE DIAGNOSIS (FINE DISEASE CLASSIFICATION) | BACTERIAL PNEUMONIA |
| 4930 | PLEURAL REGION INFORMATION | $xp_l, yp_t, xp_r, yp_b$ |
| 4900 | LESION ATTRIBUTE | DIFFUSE |
| 4910 | SUMMARY IMAGES | CT149391007<br>CT149391025<br>CT149391043 |

| | | |
|---|---|---|
| 4610 | DIFFUSE | 1 |
| 4620 | SEGMENTAL | 0 |
| 4630 | BRONCHIAL | 0 |
| 4640 | BILATERAL | 0 |
| 4650 | MULTIPLE | 0 |
| 4660 | SUBPLEURAL | 0 |
| 4670 | HEMATOGENOUS | 0 |

FIG. 55

| 4000 | | |
|---|---|---|
| 4100 | SIMILAR CASE ID | SIM32356 |
| 4200 | SLICE ID | CT149391025 |
| 4300 | ROI INFORMATION | $x_l, y_t, x_r, y_b$ |
| 4400 | IMAGE FEATURE DATA | $f_1, f_2, f_3, ..., f_N$ |
| 4500 | THUMBNAIL IMAGE DATA | $I_{0,0}, I_{0,1}, I_{0,0}, ..., I_{w-1,h-1}$ |
| 4600 | LESION DISTRIBUTION INFORMATION | |
| 4700 | DEFINITE DIAGNOSIS (MAJOR DISEASE CLASSIFICATION) | PNEUMONIA |
| 4800 | DEFINITE DIAGNOSIS (FINE DISEASE CLASSIFICATION) | BACTERIAL PNEUMONIA |
| 4900 | LESION ATTRIBUTE | DIFFUSE |
| 4920 | INTRA-ORGAN REGIONS | UPPER LOBE: CT149391000–CT149391020 |
| | | MIDDLE LOBE: CT149391021–CT149391031 |
| | | LOWER LOBE: CT149391032–CT149391055 |

| | |
|---|---|
| DIFFUSE | 1 — 4610 |
| SEGMENTAL | 0 — 4620 |
| BRONCHIAL | 0 — 4630 |
| BILATERAL | 0 — 4640 |
| MULTIPLE | 0 — 4650 |
| SUBPLEURAL | 0 — 4660 |
| HEMATOGENOUS | 0 — 4670 |

FIG. 56

| | | | |
|---|---|---|---|
| 4100 | SIMILAR CASE ID | SIM32356 | |
| 4200 | SLICE ID | CT149391025 | |
| 4300 | ROI INFORMATION | $x_l, y_t, x_r, y_b$ | |
| 4400 | IMAGE FEATURE DATA | $f_1, f_2, f_3, ..., f_N$ | |
| 4500 | THUMBNAIL IMAGE DATA | $I_{0,0}, I_{0,1}, I_{0,0}, ..., I_{w-1,h-1}$ | |
| 4600 | LESION DISTRIBUTION INFORMATION | | |
| 4700 | DEFINITE DIAGNOSIS (MAJOR DISEASE CLASSIFICATION) | NEOPLASTIC | |
| 4800 | DEFINITE DIAGNOSIS (FINE DISEASE CLASSIFICATION) | LUNG CANCER | |
| 4900 | LESION ATTRIBUTE | LOCALIZED | |
| 4920 | INTRA-ORGAN REGIONS | UPPER LOBE | CT149391000–CT149391020 |
| | | MIDDLE LOBE | CT149391021–CT149391031 |
| | | LOWER LOBE | CT149391032–CT149391055 |

4000

| | |
|---|---|
| DIFFUSE | 0 | 4610
| SEGMENTAL | 0 | 4620
| BRONCHIAL | 0 | 4630
| BILATERAL | 0 | 4640
| MULTIPLE | 0 | 4650
| SUBPLEURAL | 0 | 4660
| HEMATOGENOUS | 1 | 4670

CONTROL METHOD AND RECORDING MEDIUM

BACKGROUND

1. Technical Field

The present disclosure relates to a control method for an information terminal and a recording medium for searching similar medical images resembling a medical image to be interpreted.

2. Description of the Related Art

Recently, medical imaging devices, such as computed tomography (CT) and magnetic resonance imaging (MRI), for example, are developing and proliferating. These technologies such as CT and MRI enable the acquisition of large amounts of digitized high-definition medical images. Additionally, medical images interpreted by physicians are being stored successively, together with interpretation reports, in picture archiving and communication systems (PACS). At this point, as disclosed in Japanese Unexamined Patent Application Publication No. 2009-45121, for example, technologies are started to be developed in which past cases already stored in a PACS may be searched to find and use past medical images resembling a new medical image to be interpreted as a reference when interpreting the new medical image.

SUMMARY

One non-limiting and exemplary embodiment provides further improvements.

In one general aspect, the techniques disclosed here feature a control method for an information terminal, including a display, that connects to a case search system that searches for medical images by referencing a medical image database in which medical images are registered, the control method being executed by a computer of the information terminal, and including: receiving, from the case search system, a plurality of data including a plurality of images corresponding to a plurality of similar medical images having a certain similarity with a target medical image to be interpreted, wherein each of the plurality of medical images is one medical image captured by tomography and part of a group of images arranged in a first direction, identification information of a diffuse lesion or a localized lesion is set in correspondence information corresponding to each of the plurality of data, the correspondence information in which identification information of a diffuse lesion is set additionally includes another plurality of medical images among the group of images arranged in the first direction, and the correspondence information in which identification information of a localized lesion is set additionally includes a plurality of medical images including the localized lesion from among the group of images arranged in the first direction; displaying on the display a display screen including a first display area that displays thumbnails of the plurality of similar medical images; sensing one similar medical image selected from among the plurality of similar medical images displayed as thumbnails in the first display area; if the one selected similar medical image is a diffuse lesion, displaying the other plurality of medical images in a second display area included on the display screen; and if the one selected similar medical image is a localized lesion, successively displaying, in the second display area and in the first direction, the plurality of medical images including the localized lesion.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is an enlarged view of a disease list display area;

FIG. 14 is a diagram illustrating a distribution list display area into which multiple checkmarks have been input;

FIG. 16 is a diagram illustrating a data structure of patient information;

FIG. 17 is a diagram illustrating a data structure of examination information registered in the patient information illustrated in FIG. 16;

FIG. 18B is a diagram illustrating a data structure of a medical image database;

FIG. 19 is a diagram illustrating a data structure of a diagnosis report;

FIG. 20 is a diagram illustrating a first example of a data structure of diffuse similar case data;

FIG. 21A is a diagram illustrating a first example of a data structure of localized similar case data;

FIG. 21B is a diagram illustrating a second example of a data structure of localized similar case data;

FIG. 24 is a diagram illustrating an examination list screen;

FIG. 25 is a diagram illustrating an examination list screen after an examination is selected;

FIG. 30 is a diagram illustrating a data structure of a disease list generated in S1300 of FIG. 28;

FIG. 31 is a diagram illustrating a first display example of a disease list display area;

FIG. 32 is a diagram illustrating a second display example of a disease list display area;

FIG. 33 is a diagram illustrating a third display example of a disease list display area;

FIG. 35 is a diagram illustrating a data structure of a distribution list generated in S1400 of FIG. 28;

FIG. 36 is a diagram illustrating an example of layout management information;

FIG. 37 is a diagram illustrating a data structure of display box management information;

FIG. 48 is a diagram illustrating a data structure of similar case data with added pleural region information;

FIG. 55 is a diagram illustrating a second example of a data structure of diffuse similar case data;

FIG. 56 is a diagram illustrating a third example of a data structure of localized similar case data.

Figure 1:
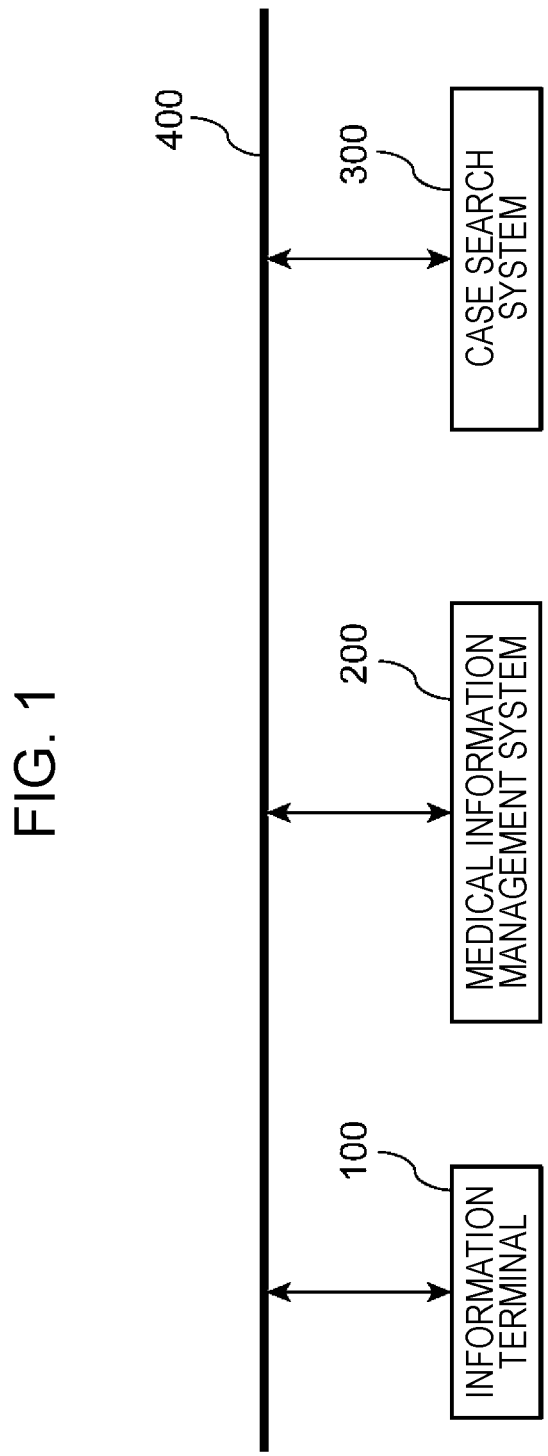
FIG. 1 is an overall configuration diagram of a hospital information system to which an information terminal according to the present embodiment has been applied.

DETAILED DESCRIPTION (Findings that LED to the Invention of an Aspect According to the Present Disclosure)

First, a focus of an aspect according to the present disclosure will be described.

Japanese Unexamined Patent Application Publication No. 2009-45121 discloses a medical image processing system that presents an image to be interpreted and case images in a format allowing easy comparison by a radiological interpreter. The medical image processing system generates a variation image in which image features of a case image are varied (see paragraphs [0053] to [0054] and FIG. 7), and displays the generated variation image in a similar case image window 920 (see paragraph [0062] and FIG. 9). In addition, when a video display button 970 displayed in the similar case image window 920 is designated, the medical image processing system displays multiple variation images successively in the similar case image window 920.

However, in Japanese Unexamined Patent Application Publication No. 2009-45121, changing the display mode in the similar case image window 920 depending on the types of lesions in the case images is not described in any way. Thus, Japanese Unexamined Patent Application Publication No. 2009-45121 does not even disclose changing the display mode depending on the types of lesions in the case images, and therefore does not disclose innovations such as changing to different display modes for localized lesions and diffuse lesions, for example.

When examining a lesion appearing in a medical image to be interpreted for which a disease has not been identified yet, it is considered effective to refer to similar medical images that resemble the medical image to be interpreted from among other medical images for which a disease has been identified already. However, when constructing such a system, a very large number of medical images are registered in the medical image database. Even in such cases, it is desirable to present similar medical images to the physician effectively as a reference for diagnosing the medical image to be interpreted.

Through consideration of the above issues, the inventors conceived the following aspects of the present disclosure.

A first aspect of the present disclosure is a control method for an information terminal, including a display, that connects to a case search system that searches for medical images by referencing a medical image database in which medical images are registered, the control method being executed by a computer of the information terminal, and including:

receiving, from the case search system, a plurality of data including a plurality of images corresponding to a plurality of similar medical images having a certain similarity with a target medical image to be interpreted, wherein each of the plurality of medical images is one medical image captured by tomography and part of a group of images arranged in a first direction, identification information of a diffuse lesion or a localized lesion is set in correspondence information corresponding to each of the plurality of data, the correspondence information in which identification information of a diffuse lesion is set additionally includes another plurality of medical images among the group of images arranged in the first direction, and the correspondence information in which identification information of a localized lesion is set additionally includes a plurality of medical images including the localized lesion from among the group of images arranged in the first direction;

displaying on the display a display screen including a first display area that displays thumbnails of the plurality of similar medical images;

sensing one similar medical image selected from among the plurality of similar medical images displayed as thumbnails in the first display area;

if the one selected similar medical image is a diffuse lesion, displaying the other plurality of medical images in a second display area included on the display screen; and if the one selected similar medical image is a localized lesion, successively displaying, in the second display area and in the first direction, the plurality of medical images including the localized lesion.

According to this aspect, multiple similar medical images having a certain similarity to a target medical image are received from a case search system, and the multiple received similar medical images are displayed on a display. Consequently, from among a very large number of medical images registered in a medical image database, similar medical images that serve as a reference for determining the disease causing a lesion appearing in the target medical image are extracted effectively and presented to the physician.

Herein, lesion distribution patterns include the two types of diffuse lesions and localized lesions. Diffuse lesions are distributed over a wide range of the entire organ. On the other hand, localized lesions are distributed in a localized area.

For diffuse lesions, the way in which the affected area spreads is extremely important information when identifying the disease. For example, in the case of a medical image of the lungs, whether the affected area is spreading to the upper lobe, the middle lobe, or the lower lobe is important for identifying the disease. For this reason, in the similar case search system, when displaying a similar medical image of diffuse lesions, it is desirable to be able to determine the extent of the spread of the affected area at a glance. One display mode enabling the extent of the spread of the affected to be determined at a glance is a display mode that displays multiple medical images from among a group of medical images captured by tomography.

On the other hand, for localized lesions, whether or not the affected area exists along the direction of blood vessels is extremely important information when identifying the disease. For this reason, in the similar case search system, when displaying a similar medical image of localized lesions, it is desirable to be able to check whether or not the affected area exists along the direction of blood vessels. Additionally, for localized lesions, it is desirable to be able to check the three-dimensional shape of the affected area. A display mode enabling one to check the three-dimensional shape in which the affected area may or may not exist along the direction of blood vessels is a display mode that successively displays multiple medical images including localized lesions from among a group of medical images captured by tomography, or in other words, displays a video.

According to this aspect, if one similar medical image selected from among multiple similar medical images displayed as thumbnails in a first display area is a diffuse lesion, multiple other medical images from among a group of images captured by tomography and arranged in a first direction are displayed in a second display area. Also, if the one selected similar medical image is a localized lesion, multiple medical images including localized lesions from among a group of images captured by tomography and arranged in the first direction are displayed successively in the first direction in the second display area. Consequently, similar medical images depicting information relevant to identifying a disease may be presented to the physician effectively and efficiently.

The above aspect may also be configured so that if the one selected similar medical image is a localized lesion, a plurality of medical images including from one end to another end of the localized lesion among the group of images arranged in the first direction are displayed successively in the second display area and in the first direction.

According to this aspect, multiple medical images from one end to another end of a localized lesion are displayed successively in a first direction. For this reason, the physician is able to check the three-dimensional shape in which a localized lesion has spread from one end to the other end along the direction of blood vessels, and the accuracy of diagnosis may be improved.

The above aspect may also be configured so that if the one selected similar medical image is a localized lesion, a certain number of adjacent medical images, including the one selected similar medical image, among the group of images arranged in the first direction are displayed successively in the second display area and in the first direction.

According to this aspect, a certain number of adjacent medical images including one similar medical image selected from among a group of images arranged in a first direction are displayed successively in the first direction. If a certain number of medical images adjacent to the one selected similar medical image are displayed, it is possible to adequately check the three-dimensional shape in which a localized lesion has spread along the direction of blood vessels. In addition, it is not necessary to set medical images including the localized lesion in advance, and the burden of creating metadata about similar medical images is reduced.

The above aspect may also be configured so that the similar medical image is a medical image of lungs, the correspondence information in which identification information of a localized lesion is set additionally includes information indicating a lung field from among an upper lobe, a middle lobe, and a lower lobe in which the localized lesion exists, and the certain number of adjacent medical images including the one selected similar medical image is set respectively for each of the upper lobe, the middle lobe, and the lower lobe.

Since localized lesions rarely straddle the lung fields, it is sufficient to display medical images successively in each lung field where a localized lesion exists. In this aspect, medical images in the lung field including the one selected similar medical image are displayed successively. For this reason, this aspect is able to decrease the viewing time of medical images displayed successively, and present medical images to the user more efficiently.

The above aspect may also be configured so that
the similar medical image is a medical image of lungs,
the correspondence information in which identification information of a diffuse lesion is set additionally includes information indicating a representative medical image for each of an upper lobe, a middle lobe, and a lower lobe, and
if the one selected similar medical image is a diffuse lesion, the representative images of the upper lobe, the middle lobe, and the lower lobe are displayed in the second display area.

When ascertaining a lesion of the lungs overall, the upper lobe, the middle lobe, and the lower lobe are the smallest units. Since diffuse lesions spread throughout the entire lung, it is sufficient to view a representative medical image of each lung field. In this aspect, if the one selected similar medical image is a diffuse lesion, representative medical images of the upper lobe, the middle lobe, and the lower lobe from among a group of images arranged in the first direction are displayed in the second display area. Consequently, medical images may be presented more efficiently.

The above aspect may also be configured so that
the control method causes a computer of the information terminal to execute a process including:
sensing specifying information indicating a region of interest in the medical image to be interpreted;
transmitting features of the region of interest to the case search system; and
receiving, from the case search system, similar medical images having the certain similarity with the features of the region of interest.

The above aspect may also be configured so that
the control method causes a computer of the information terminal to execute a process including:
sensing specifying information indicating a region of interest in the target medical image;
transmitting the target medical image and the specifying information to the case search system; and
receiving, from the case search system, similar medical images having the certain similarity with features of the region of interest obtained from the target medical image and the specifying information.

The above aspect may also be configured so that
the target medical image is a medical image of lungs,
each of the similar medical images includes a corresponding region of interest indicating an affected area in the similar medical image,
the display screen includes
first distribution information enabling selection of similar medical images in which a size of the corresponding region of interest belongs to a certain first range indicating a wide range of a lung region,
second distribution information enabling selection of similar medical images in which the size of the corresponding region of interest belongs to a certain second range, lower than the first range, indicating a part of a lung region, and
third distribution information enabling selection of similar medical images in which the corresponding region of interest includes pleura, and
if a selection of any one from the first distribution information to the third distribution information is sensed, similar medical images corresponding to the one selected distribution information are selected are displayed in the first display area.

According to this aspect, multiple similar medical images displayed in the first display area additionally may be sorted based on the distribution pattern of the corresponding region of interest. Consequently, for example, similar medical images for which the distribution of the affected area resembles the target medical image may be selected efficiently from among a large number of displayed similar medical images.

The above aspect may also be configured so that
the first display area includes a plurality of individual areas for respectively displaying each of the received plurality of similar medical images,
if a selection of the first distribution information is sensed, similar medical images corresponding to the first distribution information are displayed respectively in each of the individual areas, at an initial display size,
if a selection of the second distribution information is sensed, similar medical images corresponding to the second distribution information are displayed respectively in each of the individual areas, zoomed in and centered on the corresponding region of interest in each of the similar medical images corresponding to the second distribution information, and
if a selection of the third distribution information is sensed, similar medical images corresponding to the third distribution information are displayed respectively in each of the individual areas, zoomed in and centered on the corresponding region of interest in each of the similar medical images corresponding to the third distribution information, and in a state including the pleura.

According to this aspect, when sorting similar medical images based on the distribution pattern of the corresponding region of interest, a display is presented according to not only simple sorting, but also the distribution pattern. Consequently, the physician is not required to sort similar medical images based on the distribution pattern of the corresponding region of interest, and then perform other processes separately, such as zooming the similar medical images according to the distribution pattern or centering the similar medical images on the corresponding region of interest. For this reason, even after images are sorted based on the distribution pattern of the corresponding region of interest, the subsequent burdensome work of repeatedly performing similar operations on the large number of sorted similar medical images one by one may be reduced greatly. As a result, lapses in the physician's thinking or concentration, which should be directed at making a medical diagnosis, due to the burden of such operations may be decreased greatly, and the physician's thinking and concentration may be directed towards the original task of making a medical diagnosis. For this reason, it is possible to improve the accuracy of medical diagnosis.

The above aspect may also be configured so that
the first distribution information is information indicating a distribution belonging to a bilateral, a multiple, a diffuse, or a hematogenous category,
the second distribution information is information indicating a distribution belonging to a segmental or a bronchial category, and the third distribution information is information indicating a distribution belonging to a subpleural category.

According to this aspect, in the case of a distribution belonging to the bilateral, multiple, diffuse, or hematogenous categories, similar medical images are displayed at the initial display size, whereas in the case of a distribution belonging to the segmental or bronchial categories, similar medical images are displayed zoomed, and in the case of a distribution belonging to the subpleural category, similar medical images are displayed zoomed in a state of including the pleura.

In the case of a distribution belonging to the bilateral, multiple, diffuse, or hematogenous categories, there is a high probability that the affected area has spread throughout the lungs or over a wide range of the lungs, and thus, from the medical standpoint, there is a need to display similar medical images at the initial display size, or in other words, without zooming. On the other hand, in the case of a distribution belonging to the segmental or bronchial categories, the probability of the above is low. For this reason, by displaying similar medical images zoomed as a result of selecting a distribution belonging to the segmental or bronchial categories, the step of zooming the display may be skipped, thereby avoiding a lapse in the physician's concentration. Also, in the case of a distribution belonging to the subpleural category, the positional relationship between the pleura and the affected area becomes an important indicator for diagnosis, and thus, from the medical standpoint, there is a need to display similar medical images zoomed in a state of including the pleura.

Another aspect of the present disclosure is a control method for an information terminal, the control method being executed by a computer of the information terminal, and including:

receiving medical case data items for medical cases, the medical case data items including thumbnail images corresponding to medical images for the medical cases, the medical images being determined based on a target medical image to be interpreted;

displaying a display screen including the thumbnail images on a display;

detecting a selected thumbnail image from among the thumbnail images; and displaying a first thumbnail image, a second thumbnail image, and a third thumbnail image in a first way or a second way, wherein the medical case data items, the medical cases, the thumbnail images, and the medical images are in one-to-one relationship, the thumbnail images include the first thumbnail image, the second thumbnail image, and the third thumbnail image, each of the medical case data items includes first information indicating a corresponding medical image, second information indicating whether the corresponding medical case is diffuse or localized, and third information indicating first medical images for the medical case, the corresponding medical image and the first medical images are obtained through one medical examination performed on a subject, the corresponding medical image and the first medical images include a first image in a first tomographic plane of the subject, a second image in a second tomographic plane of the subject, and a third image in a third tomographic plane of the subject, the first tomographic plane is closest to a top of a head of the subject among the first tomographic plane, the second tomographic plane, and the third tomographic plane, the third tomographic plane is farthest away from the top among the first tomographic plane, the second tomographic plane, and the third tomographic plane, the first thumbnail image corresponds to the first image, the second thumbnail image corresponds to the second image, and the third thumbnail image corresponds to the third image, if the second information corresponding to the selected thumbnail image indicates that the medical case corresponding to the selected thumbnail image is diffuse, the first thumbnail image, the second thumbnail image, and the third thumbnail image are displayed in the first way, if the second information corresponding to the selected thumbnail image indicates that the medical case corresponding to the selected thumbnail image is localized, the first thumbnail image, the second thumbnail image, and the third thumbnail image are displayed in the second way, the first way is that the first thumbnail image, the second thumbnail image, and the third thumbnail image are displayed at a same time on the display, and the second way is that (i) the second thumbnail image is displayed on the display after the first thumbnail image is displayed on the display and the third thumbnail image is displayed on the display after the second thumbnail image is displayed on the display, and/or (ii) the second thumbnail image is displayed on the display after the third thumbnail image is displayed on the display and the first thumbnail image is displayed on the display after the second thumbnail image is displayed on the display.

(Embodiment)

Hereinafter, an embodiment of the present disclosure will be described with reference to the drawings. Note that in the drawings, like signs are used to denote like structural elements.

FIG. 1 is an overall configuration diagram of a hospital information system to which an information terminal according to the present embodiment has been applied. As illustrated in FIG. 1, the hospital information system is equipped with an information terminal 100, a medical information management system 200, and a case search system 300.

The information terminal 100, the medical information management system 200, and the case search system 300 are communicably interconnected over a network 400.

Note that the medical information management system 200 and the case search system 300 are not necessarily required to be installed in a hospital, and may also be software running on hardware such as a data center, a private cloud server, or a public cloud server outside the hospital. In the case in which the medical information management system 200 and the case search system 300 are installed inside the hospital, a local area network may be adopted as the network 400. For the local network, an IEEE 802.3 series wired LAN, an IEEE 802.11 series wireless LAN, or a network combining both may be adopted. In the case in which the medical information management system 200 and the case search system 300 are realized using a server outside the hospital, the Internet may be adopted as the network 400.

For the information terminal 100, an information terminal such as a personal computer or a tablet is adopted. For the medical information management system 200, a system such as a picture archiving and communication system (PACS) or an electronic health record system is adopted.

Figure 2:
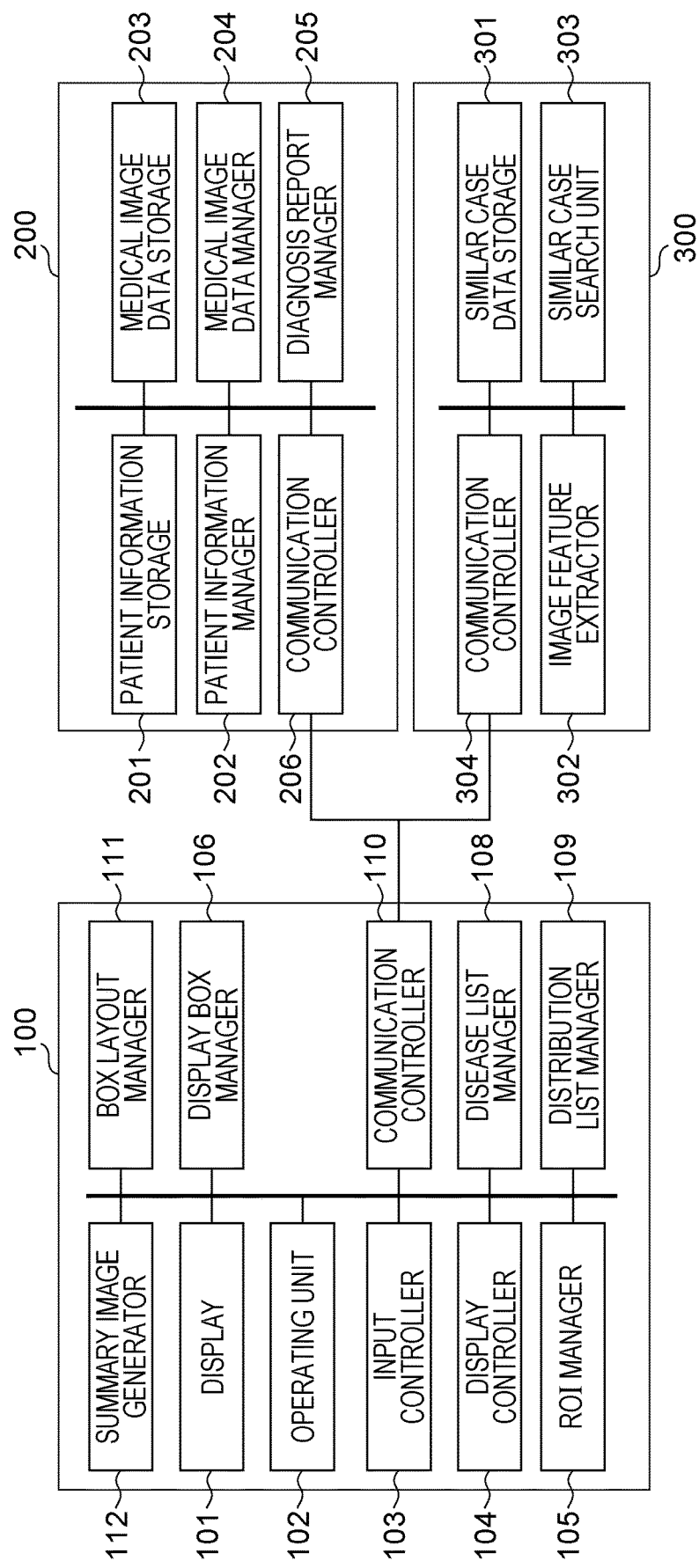
FIG. 2 is a block diagram illustrating a configuration of a medical information management system and a case search system.

FIG. 2 is a block diagram illustrating a configuration of the information terminal 100, the medical information management system 200, and the case search system 300. As illustrated in FIG. 2, the information terminal 100 is equipped with a display 101, an operating unit 102, an input controller 103, a display controller 104, an ROI manager 105, a display box manager 106, a disease list manager 108, a distribution list manager 109, a communication controller 110, a box layout manager 111, and a summary image generator 112.

The display 101 is realized by an LCD monitor, for example, and displays medical images to be diagnosed and health record images, while also displaying information such as a report input image for entering a diagnosis result. Note that although at least one display 101 is required, ordinarily two or three displays 101 are used for image diagnosis. In the present embodiment, two displays 101 are used, in which one display 101 is designated the display 101a, and the other display 101 is designated the display 101b (see FIG. 3).

Figure 3:
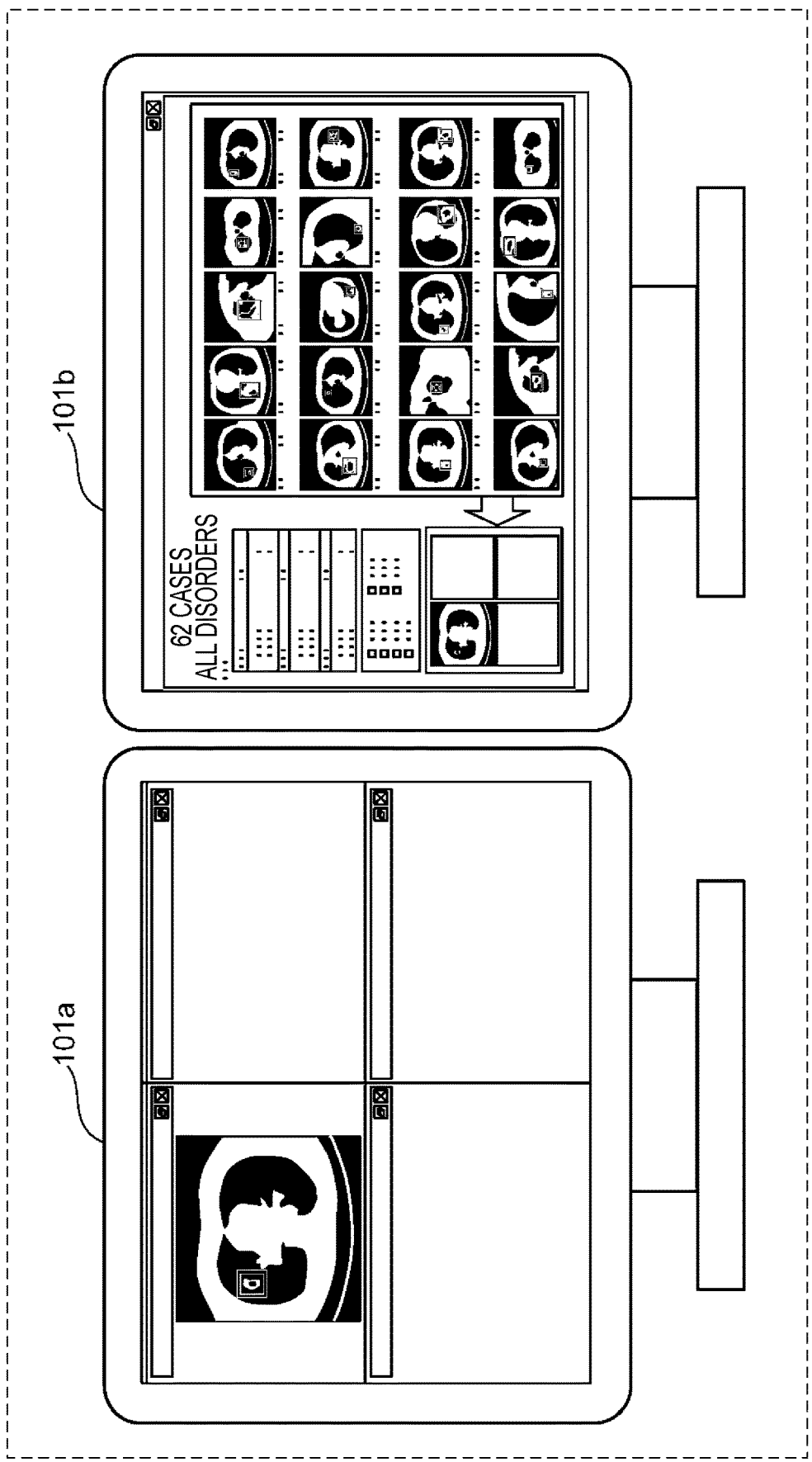
FIG. 3 is an exterior view of two displays.

In addition, the display screen of the display 101a is one example of a second display screen, while the display screen of the display 101 is one example of a first display screen. FIG. 3 is an exterior view of the two displays 101a and 101b. In FIG. 3, on the display 101a, four medical image viewers are displayed in a 2×2 grid arrangement, while on the display 101b, the screen of the case search system 300 is displayed. Note that in the case of using a single display 101, the first display screen and the second display screen are displayed in split areas on the display screen of the single display 101. The operating unit 102 includes a keyboard and a mouse, for example, and accepts various operations input into the information terminal 100 by the user. For example, the operating unit 102 accepts operations such as user operations on medical images and health record images displayed on the display 101, and operations of inputting a diagnosis result into a report input screen.

The input controller 103, after sensing a user operation performed on the operating unit 102, interprets the content of the operation, and notifies other structural elements of the operation content. For example, the input controller 103 senses the position of a mouse pointer on the display 101 from coordinate data output from a mouse being used as the operating unit 102, and causes the mouse pointer to be displayed on the display 101. Additionally, if a GUI element (for example, a GUI button) generated by the display controller 104 is being displayed at the display position of the mouse pointer when the input controller 103 senses that the mouse has been clicked, the input controller 103 determines that the user has selected that GUI element, and notifies other structural elements that the relevant GUI element has been selected by the user.

The display controller 104 generates the graphical user interface (GUI) of the information terminal 100, and displays the GUI on the display 101.

When a similar case search is performed, the ROI manager 105 generates, and stores in memory, region of interest information indicating a region of interest (ROI) set with respect to a search query image discussed later, and manages the region of interest information.

The display box manager 106 stores display box management information 4410 (see FIG. 37) discussed later in memory, and manages the display box management information 4410.

The disease list manager 108 generates, and stores in memory, a disease list (see FIG. 30) of similar cases displayed in a case display area 710 (see FIG. 6), and manages the disease list.

The distribution list manager 109 generates, and stores in memory, a distribution list (see FIG. 35) indicating lesion distributions of similar cases displayed in the case display area 710, and manages the distribution list.

The communication controller 110 includes a communication device for connecting the information terminal 100 to the network 400, for example, and controls communication between the information terminal 100 and the medical information management system 200, and between the information terminal 100 and the case search system 300. Additionally, the communication controller 110 accepts requests for the transmission of various data from other blocks, and transmits the various data to the medical information management system 200 or the case search system 300, while in addition, receives data transmitted from the medical information management system 200 or the case search system 300, and passes the data to relevant blocks.

The box layout manager 111 generates, and stores in memory, layout management information 4200 (see FIG. 36) discussed later, and manages the layout management information 4200.

When the input controller 103 senses an operation of selecting one thumbnail image from among thumbnail images displayed in the case display area 710, the summary image generator 112 references the similar case data 4000 of the selected thumbnail image, and determines whether the selected thumbnail image is a localized lesion or a diffuse lesion. Subsequently, in the case of determining a localized lesion, the summary image generator 112 treats the selected thumbnail image as a summary image of a localized lesion, and generates successive frame images 717 (see FIG. 51). On the other hand, in the case of determining a diffuse lesion, the summary image generator 112 treats the selected thumbnail image as a summary image of a diffuse lesion, and generates representative images 718 (see FIG. 52).

Figure 51:
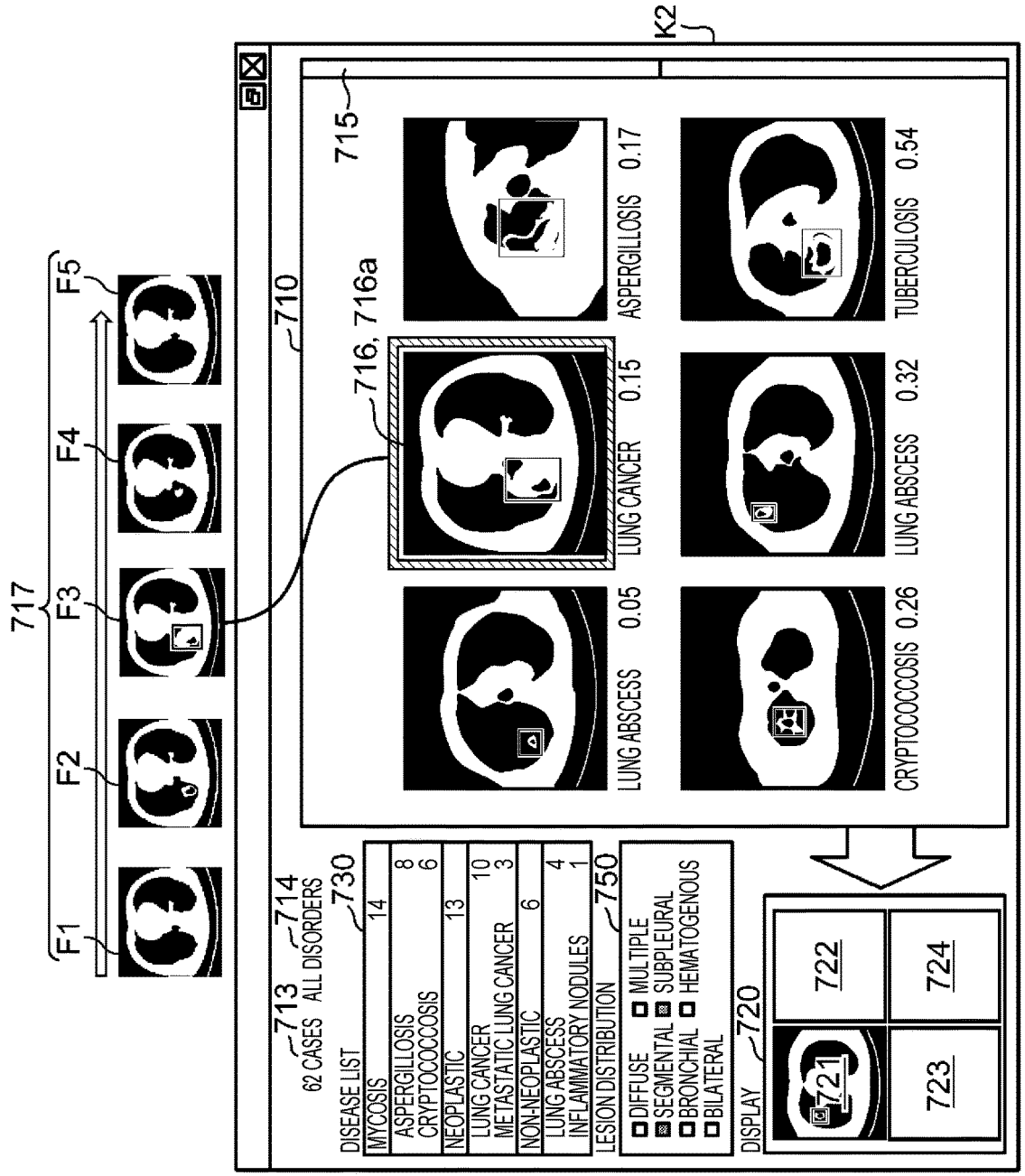
FIG. 51 is a diagram illustrating an example of a basic screen when a thumbnail image selected by a user is a localized lesion.
Figure 52:
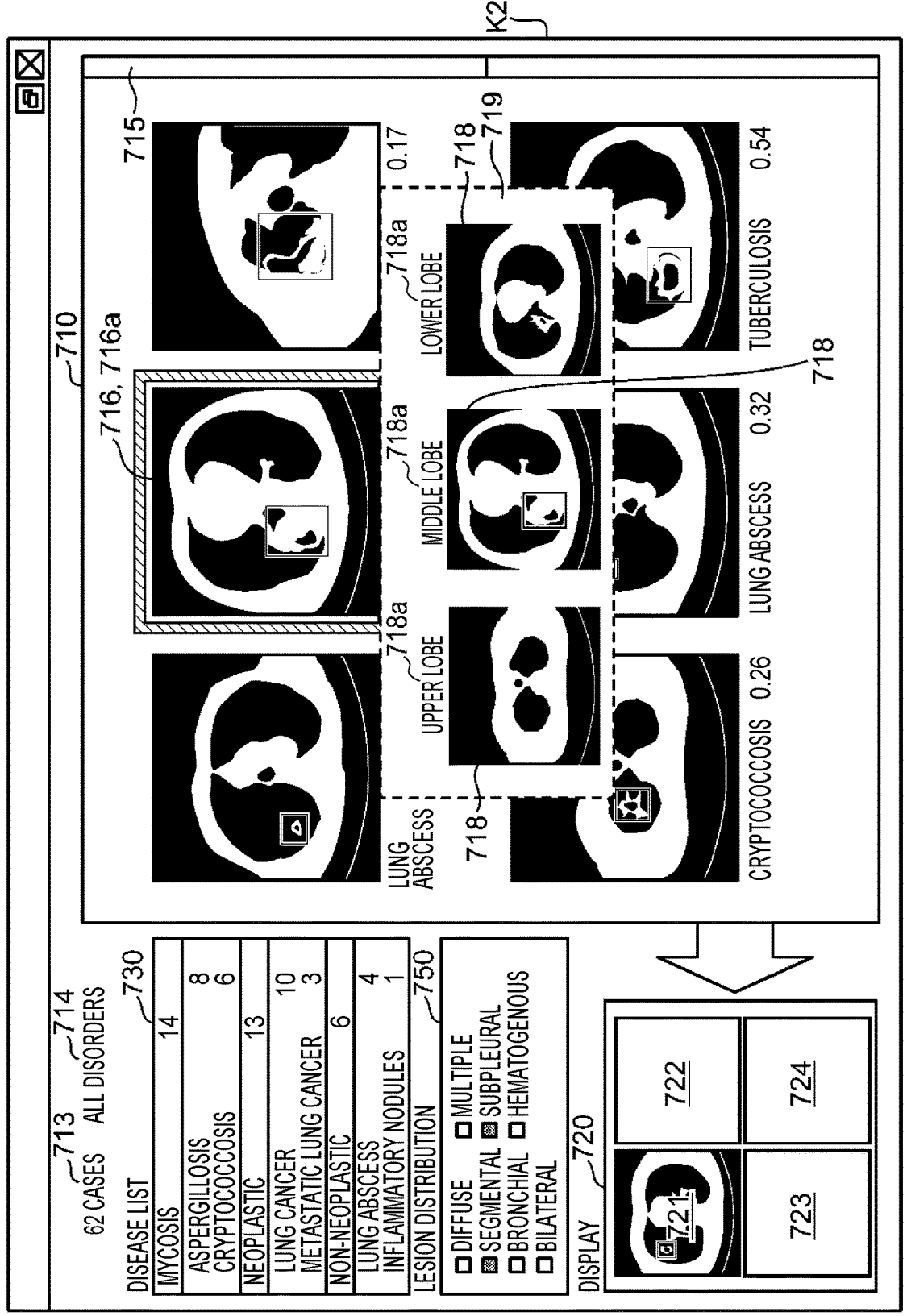
FIG. 52 is a diagram illustrating an example of a basic screen when a thumbnail image selected by a user is a diffuse lesion.

Note that FIGS. 51 and 52 are illustrated using the same similar cases to ease understanding of the differences between the displays.

As illustrated in FIG. 2, the medical information management system 200 is equipped with patient information storage 201, a patient information manager 202, medical image data storage 203, a medical image data manager 204, a diagnosis report manager 205, and a communication controller 206.

The patient information storage 201 stores patient information 1000 (see FIG. 16), in which is registered personal information such as the sex and age of the patient, clinical information such as a medical history, and examination information such as a blood test.

The patient information manager 202 executes processes on the patient information (see FIG. 16) stored in the patient information storage 201, such as a process of registering data input by the user and updating the patient information 1000 and a process of outputting the patient information 1000 to the display controller 104, and manages the patient information 1000. The medical image data storage 203 stores medical image data, which are examination images of patients.

The medical image data manager 204 stores medical image data in the medical image data storage 203, and manages the medical image data.

The diagnosis report manager 205 manages a diagnosis report 3000 (see FIG. 19) indicating a diagnosis result made by a physician for an examination performed on a patient.

The communication controller 206 includes a communication device for connecting the medical information management system 200 to the network 400, for example. The communication controller 206 accepts requests for the transmission of various data from other blocks, and transmits the various data to the information terminal 100 or the case search system 300, while in addition, receives data transmitted from the information terminal 100 or the case search system 300, and passes the data to relevant blocks.

As illustrated in FIG. 2, the case search system 300 is equipped with similar case data storage 301, an image feature extractor 302, a similar case search unit 303, and a communication controller 304.

The similar case data storage 301 stores similar case data 4000 (see FIG. 20, for example), in which is registered in advance image features extracted from a large number of similar cases selected as the target data of a similar case search from among similar cases managed by the medical information management system 200, and generated thumbnail images.

The image feature extractor 302 extracts image features in region of interest information in a search query image transmitted from the communication controller 110 of the information terminal 100. Note that the region of interest information is an example of specifying information indicating a region of interest.

The similar case search unit 303 generates similar case search results by respectively comparing the image features extracted by the image feature extractor 302 to the image features of one or more similar cases stored in the similar case data storage 301.

The communication controller 304 includes a communication device that connects the case search system 300 to the network 400, for example. The communication controller 304 accepts requests for the transmission of various data from other blocks, and transmits the various data to the information terminal 100 or the medical information management system 200, while in addition, receives data transmitted from the information terminal 100 or the medical information management system 200, and passes the data to relevant blocks.

Figure 4:
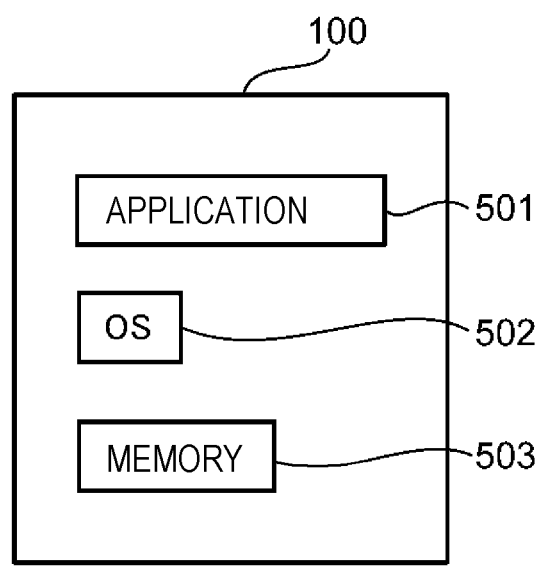
FIG. 4 is a diagram illustrating an example configuration of an implementation of an information terminal.

FIG. 4 is a diagram illustrating an example configuration of an implementation of the information terminal 100. As illustrated in FIG. 4, the information terminal 100 is equipped with an application 501, an operating system (OS) 502, memory 503, and other hardware not illustrated.

The application 501 is application software causing a personal computer or a tablet to function as the information terminal 100, and is executed by a processor of the information terminal 100. The information terminal 100 may implement the application 501 by reading out the application 501 from a computer-readable recording medium, or implement the application 501 by downloading the application 501 from a network.

Herein, the application 501 includes a medical information management application and a similar case search application. The medical information management application is an application for linking the information terminal 100 to the medical information management system 200, while the similar case search application is an application for linking the information terminal 100 to the case search system 300. Additionally, both applications exchange data with each other, and on the information terminal 100, unify the services provided by the medical information management system 200 and the case search system 300.

The OS 502 is the basic software of the information terminal 100, and is executed by a processor of the information terminal 100. The memory 503 is realized by memory devices such as RAM and ROM provided in the information terminal 100, and stores groups of data included in the application 501.

By having a processor of the information terminal 100 execute the application 501, the functions of the input controller 103, the display controller 104, the ROI manager 105, the display box manager 106, the disease list manager 108, the distribution list manager 109, the communication controller 110, and the box layout manager 111 illustrated in FIG. 2 are realized.

However, in the present embodiment, the information terminal 100 may be implemented by the application 501 alone, implemented by the application 501 and the OS 502, implemented by the application 501, the OS 502, and the memory 503, or implemented by the application 501, the OS 502, the memory 503, and other hardware not illustrated. The realization of the information terminal 100 according to the present embodiment is possible with any of the above implementations.

Figure 5:
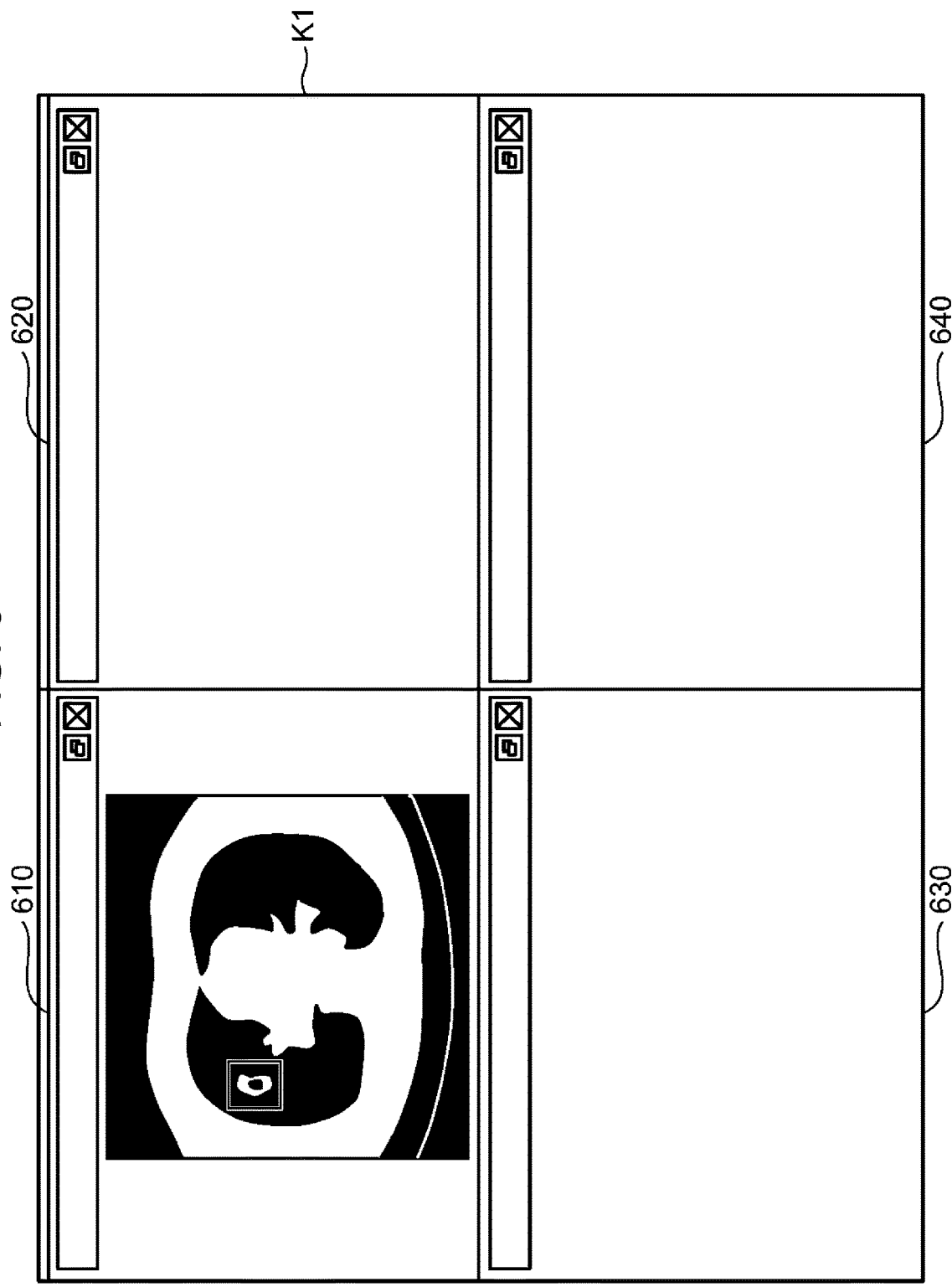
FIG. 5 is a diagram illustrating an example of a basic screen displayed on a display immediately after launching a similar case search application on an information terminal.

FIG. 5 is a diagram illustrating an example of a basic screen K1 displayed on the display 101a immediately after launching the similar case search application on the information terminal 100. The basic screen K1 illustrated in FIG. 5 is made up of four medical image viewers 610 to 640. Ordinarily, medical images are recorded in Digital Imaging and Communication in Medicine (DICOM) format, and the medical image viewers 610 to 640 are viewers that handle DICOM. The medical images handled in the present embodiment are taken to be chest CT images made up of a large number of tomographic images (hereinafter called slice images) in DICOM format. However, this is merely one example, and CT images of other parts (such as the head, abdomen, legs, or arms, for example) may also be adopted.

In the chest CT images displayed on the medical image viewers 610 to 640, slice images may be changed with a mouse or keyboard operation. Herein, the slice images constituting a chest CT image are arranged in order proceeding from the neck to the abdomen.

For example, if the mouse pointer is positioned over the medical image viewer 610, and a rotation of the mouse wheel is sensed by the input controller 103, the display controller 104 changes the slice image being displayed in the medical image viewer 610 according to the sensed amount of rotation. At this point, if the mouse wheel is rotated one click downward, the slice image currently being displayed in the medical image viewer 610 is changed to the slice image in the next slice position, for example. On the other hand, if the mouse wheel is rotated one click upward, the slice image currently being displayed in the medical image viewer 610 is changed to the slice image in the previous slice position, for example. Thus, a user such as a physician searches for a desired slice image while rotating the mouse wheel upward or downward to change the slice image displayed in the medical image viewer 610 as appropriate.

Note that instead of adopting chest CT images as the medical images, magnetic resonance imaging (MRI) images or plain X-ray images may also be adopted. Also, although the number of medical image viewers is 4 in the example of FIG. 5, this is merely one example, and another number such as 6 or 8 may also be adopted. As the number of medical image viewers increases, the number of images that may be compared simultaneously increases, but the display area for each image also becomes smaller. For this reason, a configuration allowing the number of medical image viewers to be modified appropriately according to the display size of the display 101a may be adopted. Herein, the number of medical image viewers is taken to be freely modifiable by a user or an administrator.

Before the similar case search application is launched, a slice image of a chest CT image of a certain patient is displayed over the entirety of the display 101a. Subsequently, in this state, if the similar case search application is launched by a user such as a radiological interpreter, the slice image that was being displayed over the entirety of the display 101a is displayed in the medical image viewer 610.

In other words, when the user launches the similar case search application, the search query image that was being displayed over the entirety of the display 101a is displayed initially in the medical image viewer 610. Note that the display controller 104 may also display the region of interest (ROI) of the target of the similar case search as an overlay on top of the search query image. The search query image is an example of a target medical image, which is a medical image to be interpreted.

In FIG. 5, no images are being displayed in the other medical image viewers 620 to 640, but if there are multiple images from a patient examination to be diagnosed, and the multiple examination images are being displayed on the display 101a before the similar case search application is launched, the display controller 104 may keep displaying these multiple examination images in the medical image viewers 620 to 640.

Figure 6:
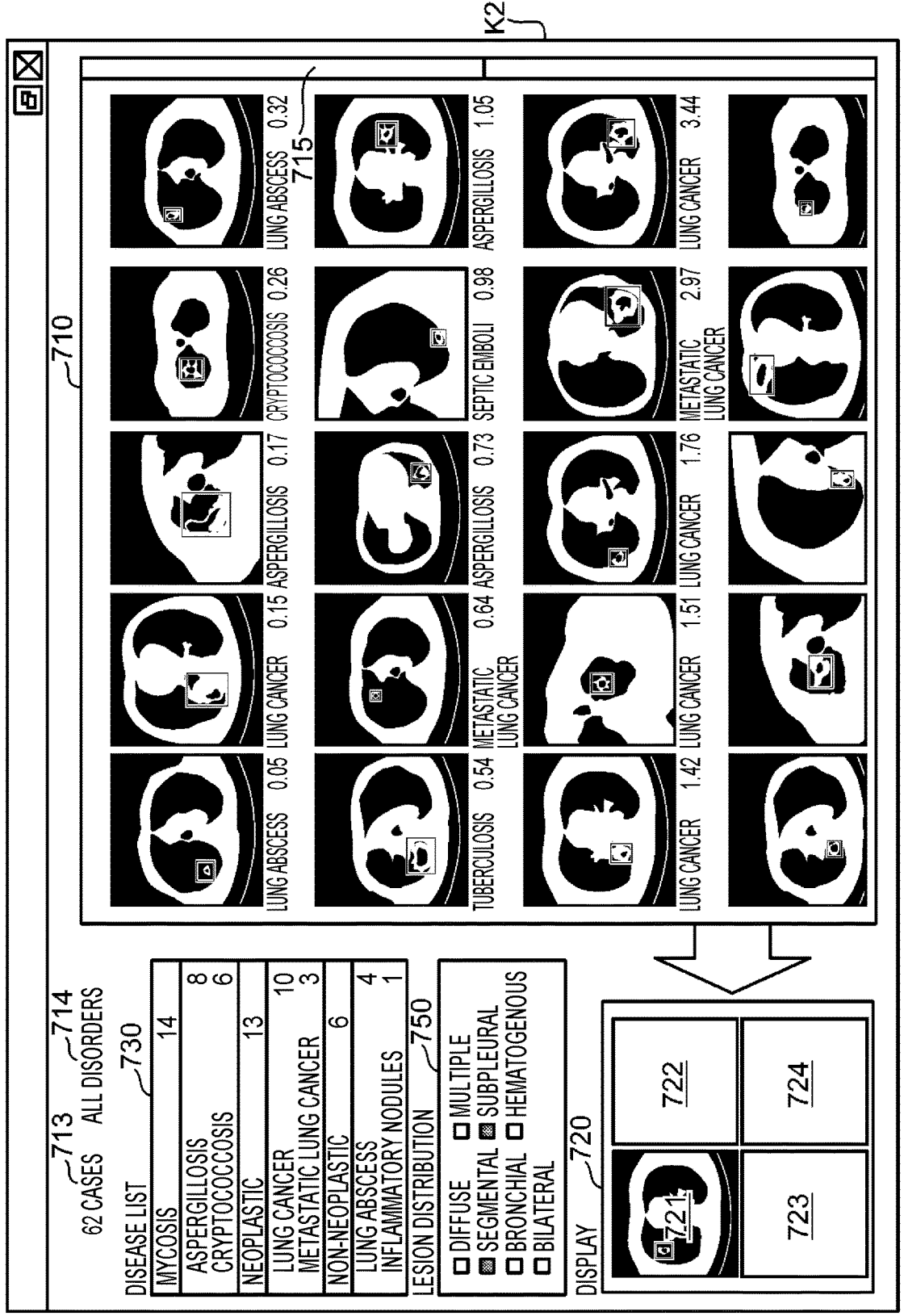
FIG. 6 is a diagram illustrating an example of a basic screen displayed on a display immediately after launching a similar case search application on an information terminal.

FIG. 6 is a diagram illustrating an example of a basic screen K2 displayed on the display 101b immediately after launching the similar case search application on the information terminal 100. The basic screen K2 illustrated in FIG. 6 includes a case display area 710, a layout area 720, a disease list display area 730, and a distribution list display area 750.

In the case display area 710, thumbnail images of similar cases that resemble the search query image are displayed in order of similarity. Herein, the thumbnail images of similar cases are an example of similar medical images. Also, the case display area 710 is an example of a first display area.

Since a large number of similar cases are displayed in the case display area 710, converting the resolutions and pixel values on the spot would be a time-consuming process. Thus, thumbnail images are created in advance from the original slice images, and saved in the case search system 300.

Hereinafter, resolution and pixel value conversion will be elaborated further. The resolution of an original slice image is 512×512 pixels, but since a thumbnail image is of lower resolution, it is necessary to perform resolution conversion. Accordingly, the thumbnail image is generated by performing a downscaling process and a tone conversion process on the original slice image.

The tone conversion process is performed as follows, for example. In a slice image acquired by CT, each pixel value (CT value) takes one of 2000 possible tone value from −1000 to +1000 Hounsfield units (HU), which cannot be displayed directly on an ordinary display with 8-bit tone depth. Additionally, even if such an image can be displayed, from among the 2000 tones, it is difficult for the human eye to distinguish between the emphysema region (CT value: −1000 HU), normal tissue of the lung field (CT value: approximately −900 HU), the ground-glass region (CT value: −800 HU), soft tissue (CT value: −100 to −50 HU), water (CT value: 0 HU), and bone (CT value: 1000 HU).

Thus, ordinarily, a window level and a window width are set for each pixel value of a slice image, and the slice image is reconstructed into 8-bit pixel values and displayed on the display. Herein, the window level indicates a CT value that serves as the center of the window, and the window width indicates the width above and below the window center.

For example, if a DICOM image is reconstructed under a lung field condition, the window level is set from −550 to −800, and the window width is set from 1000 to 1600. Consequently, a thumbnail image is also generated by dropping the pixel values to 8 bits from the original slice image according to the above process.

Note that the thumbnail images displayed in the case display area 710 are thumbnail images indicating similar cases for which the distance to a feature vector of the case to be diagnosed is less than or equal to a certain threshold value. Herein, Euclidean distance is used as the distance, for example. However, a difference measure of distance, such as city block distance, may also be adopted as the distance. Two images being compared are similar to the extent that the distance is short. In addition, a feature vector obtained from the original slice image and not from the thumbnail image is adopted.

Figure 7:
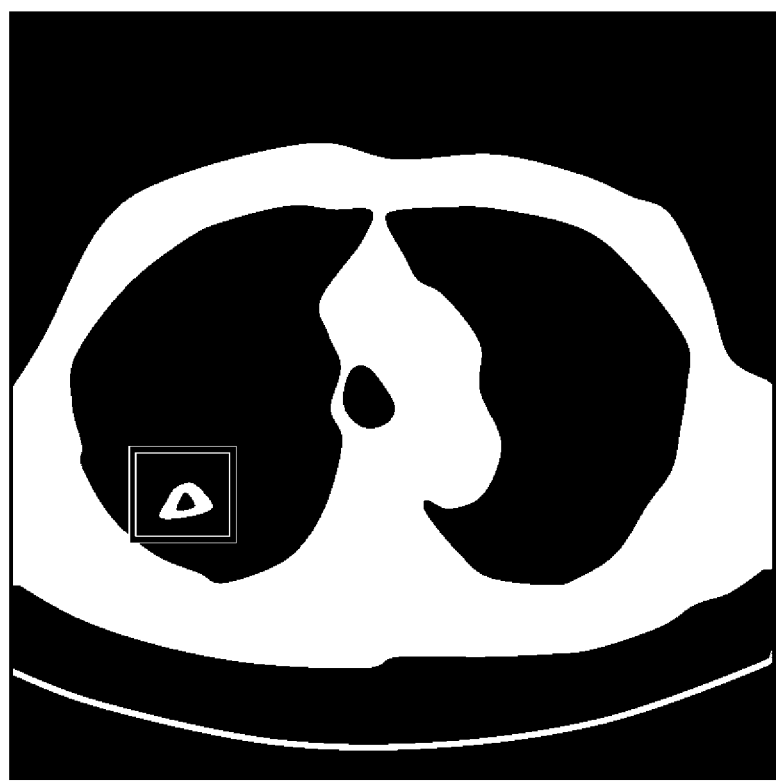
FIG. 7 is a diagram illustrating a display area of one similar case displayed in a case display area.

FIG. 7 is a diagram illustrating a display area (an example of an individual area) of one similar case displayed in the case display area 710. In the display area of the similar case, a thumbnail image is displayed, and below the thumbnail image, a definite diagnosis display area 711 and a distance display area 712 are arranged. In the definite diagnosis display area 711, the name of the disease according to the definite diagnosis of the corresponding similar case is displayed. The name of the disease according to the definite diagnosis refers to the name of the disease whose diagnosis was confirmed for the corresponding similar case. In the distance display area 712, the distance between the feature vector of the slice image of the corresponding similar case and the feature vector of the search query image is displayed. In the example of FIG. 7, "NTM" (nontuberculous mycobacterial infection) is displayed in the definite diagnosis display area 711, thus indicating that the thumbnail image is a thumbnail image of a similar case with a definite diagnosis of NTM. In addition, in the distance display area 712, "0.05" is displayed, thus indicating that the distance between the slice image of this similar case and the search query image is "0.05".

(Case Display Area 710)

Figure 50:
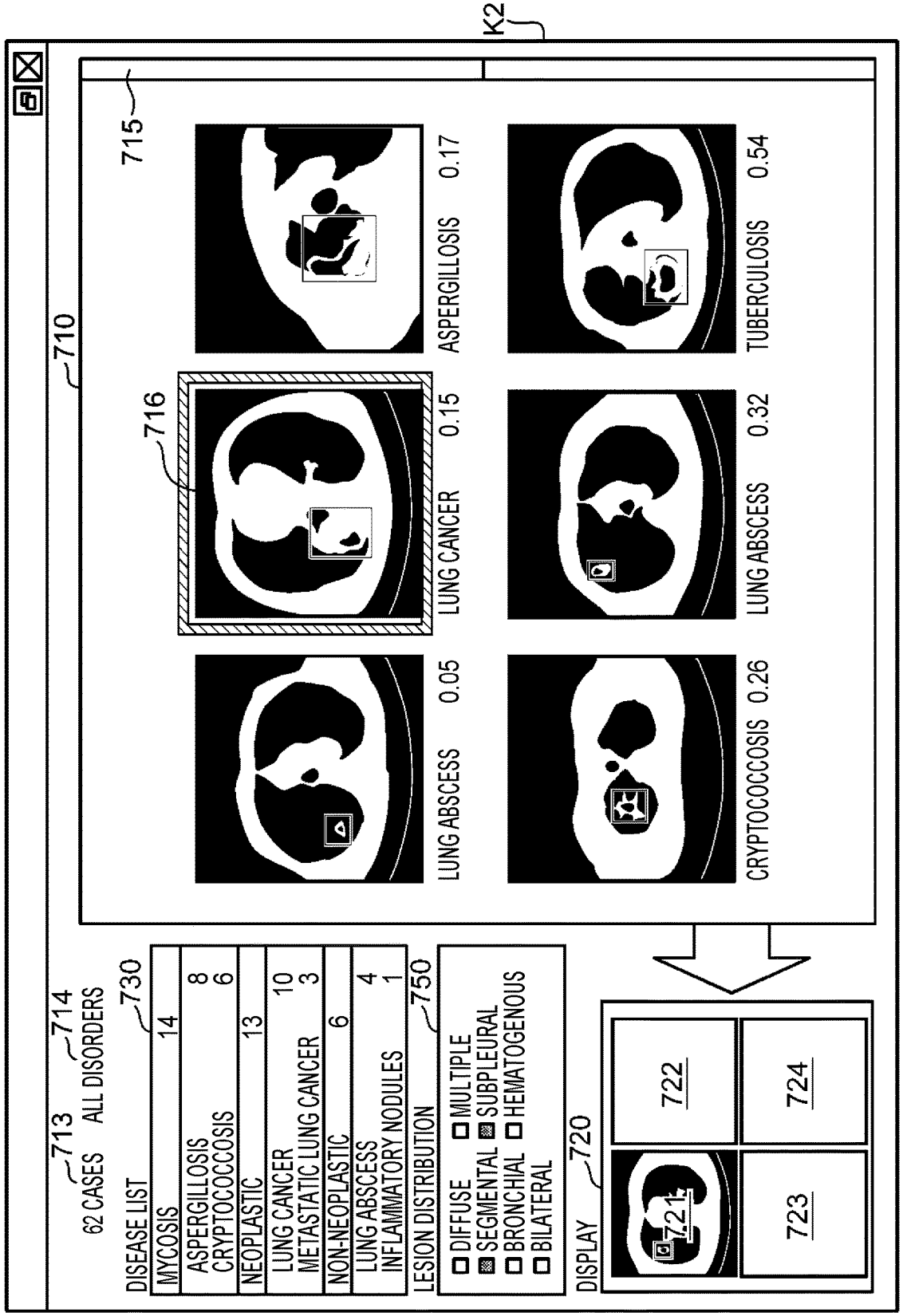
FIG. 50 is a diagram illustrating an example of a state in which a user has selected a thumbnail image on a basic screen immediately after a similar case search.

If the input controller 103 senses an operation of specifying a thumbnail image of a similar case in the case display area 710, the display controller 104 displays a summary image corresponding to the specified thumbnail image from among the series including the specified thumbnail image. FIG. 50 is a diagram illustrating an example of a state in which a user has selected a thumbnail image on the basic screen K2 immediately after a similar case search.

The example in FIG. 50 demonstrates that the cursor is positioned on a thumbnail image 716 of a similar case of lung cancer in the second column of the first row, and this thumbnail image 716 has been selected by the user. At this point, if the mouse is positioned inside the area of the thumbnail image 716, and a click or double-click operation is sensed, the input controller 103 may determine that the thumbnail image 716 is selected. Alternatively, if the cursor is positioned inside the area of the thumbnail image 716 as a result of operating the directional keys on a keyboard, and the Enter key on the keyboard is pressed, the input controller 103 may determine that the thumbnail image 716 is selected.

Subsequently, if the display controller 104 determines that the thumbnail image 716 selected by the user is a localized lesion, the display controller 104 displays a video of successive frame images 717 in the display area 716a of the thumbnail image 716, as illustrated in FIG. 51. In this case, the successive frame images 717 are displayed as the summary image.

FIG. 51 is a diagram illustrating an example of the basic screen K2 when the thumbnail image 716 selected by the user is a localized lesion. Herein, the successive frame images 717 include a certain number of adjacent thumbnail images F1 to F5 including the thumbnail image 716 from the series including the thumbnail image 716. In the example of FIG. 51, the successive frame images 717 include the thumbnail image 716 (F3) in the center, the thumbnail images F1 and F2 of the previous two frames, and the thumbnail images F4 and F5 of the next two frames, for a total of five frames' worth of thumbnail images. Additionally, these five thumbnail images F1 to F5 are displayed in the display area of the thumbnail image 716, at a certain frame rate, and in order from F1 to F5. Note that in FIG. 51, although the successive frame images 717 include the five thumbnail images F1 to F5, this is merely one example. The successive frame images 717 may include more than five thumbnail images, or from 2 to 4 thumbnail images. As illustrated in FIG. 51, in the case in which the selected thumbnail image 716 is a localized lesion, the display area 716*a* of the thumbnail image 716 constitutes an example of a second display area.

On the other hand, if the thumbnail image 716 selected by the user is determined to be a diffuse lesion, the display controller 104 displays representative images 718 of multiple regions constituting the organ illustrated by the thumbnail image 716, in a list with one image for each region, as illustrated in FIG. 52. FIG. 52 is a diagram illustrating an example of the basic screen K2 when the thumbnail image 716 selected by the user is a diffuse lesion. In the example of FIG. 52, the thumbnail image 716 is an image of the lungs. The lungs are made up of three regions: the upper lobe, the middle lobe, and the lower lobe. Consequently, the display controller 104 displays a list of three representative images 718 of the upper lobe, the middle lobe, and the lower lobe. In this case, the representative images 718 constitute the summary image.

In the example of FIG. 52, three representative images 718 are displayed in a list in a summary area 719. Herein, the summary area 719 is displayed below the display area 716*a* of the thumbnail image 716, overlapping the case display area 710. The summary area 719 includes name display fields 718*a* indicating the name of each region inside the organ (upper lobe, middle lobe, lower lobe), and the representative images 718 arranged below the name display fields 718*a*. Note that in the example of FIG. 52, the representative images 718 are lined up horizontally in the summary area 719, but this is merely one example, and the representative images 718 may also be lined up vertically. As illustrated in FIG. 52, in the case in which the selected thumbnail image 716 is a diffuse lesion, the summary area 719 constitutes an example of a second display area. Note that methods of generating the successive frame images 717 and the representative images 718 will be discussed later.

In this way, the display controller 104 changes the summary image to present according to whether the selected thumbnail image 716 is a localized lesion or a diffuse lesion. As a result, thumbnail images of similar cases that serve as a reference for diagnosing a medical image to be interpreted from among a very large number of cases registered in a medical image database 2000 may be presented to the physician effectively. Thus, the present disclosure may contribute to improved diagnosis accuracy by the physician.

Referring again to FIG. 6, a search hit display area 713 is disposed in the top-left of the basic screen K2, for example. In the search hit display area 713 is displayed the number of similar cases resembling the case to be diagnosed that were acquired from the case search system 300 as the results of the search process.

Note that if the number of similar cases is very large, it may not be possible to display all similar cases in the case display area 710 at once. Accordingly, a vertically elongated scrollbar 715 is provided on the right side of the case display area 710, for example. The display controller 104 scrolls the thumbnail images displayed in the case display area 710 up or down, according to the amount of movement of the scrollbar 715. Consequently, the user is able to make similar cases that were in a hidden state be displayed in the case display area 710, and observe those similar cases.

Note that the scrollbar 715 may also be horizontally elongated. In this case, the display controller 104 may scroll the thumbnail images displayed in the case display area 710 to the left or right, according to the amount of movement of the scrollbar 715. Alternatively, if a directional key on the keyboard is pressed while the mouse pointer is positioned in the case display area 710, the display controller 104 may scroll the thumbnail images displayed in the case display area 710 in the direction of the key being pressed, for as long as the key is pressed.

Note that the information terminal 100 is taken to acquire, from the case search system 300, thumbnail images for which the distance to the search query image is less than or equal to a certain threshold value, but this is merely one example. For example, the information terminal 100 may also acquire, from the case search system 300, a fixed number of thumbnail images in order of highest similarity. Alternatively, the information terminal 100 may acquire thumbnail images from the case search system 300 so that a fixed number of thumbnail images of certain diseases according to the definite diagnoses are included.

Note that the technique of displaying thumbnail images in the case display area 710 may adopt a display technique such as displaying the thumbnail image with the shortest distance to the search query image at the left edge of the topmost row, displaying thumbnail images so that the distance successively increases proceeding to the right, and when the right edge of the same row is reached, displaying the thumbnail image with the next-largest distance at the left edge of the second row from the top, for example. In other words, a display technique may be adopted in which thumbnail images are displayed in the case display area 710 in order of smallest distance starting from the top-left and proceeding to the bottom-right in a serpentine manner.

Obviously, the present embodiment may also adopt some other display technique. For example, the present embodiment may also adopt a display technique of displaying the thumbnail image with the shortest distance at the top edge of the first column from the left, displaying thumbnail images so that the distance successively increases proceeding down, and when the bottom edge of the same column is reached, displaying the thumbnail image with the next-largest distance at the top edge of the second column from the left, for example. Additionally, a configuration enabling the user to switch between these multiple display techniques may also be adopted.

Also, although distance is adopted as the similarity in the above example, any indicator of similarity may be adopted insofar as the indicator expresses the resemblance between images, such as cosine similarity. If cosine similarity is adopted, the resemblance between two compared images becomes higher as the value approaches 1.

Note that, although discussed in detail later, the similar cases displayed in the case display area 710 may be filtered by the diseases displayed in the disease list display area 730 or the lesion distributions displayed in the distribution list display area 750. The currently set filter condition on the similar cases is displayed in a display condition display area 714. The example of FIG. 6 illustrates a state immediately after performing a similar case search with no filters applied, and thus "All Disorders" is displayed in the display condition display area 714.

The layout area 720 is disposed in the bottom-left of the basic screen K2 illustrated in FIG. 6, for example. The layout area 720 is used to cause the medical image viewers of the display 101a to display images that the user wants to observe in detail from among the similar case thumbnail images displayed in the case display area 710. As illustrated in FIG. 5, the four medical image viewers 610 to 640 are displayed in a 2×2 grid on the display 101a. In addition, in the layout area 720, four display boxes 721 to 724 exist in a 2×2 grid. In this way, the number and arrangement of the medical image viewers 610 to 640 displayed on the display 101 matches the number and arrangement of the display boxes 721 to 724 in the layout area 720. As illustrated in FIG. 5, the search query image is being displayed in the medical image viewer 610, and correspondingly, a thumbnail image of the search query image is initially displayed in the display box 721.

In the other display boxes 722 to 724, thumbnail images of similar cases are displayed in conjunction with the medical image viewers 620 to 640. In other words, if the input controller 103 senses that a thumbnail image displayed in the case display area 710 has been dragged and dropped into any one of the display boxes 722 to 724, the display controller 104 displays the thumbnail image in the relevant display box, and in addition, displays the slice image corresponding to that thumbnail image in the medical image viewer corresponding to the relevant display box. In this way, the medical image viewers 610 to 640 have a one-to-one association with the display boxes 721 to 724.

In the example of FIG. 6, the display boxes 722 to 724 are blank, and thus the medical image viewers 620 to 640 illustrated in FIG. 5 are also blank. Note that the display boxes 722 to 724 that display similar cases are examples of a second display box.

The user performs drag and drop operations with the mouse to move thumbnail images that the user wants to observe in detail from the case display area 710 to the layout area 720. For example, if the user moves a thumbnail image to the display box 722, the slice image corresponding to that thumbnail image is displayed in the medical image viewer 620 corresponding to the display box 722. Similarly, if the user moves a thumbnail image to the display box 723, the slice image corresponding to that thumbnail image is displayed in the medical image viewer 630 corresponding to the display box 723. In other words, if the user moves a thumbnail image to an arbitrary display box from among the display boxes 721 to 724, a thumbnail image of a similar case is displayed adjacent to the thumbnail image of the search query image. For this reason, the user is able to compare the case to be diagnosed against a similar case at the level of thumbnail images, and rapidly determine the resemblance between the two cases. In other words, since thumbnail images contain less information compared to slice images, the user is able to roughly determine to what extent the case to be diagnosed and the similar cases placed adjacent to each other in the layout area 720 resemble each other. For this reason, the user is able to efficiently narrow down to final candidates of similar cases to compare in detail against the case to be diagnosed at the level of slice images, from among a large number of similar cases displayed in the case display area 710.

Similarly, slice images of the search query image and similar cases are displayed on the display 101a, in the same arrangement as the layout area 720. For this reason, after finishing the work of narrowing down to the similar cases to act as final candidates in the layout area 720, the case to be diagnosed and the similar cases narrowed down as the final candidates are displayed on the display 101a at the level of slice images, without having to input any user operations. For this reason, the user is able to proceed smoothly to the next work step of interpreting in detail the case to be diagnosed and the similar cases acting as the final candidates.

In the top part on the left side of the basic screen K2 illustrated in FIG. 6, the disease list display area 730 is disposed under the heading "Disease List". In the disease list display area 730, the names of the diseases according to the definite diagnoses of all similar cases acquired as the similar case search results are displayed. After the case to be diagnosed is diagnosed and a definite diagnosis is made, that case is stored in the case search system 300 as a similar case. Consequently, each similar case has been assigned a disease according to a definite diagnosis.

FIG. 8 is an enlarged view of the disease list display area 730. In FIG. 8, the names of diseases according to definite diagnoses are displayed split between major disease classifications (731, 734, 737, 741, 744) and fine disease classifications (732, 733, 735, 736, 738, 739, 740, 742, 743, 745). In the example of FIG. 8, Mycosis 731, Neoplastic 734, Non-neoplastic 737, Mycobacteriosis 741, and Other 744 are displayed as major disease classifications.

Also, in the example of FIG. 8, Aspergillosis 732 and Cryptococcosis 733 are displayed as fine disease classifications of Mycosis 731. Also, Lung Cancer 735 and Metastatic Lung Cancer 736 are displayed as fine disease classifications of Neoplastic 734. Also, Lung Abscess 738, Sarcoidosis 739, and Septic Emboli 740 are displayed as fine disease classifications of Non-neoplastic 737. Also, Nontuberculous mycobacteria (NTM) 742 and Tuberculosis 743 are displayed as fine disease classifications of Mycobacteriosis 741. Also, Bronchiectasis 745 is displayed as a fine disease classification of Other 744.

Figure 9:
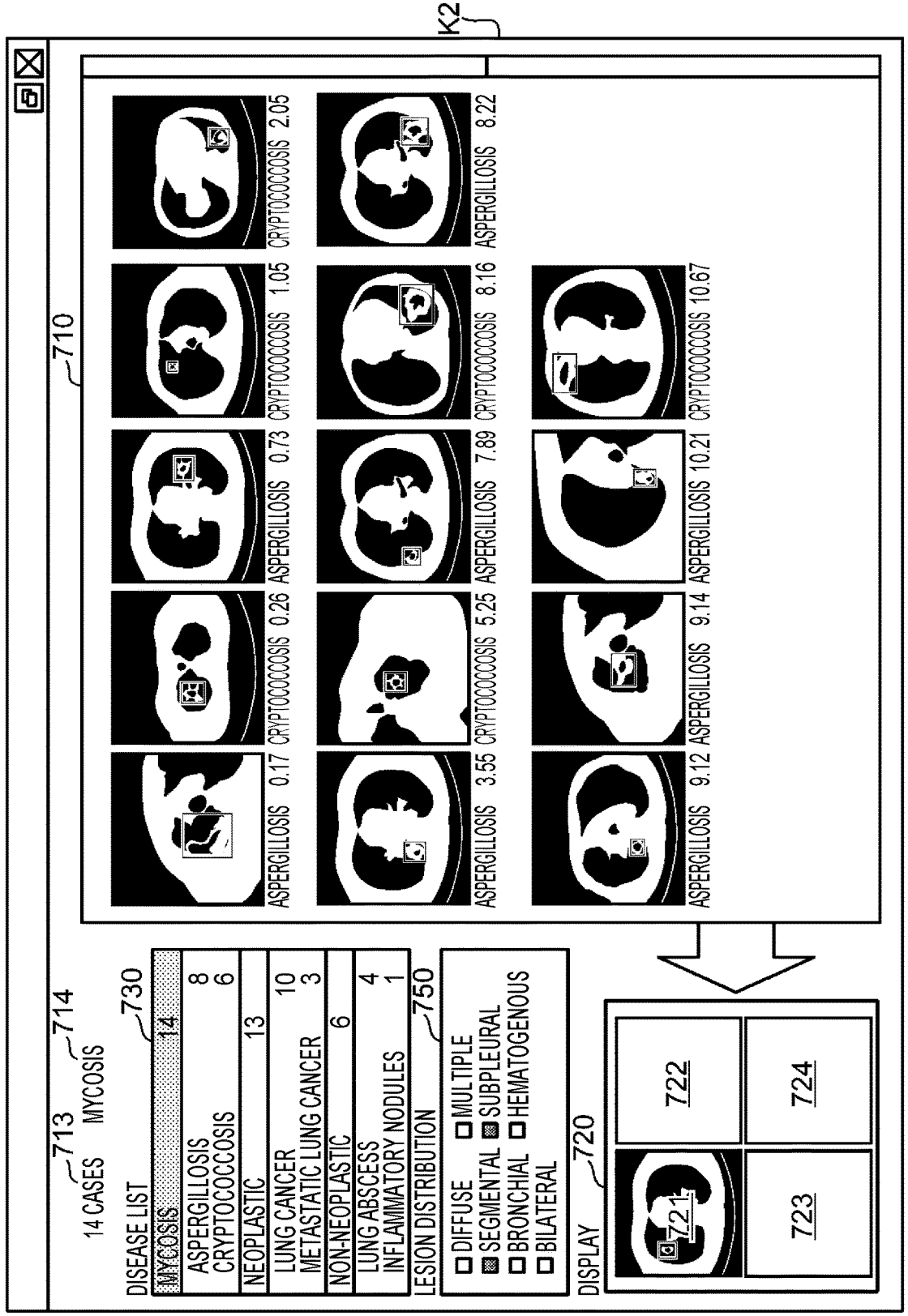
FIG. 9 is a diagram illustrating a basic screen when similar cases are filtered by "mycosis"

In addition, beside each major disease classification and each fine disease classification, the number of cases of that disease is displayed. The user is able to filter the similar cases displayed in the case display area 710 by selecting an arbitrary row of a major disease classification or a fine disease classification in the disease list display area 730. As illustrated in FIG. 6, in the state immediately after a similar case search, 62 similar cases including a variety of disorders are available for display, but if the Mycosis 731 row in FIG. 8 is clicked with the mouse, the display controller 104 displays only the similar cases of mycosis in the case display area 710, as illustrated in FIG. 9. Also, if the Metastatic Lung Cancer 736 row in FIG. 8 is clicked with the mouse, the display controller 104 displays only the similar cases of metastatic lung cancer in the case display area 710, as illustrated in FIG. 10.

At this point, the display controller 104 displays the filtered diseases in the display condition display area 714 so that the user is able to understand the conditions under which the similar cases being displayed in the case display area 710 have been filtered currently. FIG. 9 is a diagram illustrating the basic screen K2 when the similar cases are filtered by "mycosis". FIG. 10 is a diagram illustrating the basic screen K2 when the similar cases are filtered by "metastatic lung cancer".

Figure 10:
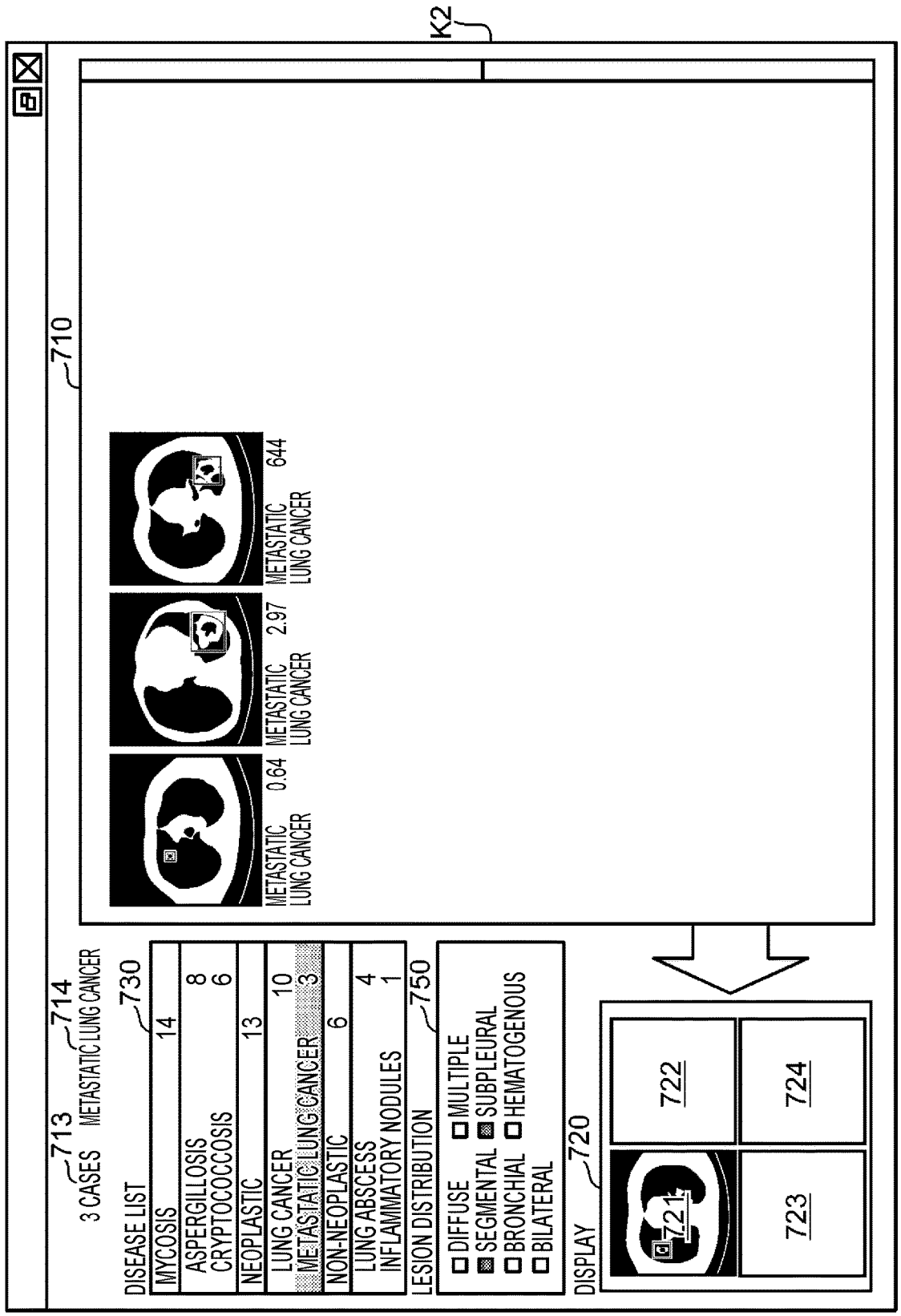
FIG. 10 is a diagram illustrating a basic screen when similar cases are filtered by "metastatic lung cancer"

In the example of FIG. 9, since a "mycosis" filter has been applied, "Mycosis" is displayed in the display condition display area 714, whereas in FIG. 10, since a "metastatic lung cancer" filter has been applied, "Metastatic Lung Cancer" is displayed in the display condition display area 714.

Also, at this point, the display controller 104 displays the number of search hits in the search hit display area 713 so that the user is able to understand how many similar cases are being displayed in the case display area 710 currently. In the example of FIG. 9, there are 14 similar cases corresponding to "mycosis", and thus "14 Cases" is displayed in the search hit display area 713, whereas in the example of FIG. 10, there are three similar cases corresponding to "metastatic lung cancer", and thus "3 Cases" is displayed in the search hit display area 713.

According to this function, only the similar cases of a disease assumed by the physician as the target of image diagnosis are displayed in the case display area 710, and the physician is able to easily check whether or not the case to be diagnosed contradicts the assumed disease.

In the middle part on the left side of the basic screen K2 illustrated in FIG. 6, the distribution list display area 750 is disposed under the heading "Lesion Distribution". In the distribution list display area 750, types of lesion distributions of all similar cases acquired from the case search system 300 as a result of searching for similar cases are displayed.

Figure 11:
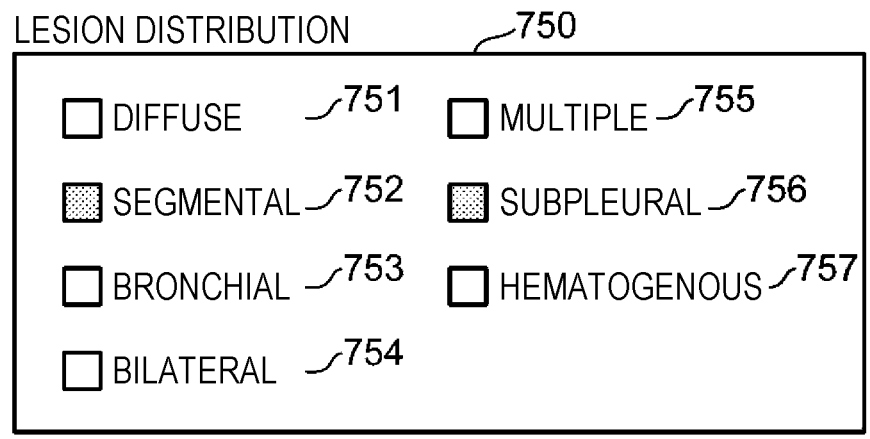
FIG. 11 is an enlarged view of a distribution list display area.

FIG. 11 is an enlarged view of the distribution list display area 750. In the example of FIG. 11, the names of seven lesion distributions are displayed, and a checkbox is disposed on the left side of each name of a lesion distribution. In the example of FIG. 11, Diffuse 751, Segmental 752, Bronchial 753, Bilateral 754, Multiple 755, Subpleural 756, and Hematogenous 757 are displayed as lesion distributions.

These lesion distributions are predefined, and each similar case is assigned in advance distribution flag values indicating whether or not any of the distributions from Diffuse 751 to Hematogenous 757 are applicable (applicable: 1, not applicable: 0). Depending on the similar case, all distribution flag values may be set to not applicable (0) in some cases, whereas multiple distribution flag values may be set to applicable (1) in other cases.

The case search system 300 according to the present embodiment searches for similar cases having a region of interest that resembles a region of interest set by the user in a slice image of the case to be diagnosed. Lesions may also exist in slice images other than the slice image in which the user set the region of interest. Additionally, in some situations, after searching for similar cases by using a slice image with a region of interest set, the user may want to compare the similar cases found by the search with slice images other than the slice image that was used to perform the search. In such situations, the user inputs a slice-cycling operation to display another slice image in the medical image viewer 610, and performs the work of comparing the other slice image to the similar cases found by the search. At this point, if only similar cases related to the lesion that the user is focusing on were displayed in the case display area 710 from among all the similar cases found by the search, the user would be able to perform smoothly the work of extracting slice images having the desired lesion from among the slice images other than the slice image in which the region of interest was set. Accordingly, the present embodiment, a function of filtering the similar cases found by search according to a desired lesion distribution is provided to enable such work to be performed more smoothly.

In the present embodiment, the lesion distributions indicated from Diffuse 751 to Hematogenous 757 in FIG. 11 are adopted as lesion distributions in the lung field region. Also, like in FIG. 11, regarding the check boxes and lesion distributions, the display controller 104 displays filterable lesion distributions in an active state, and displays non-filterable lesion distributions in an inactive state. Herein, for the active state, a state in which the brightness is high compared to the inactive state is adopted, whereas for the inactive state, a state in which the brightness is low compared to the active state is adopted.

In the example of FIG. 11, Diffuse 751, Bronchial 753 to Multiple 755, and Hematogenous 757 are displayed in the active state, while Segmental 752 and Subpleural 756 are displayed in the inactive state. This is because currently, the distribution flag value for each of Diffuse 751, Bronchial 753 to Multiple 755, and Hematogenous 757 is set to 1 (applicable) for at least one similar case from among all the similar cases acquired by the similar case search, whereas the distribution flag value for each of Segmental 752 and Subpleural 756 is set to 0 (not applicable) for all of the acquired similar cases.

If the input controller 103 senses that a checkmark has been input into one or more check boxes among the check boxes in the active state, the display controller 104 displays in the case display area 710 only the similar cases corresponding to the one or more checked lesion distributions.

Note that for Segmental 752 and Subpleural 756, the distribution flag value is set to 0 (not applicable) for all of the similar cases acquired as the search results. For this reason, if a configuration allowing Segmental 752 and Subpleural 756 to be checked were adopted, and checkmarks were input into these lesion distributions, no similar cases would be displayed in the case display area 710 at all, inputting the checkmarks would be meaningless. Accordingly, in the present embodiment, to avoid such situations, lesion distributions for which the distribution flag value is 0 (not applicable) for all similar cases acquired as the search results are displayed in the inactive state.

Figure 12:
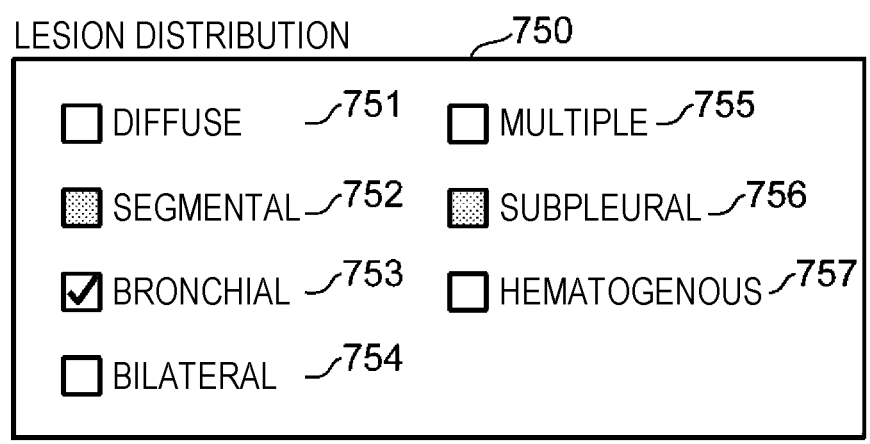
FIG. 12 is a diagram illustrating a distribution list display area into which a checkmark has been input.
Figure 13:
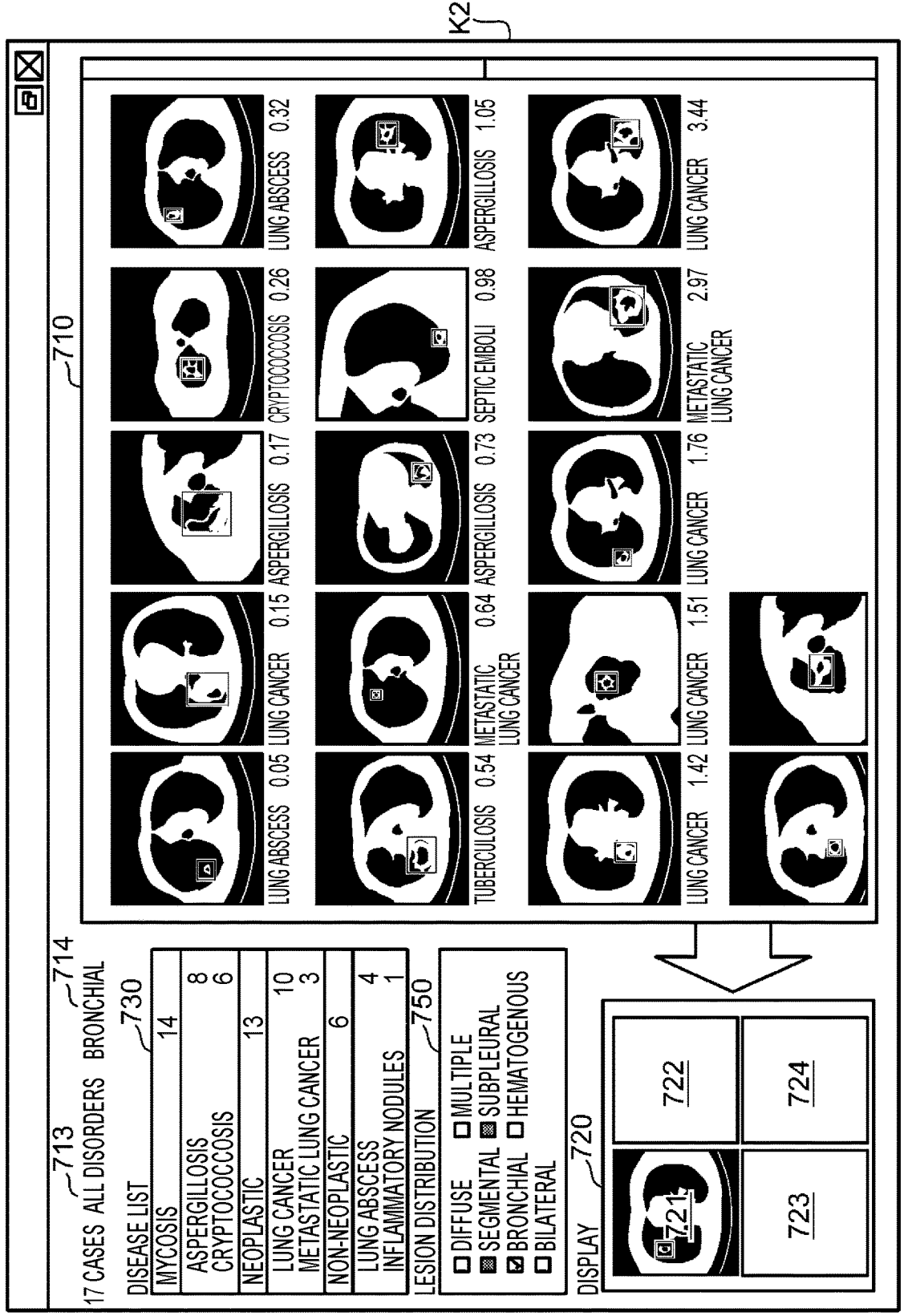
FIG. 13 is a diagram illustrating a basic screen filtered by bronchial lesion distribution.

FIG. 12 is a diagram illustrating the distribution list display area 750 into which a checkmark has been input. FIG. 13 is a diagram illustrating the basic screen K2 filtered by bronchial lesion distribution. When a checkmark is input into the check box for Bronchial 753, as illustrated in FIG. 12, the display controller 104 displays only the similar cases having a bronchial lesion distribution in the case display area 710, as illustrated in FIG. 13. In this example, there are 17 similar cases having a bronchial lesion distribution. For this reason, the display controller 104 displays "17 Cases" in the search hit display area 713. Additionally, in the display condition display area 714, the display controller 104 displays the name of the disease to be displayed, and the name of the lesion distribution, namely "Bronchial". In the example of FIG. 13, a filter by the diseases listed the disease list display area 730 has not been applied, and thus "All Disorders" is displayed in the display condition display area 714.

Figure 15:
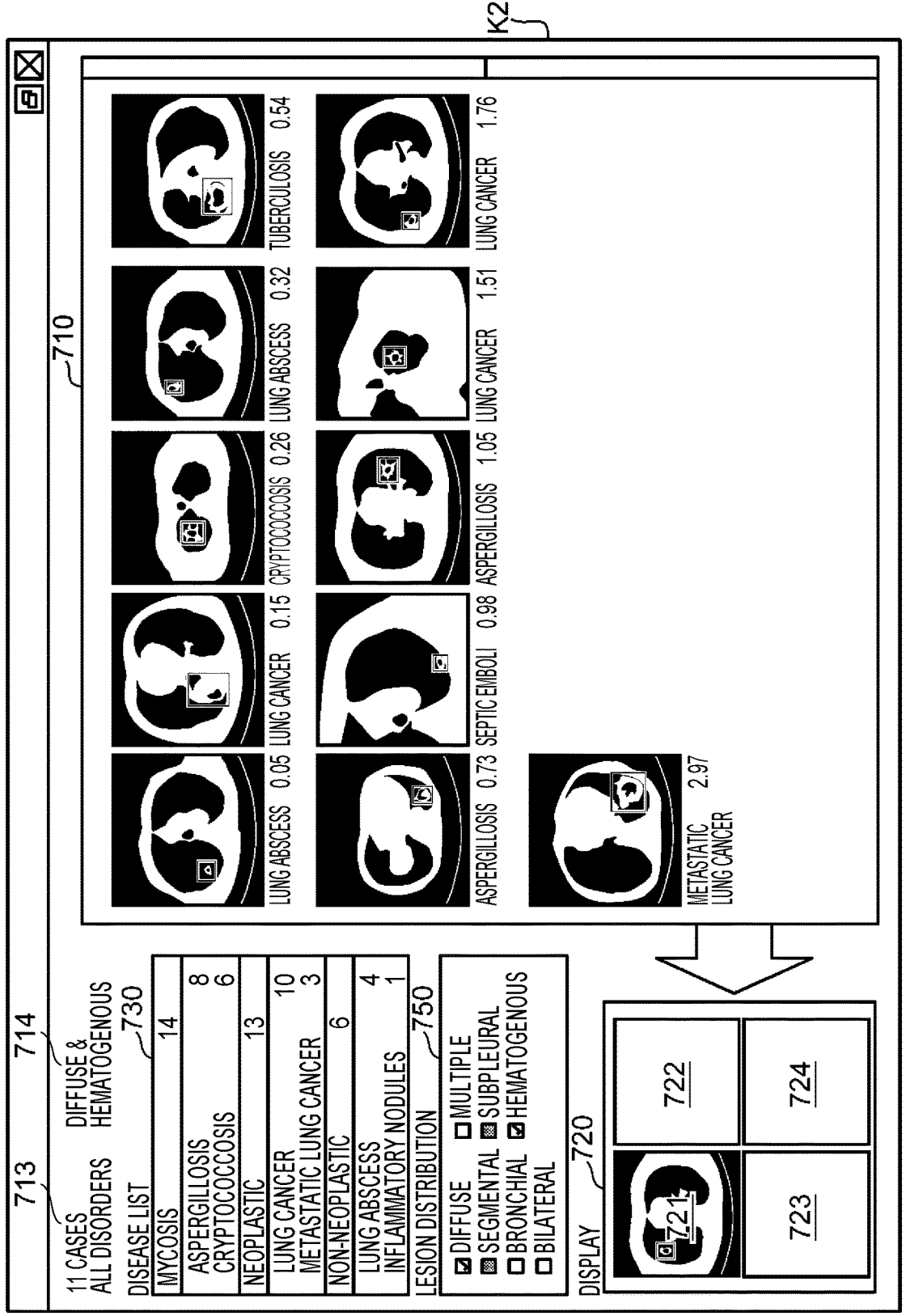
FIG. 15 is a diagram illustrating a basic screen filtered by multiple lesion distributions.

FIG. 14 is a diagram illustrating the distribution list display area 750 into which multiple checkmarks have been input. FIG. 15 is a diagram illustrating the basic screen K2 filtered by multiple lesion distributions. In the example of FIG. 14, checkmarks have been input into Diffuse 751 and Hematogenous 757. For this reason, the display controller 104 displays similar cases having diffuse and hematogenous lesion distributions in the case display area 710, as illustrated in FIG. 15. In this example, there are 11 similar cases having diffuse and hematogenous lesion distributions. For this reason, the display controller 104 displays "11 Cases" in the search hit display area 713. Additionally, in the display condition display area 714, the display controller 104 displays the name of the disease to be displayed (herein, since a filter by disease is not applied, "All Disorders"), and the names of the lesion distributions, namely "Diffuse & Hematogenous".

FIG. 16 is a diagram illustrating a data structure of the patient information 1000. The patient information 1000 is stored in the patient information storage 201 for each patient and managed by the patient information manager 202 in the medical information management system 200. In the patient information 1000, personal information such as the sex and age of the patient, clinical information such as a medical history, and examination information such as a blood test are registered. As illustrated in FIG. 16, the patient information 1000 includes a patient ID 1100, a name 1200, an age 1300, a sex 1400, a medical history 1500, a family history 1600, a chief complaint 1700, examination information 1800, and a definite diagnosis 1900.

The patient ID 1100 is an identifier unique to the patient. The name 1200, the age 1300, the sex 1400, the medical history 1500, the family history 1600, and the chief complaint 1700 are the name, the sex, the medical history, the family history, and the chief complaint of the patient with the patient ID 1100, respectively. The examination information 1800 expresses information related to one or more examinations that the patient has undertaken in the past, as illustrated in FIG. 17.

FIG. 17 is a diagram illustrating a data structure of the examination information 1800 registered in the patient information 1000 illustrated in FIG. 16. The examination information 1800 is information related to examinations performed on the patient, and one set of examination information 1800 is created in correspondence with one examination. The examination information 1800 includes an examination ID 1810, an examination date 1820, an examination type 1830, and an examination result 1840. The examination ID 1810 is an identifier unique to an examination. The examination date 1820 is the date when the examination was performed. The examination type 1830 is the type of examination. The type of examination may be a blood test, a respiratory function test, an endoscopic examination, a plain X-ray scan, or a CT scan, for example.

In the case of a blood test, the examination result 1840 corresponds to the values of various indicators, such as the white blood cell count, LDH level, and GPT level. In addition, the examination result 1840 also corresponds to information such as a judgment made by a physician based on the various indicators. Also, in the case of an image scan such as a plain X-ray scan or a CT scan, pointer information to the captured images or pointer information to a report of the image diagnosis result is included. Note that images captured during an examination are stored in DICOM format in the medical image data storage 203 of the medical information management system 200.

In addition, if the examination type 1830 is an image scan such as a plain X-ray, CT, MRI, or PET scan, the resulting medical image data is archived in the medical image database 2000, which is stored in the medical image data storage 203 of the medical information management system 200.

Figure 18A:
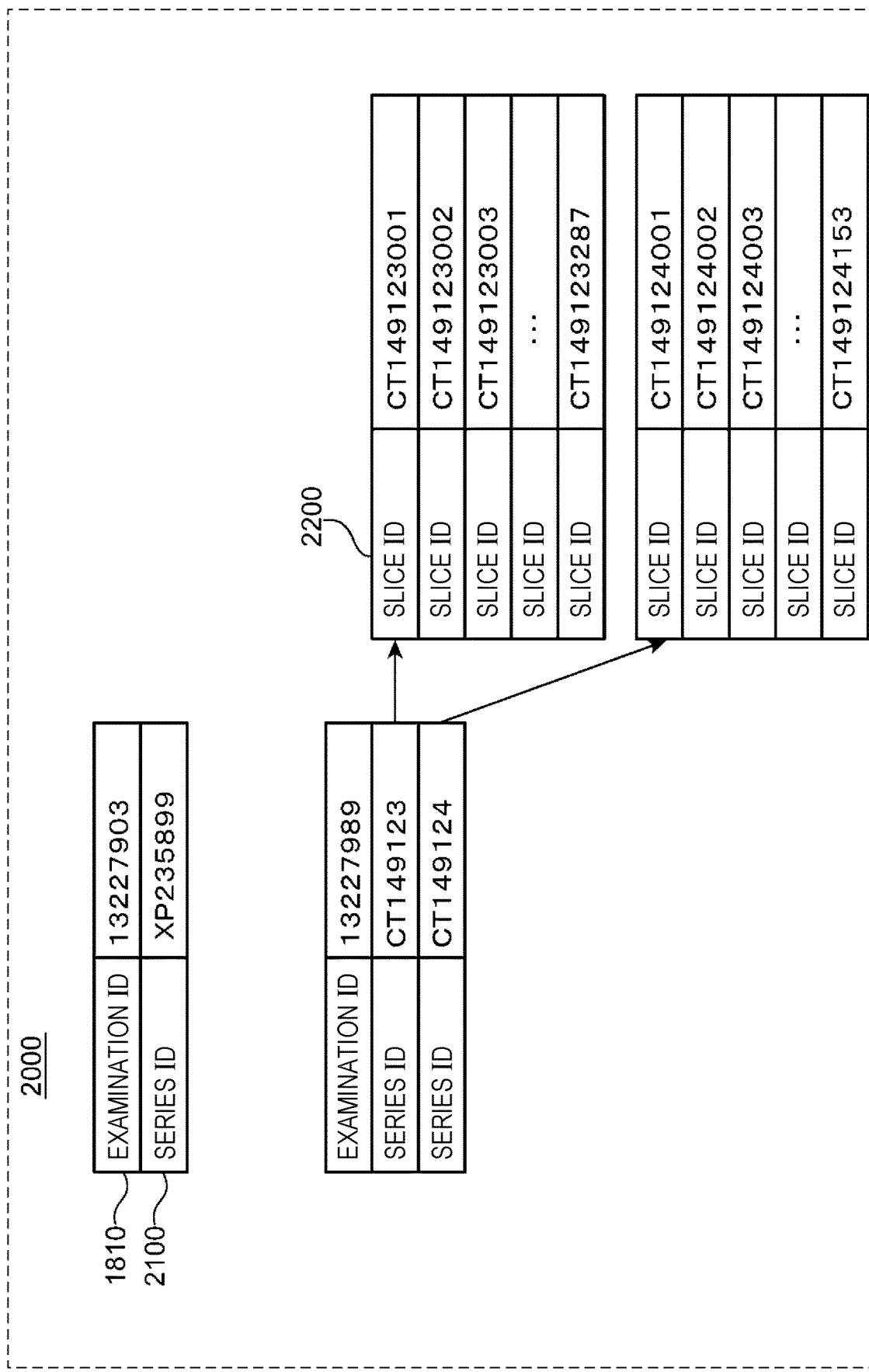
FIG. 18A is a diagram illustrating a data structure of a medical image database.

FIG. 18A is a diagram illustrating a data structure of the medical image database 2000. The medical image database 2000 includes the examination ID 1810 and a series ID 2100. Since multiple types of imaging (such as plain CT and contrast-enhanced CT, for example) may be conducted during a single examination, multiple series IDs 2100 may be associated with one examination ID 1810 in some cases. In other words, a number of series corresponding to the types of imaging is obtained.

In addition, different series may be obtained not only for separate types of imaging, but also for separate conditions of reconstructing the captured images. For example, if the captured images are reconstructed according to a lung field condition and a mediastinum condition, one series is obtained for each of these conditions. Note that in images reconstructed according to a lung field condition, features such as the blood vessels, the bronchi, and the alveoli of the lungs are highlighted for display. Meanwhile, in images reconstructed according to a mediastinum condition, mediastinum features such as blood vessels and lymph nodes are highlighted for display. Since a lung field condition and a mediastinum condition may be obtained by reconstructing images obtained by a single scan, if a plain CT scan and a contrast-enhanced CT scan are both conducted, and the images from these two scans are reconstructed according to a lung field condition and a mediastinum condition, respectively, two series of the lung field condition and two series of the mediastinum condition will be obtained.

In the case of CT and MRI image scans, multiple slice images are obtained from a single scan, and thus multiple slice IDs 2200 are associated with one series ID 2100. In FIG. 18A, the two series IDs "CT149123" and "CT149124" are associated with the examination ID "13227989", thus demonstrating that two series of CT images were obtained from this examination. FIG. 18A also demonstrates how multiple slice IDs 2200 are associated with each of the series IDs "CT149123" and "CT149124".

For multiple slice IDs corresponding to one series ID, as a numerical value included in each slice ID becomes larger, the tomographic planes of the slice images specified by each slice ID may be taken to move in one direction of the patient's body. For example, suppose that there are 10 slice IDs associated with one series ID, with the slice IDs numbered from 1 to 10. In this case, the slice image specified by the slice ID of 1 may be the image in the tomographic plane closest to the tip of the patient's head from among the 10 images, while the slice image specified by the slice ID of 2 may be the image in the tomographic plane that is 2nd closest to the tip of the patient's head from among the 10 images, and so on to the slice image specified by the slice ID of 10, which may be the image in the tomographic plane that is 10th closest to the tip of the patient's head from among the 10 images.

As illustrated in FIG. 18B, the medical image database 2000 may also store, in association with each slice ID, a slice image (set of pixel values) in DICOM format captured in the examination specified by the slice ID.

Figure 18C:
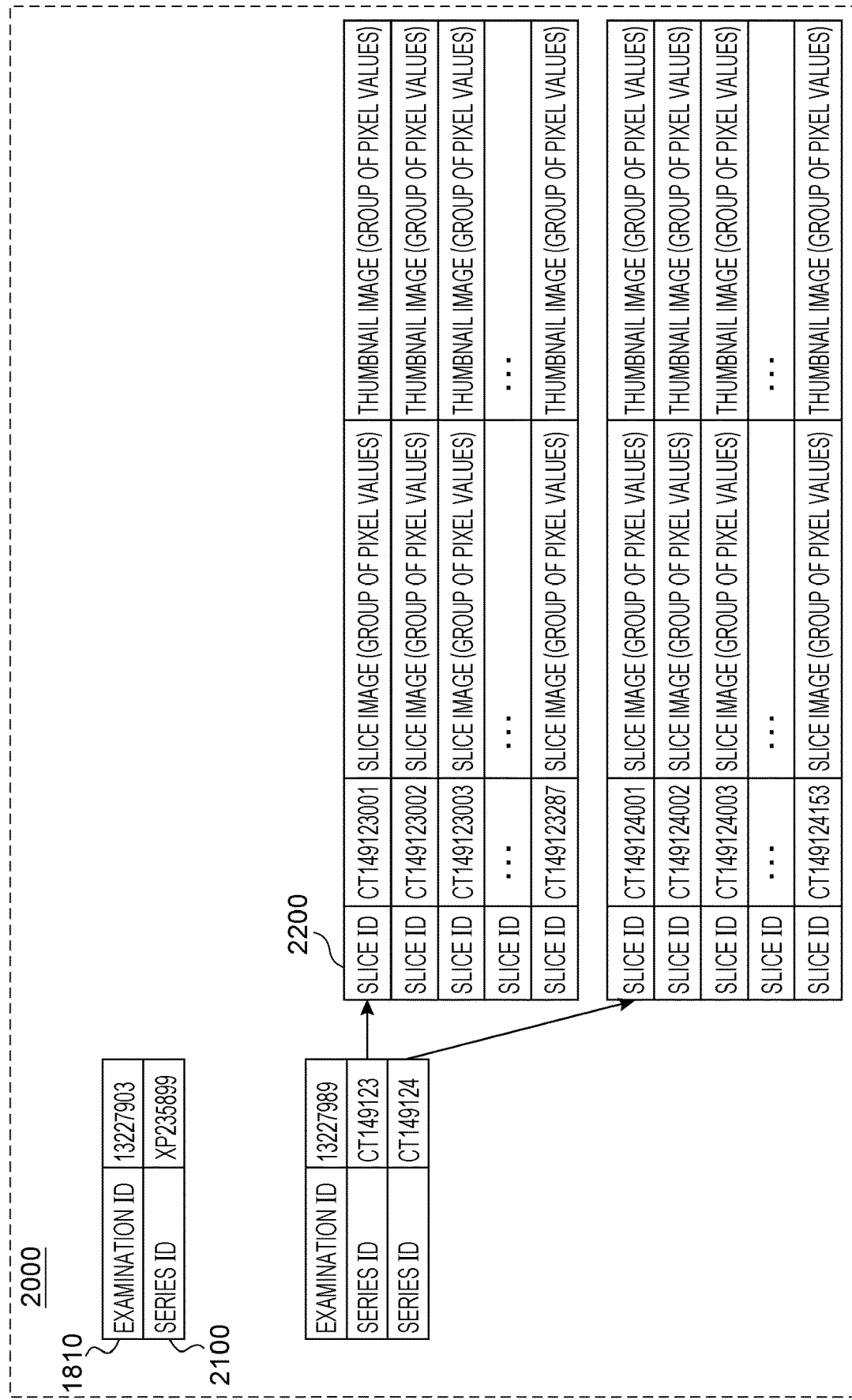
FIG. 18C is a diagram illustrating a data structure of a medical image database.

As illustrated in FIG. 18C, the medical image database 2000 may also store, in association with each slice ID, a thumbnail image (set of pixel values) of a slice image in DICOM format captured in the examination specified by the slice ID. The medical information management system 200 may also generate thumbnail images of slice images in DICOM format. Thumbnail images of slice images in DICOM format will be discussed later.

If the examination type 1830 is an image scan such as a plain X-ray, CT, MRI, or PET scan, a diagnosis report 3000 as illustrated in FIG. 19 is stored in the diagnosis report manager 205 of the medical information management system 200. In the diagnosis report 3000, the results of a diagnosis made by a physician for each examination are registered. FIG. 19 is a diagram illustrating a data structure of the diagnosis report 3000.

The diagnosis report 3000 includes an examination ID 1810, observations 3100, and a diagnosis 3200. The examination ID 1810 is the same as the examination ID 1810 illustrated in FIG. 17. Consequently, the diagnosis report 3000 and the examination information 1800 are associated together. In the observations 3100, remarks expressing the physician's opinions with respect to the examination are registered. In the diagnosis 3200, remarks expressing the physician's diagnosis with respect to the examination are registered.

FIG. 20 is a diagram illustrating a first example of a data structure of diffuse similar case data 4000. The similar case data 4000 is data referenced when searching for similar cases that resemble the case to be diagnosed, and one set of similar case data 4000 is created in correspondence with one similar case. Note that the similar case data 4000 is an example of metadata for similar case data. The similar case data 4000 is stored for each similar case in the similar case data storage 301 of the case search system 300. As illustrated in FIG. 20, the similar case data 4000 includes a similar case ID 4100, a slice ID 4200, region of interest information 4300, image feature data 4400, thumbnail image data 4500, lesion distribution information 4600, a definite diagnosis (major disease classification) 4700, a definite diagnosis (fine disease classification) 4800, a lesion attribute 4900, and summary images 4910.

The similar case ID 4100 is an identifier of the similar case data 4000. Herein, since one set of similar case data is generated for each region of interest set in a slice image of a similar case, the similar case ID 4100 may also be said to be an identifier of a region of interest. In the example of FIG. 20, the similar case ID 4100 is a string made up of the letters "SIM" followed by a number.

Figure 22:
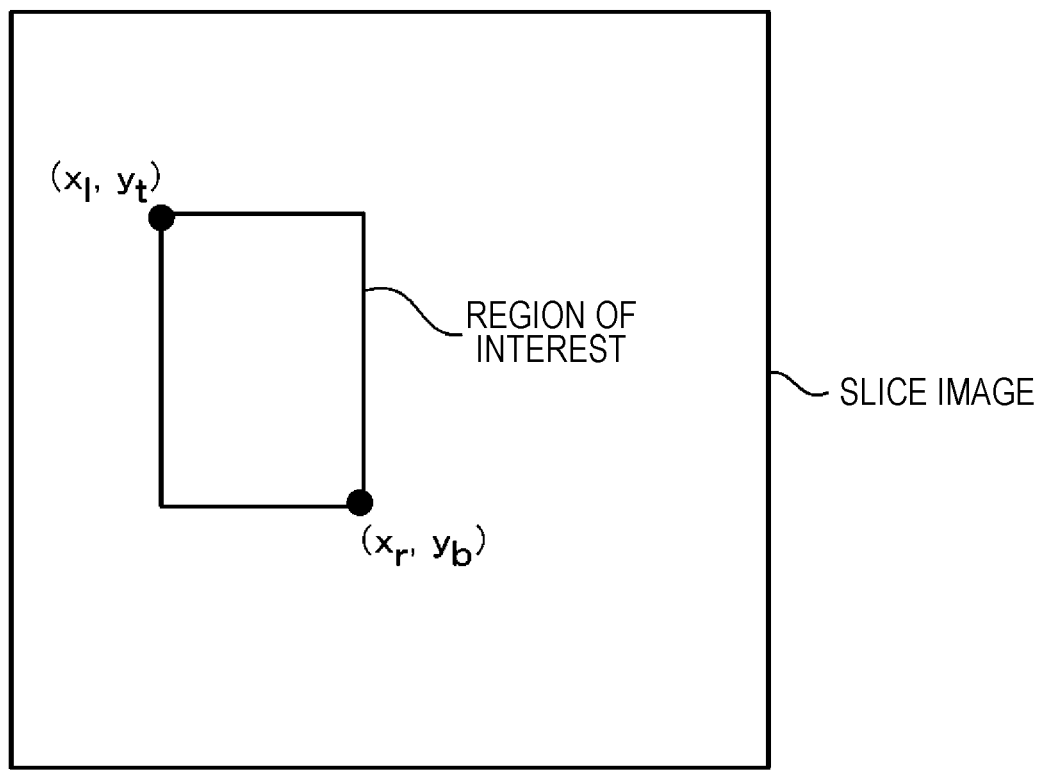
FIG. 22 is a diagram schematically illustrating a region of interest set in a slice image.

The slice ID 4200 is an identifier of a slice image in which a region of interest is set, and is the same as the slice ID 2200 illustrated in FIG. 18A. The region of interest information 4300 is information indicating the position of the region of interest set in the slice image. FIG. 22 is a diagram schematically illustrating a region of interest set in a slice image. In the example of FIG. 22, a rectangular region of interest is set. Consequently, the region of interest information 4300 includes four values: the coordinates of the top-left vertex $(x_t, y_t)$, and the coordinates of the bottom-right vertex $(x_r, y_b)$ of the region of interest. Obviously, the region of interest may also be a shape other than rectangular, and in such a situation, parameters enabling a region to be specified uniquely are adopted as the region of interest information 4300. For example, if the region of interest is a circle, the center coordinates and the radius of the circle are adopted as the region of interest information 4300.

The image feature data 4400 includes feature values of certain dimensionality (herein, N dimensions) extracted from the region of interest defined by the region of interest information 4300. The thumbnail image data 4500 is the image data of a thumbnail image generated for display in the case display area 710, based on the slice image in DICOM format specified by the slice ID. Herein, in the thumbnail image data 4500, the pixel values of the thumbnail image are arranged in raster scan order proceeding from the top-left vertex to the bottom-right vertex of the thumbnail image, for example. As described earlier, a DICOM image obtained by a CT scan is a 512×512 pixel, 11-bit (pixel values ranging from −1000 to +1000) image. Accordingly, in the present embodiment, to speed up the display of thumbnail images, a downscaling process and a tone conversion process are performed on the DICOM image that serves as the basis for a thumbnail image, and a thumbnail image having 8-bit pixel values is created in advance and registered in the similar case data 4000. Note that thumbnail images may be created by having the medical information management system 200 create and transmit thumbnail images to the case search system 300, or by having the case search system 300 create thumbnail images by acquiring DICOM images from the medical information management system 200, for example.

The lesion distribution information 4600 includes distribution flag values indicating whether or not any predetermined lesion distributions from Diffuse 4610 to Hematogenous 4670 are applicable to the relevant similar case (applicable: 1, not applicable: 0).

The definite diagnosis (major disease classification) 4700 is the name of the major disease classification confirmed for the relevant similar case. The definite diagnosis (major disease classification) 4700 is used when filtering similar cases by the name of a major disease classification.

The definite diagnosis (fine disease classification) 4800 is the name of the fine disease classification confirmed for the relevant similar case. The definite diagnosis (fine disease classification) 4800 is used when filtering similar cases by the name of a minor disease classification.

The major disease classification is predefined in unique correspondence with the definite diagnosis (fine disease classification) 4800, and the definite diagnosis (major disease classification) 4700 is stored in the similar case data 4000 by using this correspondence relationship.

The definite diagnosis (major disease classification) 4700 and the definite diagnosis (fine disease classification) 4800 are registered as follows. In the medical image data storage 203, the series ID 2100 is specified from the slice ID 2200 illustrated in FIG. 18A. Subsequently, in the patient information storage 201, the examination ID 1810 is specified from the specified series ID 2100, the corresponding patient information 1000 (see FIG. 16) is specified from the examination ID 1810, and the definite diagnosis 1900 of the relevant patient is specified from the specified patient information 1000. Subsequently, the specified definite diagnosis is registered in the definite diagnosis (major disease classification) 4700 and the definite diagnosis (fine disease classification) 4800.

The lesion attribute 4900 is information indicating whether the relevant similar case is a localized lesion or a diffuse lesion. In FIG. 20, the relevant similar case is a diffuse lesion, and thus "Diffuse" is registered in the lesion attribute 4900.

In the summary images 4910, the slice IDs of summary images of the relevant similar case are stored. In FIG. 20, the relevant similar case is a diffuse lesion, and thus the slice ID (CT149391007) of a representative image of the upper lobe, the slice ID (CT149391025) of a representative image of the middle lobe, and the slice ID (CT149391043) of a representative image of the lower image are registered in the summary images 4910. Also, in the example of FIG. 20, the relevant similar case is a similar case regarding the middle lobe, and the same slice ID (CT149391025) as the slice ID registered in the slice ID 4200 is registered as the slice ID of the representative image of the middle lobe in the summary images 4910, but this is merely one example. For example, a slice ID of the middle lobe that is different from the slice ID registered in the slice ID 4200 (for example, CT149391027) may also be registered in the summary images 4910. Consequently, a thumbnail image that is different from the thumbnail image of the relevant similar case is displayed in the case display area 710 as a summary image, and a greater variety of information may be presented to the user. Note that in the example of FIG. 20, one slice ID each in the upper lobe, the middle lobe, and the lower lobe is registered in the summary images 4910, but this is merely one example. For example, if two or more representative images 718 in the upper lobe, the middle lobe, and the lower lobe are to be displayed, two or more slice IDs from each of the upper lobe, the middle lobe, and the lower lobe may be registered in the summary images 4910.

FIG. 21A is a diagram illustrating a first example of a data structure of localized similar case data 4000. Since FIG. 21A illustrates localized similar case data 4000, the information registered in the definite diagnosis 4700, the lesion attribute 4900, and the summary images 4910 is correspondingly different from FIG. 20. Specifically, in the lesion distribution information 4600 illustrated in FIG. 21A, "0" is registered in Diffuse 4610 while "1" is registered in Hematogenous 4670 compared to FIG. 20. Also, "Neoplastic" is registered in the definite diagnosis 4700, and "Lung Cancer" is registered in the definite diagnosis 4800. Also, in FIG. 21A, "Localized" is registered in the lesion attribute 4900. Also, in FIG. 21A, the slice ID (CT149391025) registered in the slice ID 4200, as well as the two preceding slice IDs (CT149391023 and CT149391024) and the two succeeding slice IDs (CT149391026 and CT149391027) are registered in the summary images 4910. Note that in FIG. 21A, five slice IDs are registered in the summary images 4910, but this is merely one example, and the number of slice images registered in the summary images 4910 varies according to the number of thumbnail images constituting the successive frame images 717 (see FIG. 51).

FIG. 21B is a diagram illustrating a second example of a data structure of localized similar case data 4000. The similar case data 4000 in FIG. 21B differs from FIG. 21A by including a region 4940 instead of the summary images 4910. The region 4940 indicates which region of an organ the relevant similar case belongs to. Since the similar case in FIG. 21B belongs to the middle lobe of the lungs, "Middle Lobe" is registered in the region 4940. In the case of adopting the structure in FIG. 21B, storing slice IDs is not necessary, and thus the creation of the similar case data 4000 becomes easy.

(Flow from Image Selection to Similar Case Search)

Next, the flow from the start of radiological interpretation work to the start of a similar case search in which the information terminal 100 works in conjunction with the medical information management system 200 and the case search system 300 will be described.

Figure 23:
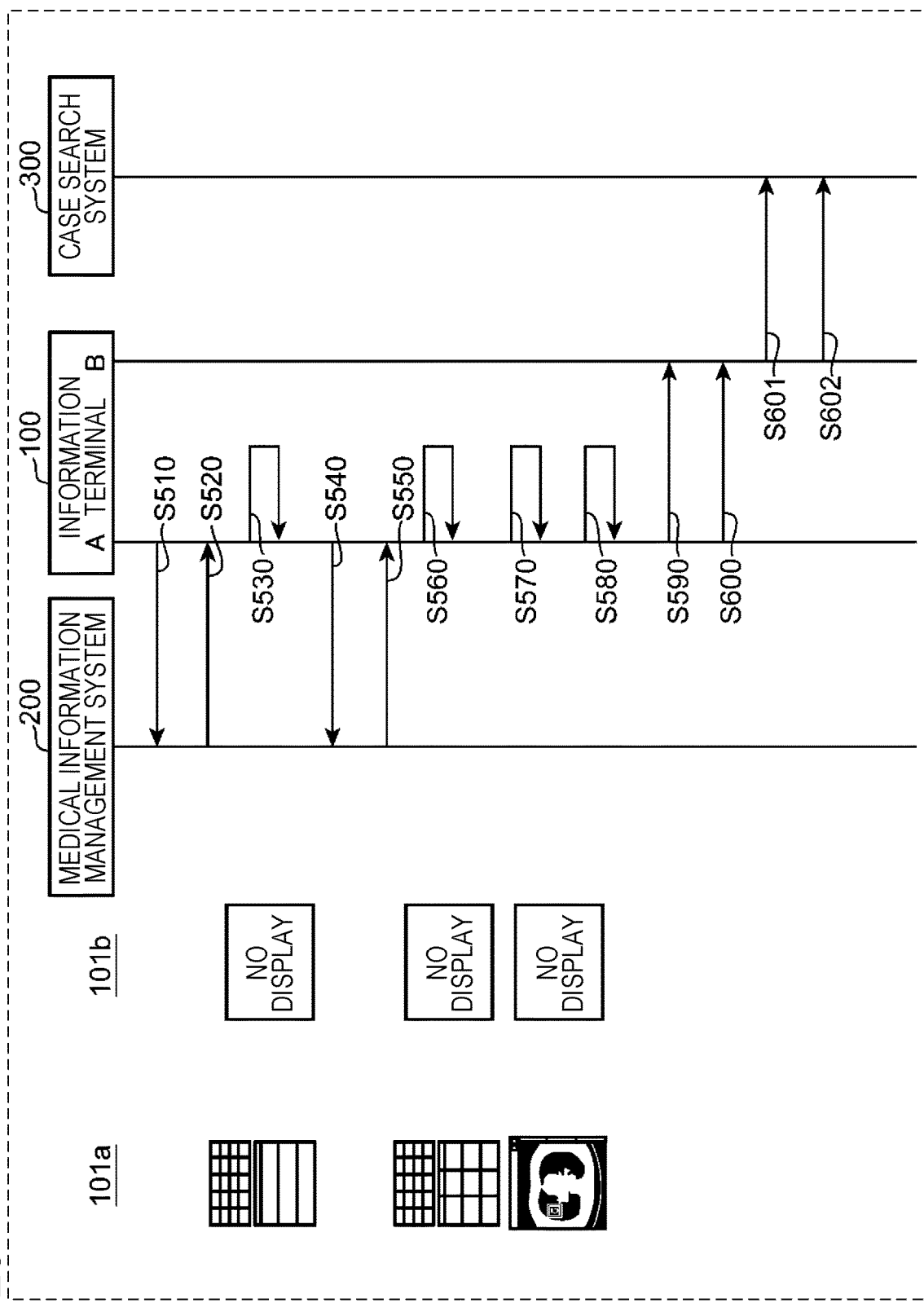
FIG. 23 is a sequence diagram illustrating a process in which an information terminal acquires a case to be diagnosed from a medical information management system and issues a similar case search request to a case search system, and the case search system receives the similar case search request.

FIG. 23 is a sequence diagram illustrating a process in which the information terminal 100 acquires a case to be diagnosed from the medical information management system 200 and issues a similar case search request to the case search system 300, and the case search system 300 receives the similar case search request. Note that in FIG. 23, the rectangles in the two columns to the left of the sequence diagram illustrate the screens displayed on the displays 101a and 101b by the processes in the corresponding steps. Also, in FIG. 23, "A" in the information terminal indicates the medical information management application, while "B" indicates the similar case search application. Herein, it is supposed that the medical information management application has been launched in advance before the sequence is started.

First, the information terminal 100 receives, via the operating unit 102, an examination list display request for displaying a list of examinations to be interpreted by the user (the physician performing radiological interpretation), and transmits, via the input controller 103 and the communication controller 110, the examination list display request to the communication controller 206 of the medical information management system 200 (S510).

The patient information manager 202 of the medical information management system 200 lists examinations for which image scanning has been performed but for which interpretation is unfinished, and generates an examination list of examinations to be interpreted. Subsequently, the patient information manager 202 transmits, via the communication controller 206, the generated examination list to the communication controller 110 of the information terminal 100 (S520). Herein, the examination list includes the patient information 1000 and the examination information 1800 of one or more relevant patients.

The display controller 104 of the information terminal 100 displays the examination list received by the communication controller 110 on the display 101 (S530).

In this case, the examination list is displayed on the display 101a, while nothing is displayed on the display 101b.

FIG. 24 is a diagram illustrating an examination list screen. The examination list includes an area 800 displaying examinations for which interpretation is unfinished, and an area 810 displaying information related to series included in an examination. In the area 800, the fields "Patient ID", "Patient Name", "Examination Date", "Examination ID", and "Examination Type" are provided. In the "Patient ID" and "Patient Name" fields, the patient ID 1100 and the name 1200 registered in the patient information 1000 are displayed, while in the "Examination Date", "Examination ID", and "Examination Type" fields, the examination date 1820, the examination ID 1810, and the examination type 1830 registered in the examination information 1800 are displayed. The area 810 is for displaying the details of an examination selected by the user in the area 800, and is provided with the fields "Series ID", "Definition", and "Image". At this point, since the user has not selected an examination (corresponding to a row) in the area 800, nothing is displayed in the area 810.

The user selects to examination to interpret next from among the examinations displayed in the area 800. After this selection is sensed by the input controller 103, as illustrated in FIG. 23, the communication controller 110 transmits a request to display all series included in the examination ID of the selected examination to the medical information management system 200 (S540).

After the communication controller 206 of the medical information management system 200 receives the display request, the patient information manager 202 references the medical image database 2000 illustrated in FIG. 18A, acquires all slice images in all series included in the examination ID specified by the display request, and transmits the acquired slice images to the information terminal 100 via the communication controller 206 (S550). For example, in the example of FIG. 18A, if the examination with the examination ID "13227989" is selected by the user, all slice images included in the series with the series IDs "CT149123" and "CT149124" are transmitted in S550.

After the communication controller 110 of the information terminal 100 acquires the images in all series, the display controller 104 displays, in the area 810, a series list that lists information related to all series included in the specified examination ID (S560).

In this case, a series list of the series corresponding to the examination selected in the area 800 is displayed in the area 810 of the examination list displayed on the display 101a, while nothing is displayed on the display 101b.

FIG. 25 is a diagram illustrating an examination list screen after an examination is selected. A highlight is applied to the background of the row selected in the area 800 of FIG. 25. In the example of FIG. 25, in the area 800, the examination of "Pana, Taro" on the second row is selected. For this reason, in the area 810, "Series ID", "Definition", and "Image" are displayed for the selected examination. Herein, in the "Series ID" field, the series IDs associated with the examination ID of the selected examination in the medical image database 2000 are displayed, while in the "Image" field, a thumbnail image of one slice image representative of each displayed series ID is displayed. Herein, an image at a certain slice position is adopted as the one slice image representative of each series ID. The certain slice position may be the first slice position or a central slice position. "Definition" indicates the imaging condition and the reconstruction condition for the relevant series. This "Definition", although omitted from illustration, is registered in association with the series ID in the medical image database 2000 of FIG. 18A, for example.

Figure 49:
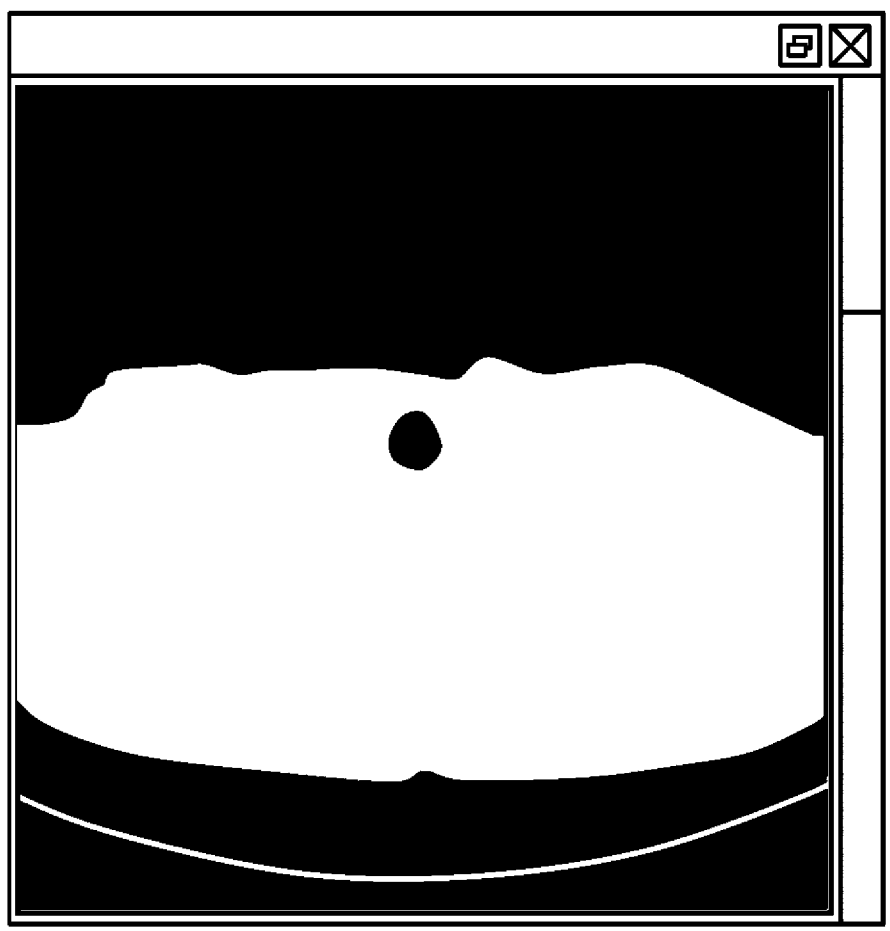
FIG. 49 is a diagram illustrating a slice image displayed on a display when a series is selected by a user.

In the area 810, a series to be interpreted is selected by the user, and after the input controller 103 senses this selection, the display controller 104 displays the first slice image of the selected series on the display 101*a*, as illustrated in FIG. 49 (S570). FIG. 49 is a diagram illustrating a slice image displayed on the display 101*a* when a series is selected by the user. FIG. 49 is a diagram illustrating the first slice image in a chest CT scan, and is a slice image at a shoulder position slightly closer to the head than the apical portion of the lungs. At this point, the display controller 104 displays the slice images on the display 101*a* in a state allowing all slice images in the selected series to be cycled through. Note that nothing is displayed on the display 101*b*. For example, the user inputs a slice-cycling operation of rotating the mouse wheel while the mouse pointer is positioned over the display 101*a*, and the input controller 103 senses this operation. Subsequently, the display controller 104 switches the slice image displayed on the display 101*a* to a slice image at another slice position, according to the amount of rotation of the mouse wheel. The user makes an image diagnosis while inputting slice-cycling operations. Additionally, if the user is having difficulty making an image diagnosis, the user launches the similar case search application.

At this point, the similar case search application may be launched by inputting a predetermined shortcut key on the keyboard of the operating unit 102, or a menu of the medical image viewer may be displayed with a right-click of the mouse, and the similar case search application may be launched by specifying a similar case search menu item from the menu. After an instruction to launch the similar case search application is given, the management of the information terminal 100 is passed to the ROI manager 105, and the information terminal 100 enters a standby state waiting to receive a region of interest (ROI).

Figure 26:
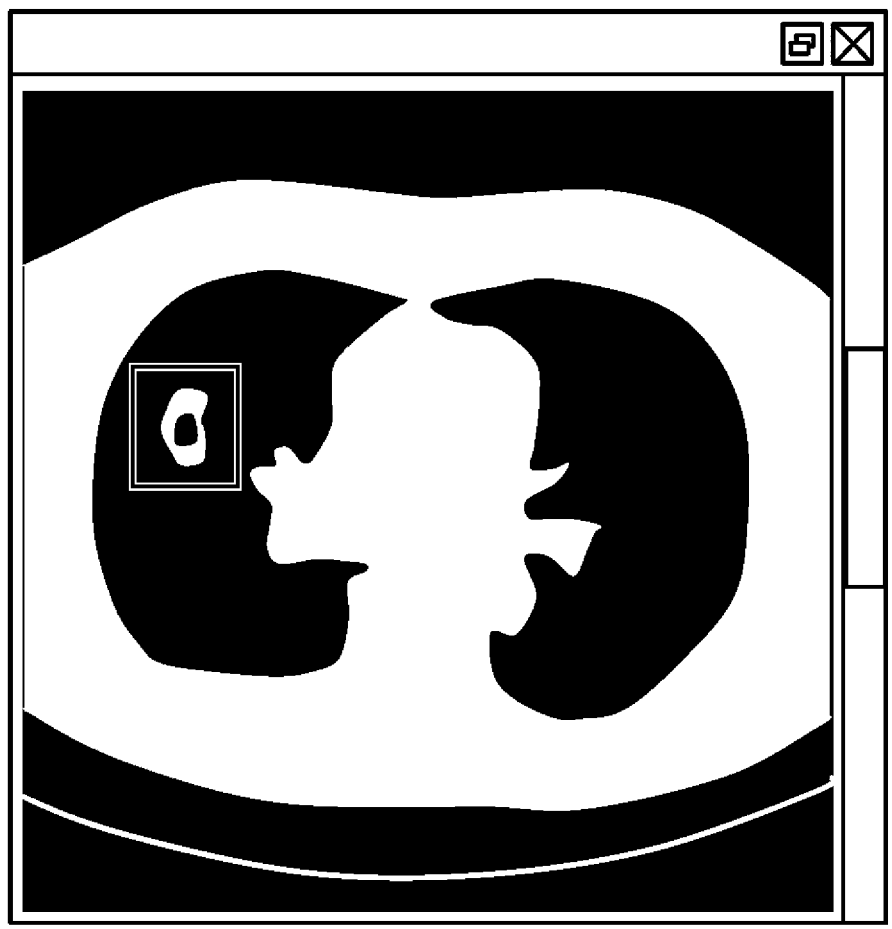
FIG. 26 is a diagram illustrating a first example of a screen after a region of interest is set with respect to a lesion.

The user sets, via the operating unit 102, a region of interest (ROI) in a lesion on the slice image displayed on the display 101*a* (S580). At this point, as illustrated in FIG. 22, the user left-clicks the mouse to input the coordinates of the top-left vertex of the region of interest, for example. Subsequently, the user may input the bottom-right vertex of the region of interest by keeping the left-click button held down and dragging the mouse diagonally down and to the right, and then releasing the left-click button. FIG. 26 is a diagram illustrating a first example of a screen after a region of interest is set with respect to a lesion.

After the input controller 103 senses the operation setting the region of interest, the ROI manager 105 receives the coordinate data of the top-left and the bottom-right vertices of the region of interest from the input controller 103, and generates the received coordinate data as region of interest information. Subsequently, the ROI manager 105 transmits the generated region of interest information to the communication controller 110 (S590).

At the same time, the ROI manager 105 transmits the slice image of the case to be diagnosed to the communication controller 110 (S600). In this case, the ROI manager 105 transmits the one slice image with the region of interest set by the user (the search query image) in the series selected by the user from among the slice images of all series that the information terminal 100 received from the medical information management system 200 in S550.

Next, the communication controller 110 receives the region of interest information transmitted from the ROI manager 105, and transmits the region of interest information to the communication controller 304 of the case search system 300 (S601).

At the same time, the communication controller 110 receives the slice image transmitted from the ROI manager 105, and transmits the slice image to the communication controller 304 of the case search system 300 (S602).

At this point, in S600 and S601, the slice image itself is transmitted, but transmitting only the slice ID of the slice image is also acceptable. In this case, the case search system 300 receiving the slice ID may specify that slice ID to acquire the slice image from the medical information management system 200.

(Flow from Similar Case Search to Initial Display)

Next, the process by which the case search system 300 performs a similar case search and the information terminal 100 presents the initial display of the similar case search results will be described.

Figure 27:
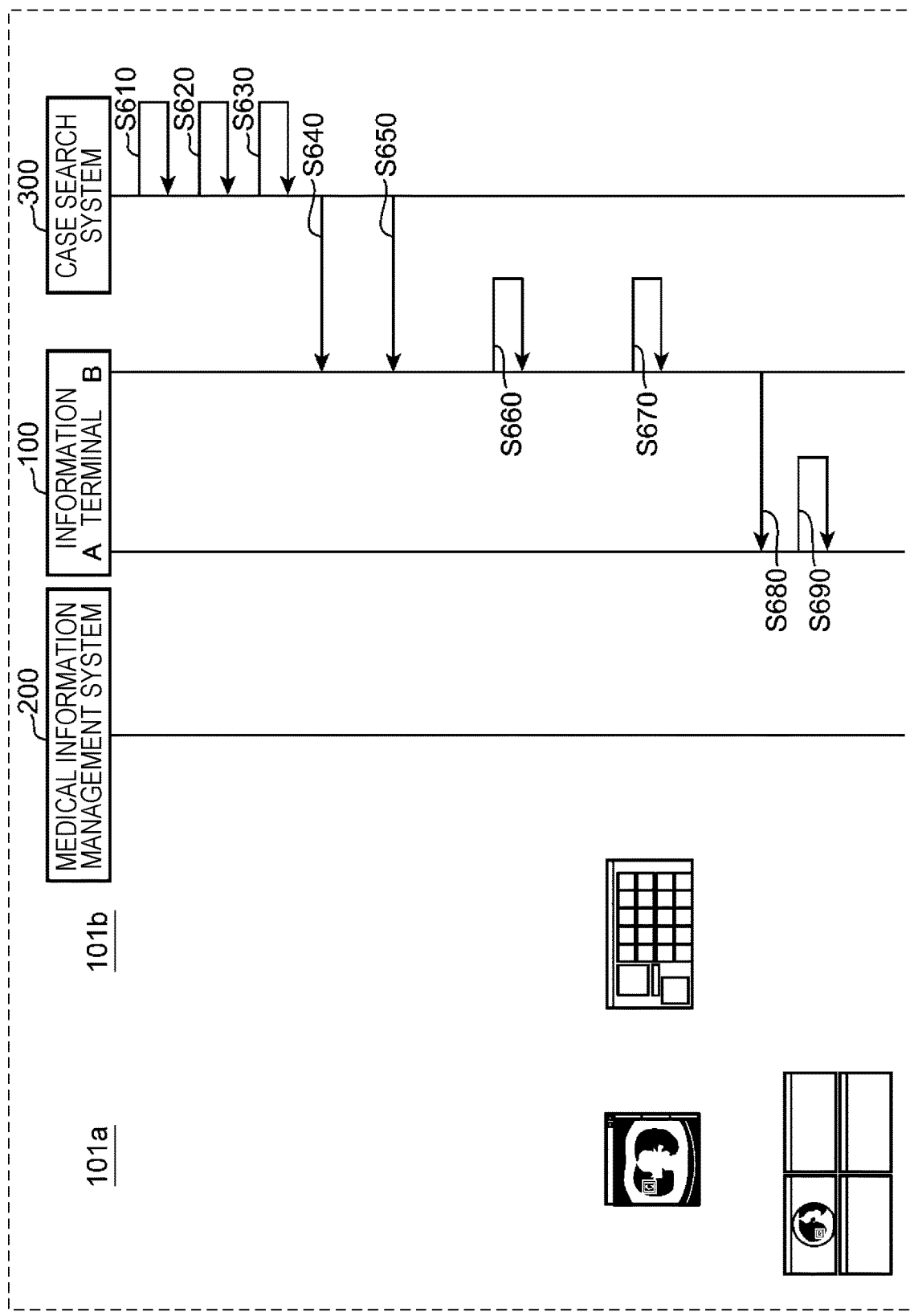
FIG. 27 is a sequence diagram illustrating a process in which a case search system receives a similar case search request, and replies to an information terminal with similar case search results.

FIG. 27 is a sequence diagram illustrating a process in which the case search system 300 receives a similar case search request, and replies to the information terminal 100 with similar case search results.

The image feature extractor 302 of the case search system 300 extracts predetermined, multidimensional image features from the region of interest set in the search query image (S610).

Image features related to the shape of the organ or the shape of the affected portion in the medical image, or image features related to a brightness distribution may be adopted as the image features. For example, the use of 490-dimension image features is described in the non-patent literature by Nemoto et al., "Improvement of Tumor Detection Performance in Mammograms by Feature Selection from a Large Number of Features and Proposal of Fast Feature Selection Method", The transactions of the Institute of Electronics, Information and Communication Engineers. D-II, Vol. J88-D-II, No. 2, pp. 416-426, February 2005. In the present embodiment, the image features described in the above non-patent literature are adopted, for example. However, this is merely one example, and other image features may also be adopted.

The similar case search unit 303 compares the image features extracted by the image feature extractor 302 to the image features of each similar case stored in the similar case data storage 301 (S620). At this point, the similar case search unit 303 compares image features by computing the distance between the image feature data extracted from the search query image and the image feature data 4400 registered in the similar case data 4000 (see FIG. 20) stored for each similar case in the similar case data storage 301.

Next, the similar case search unit 303 sorts similar cases having a distance less than or equal to a certain threshold value in order of shortest distance, and decides these similar cases as the similar cases to be transmitted (S630). Next, the communication controller 304 transmits the similar case data 4000 of the similar cases to be transmitted from among the similar case data 4000 stored in the similar case data storage 301 (S640).

Thereafter, a process of generating the initial basic screen K2 on which the similar case search results are displayed (see FIG. 6) is executed. First, the management information used when generating the layout area 720 on the initial basic screen K2 will be described.

First, the communication controller 304 of the case search system 300 transmits layout information to the information terminal 100 (S650). Herein, layout information is information specifying the number of rows and the number of columns of the display boxes constituting the layout area 720.

Next, after the communication controller 110 of the information terminal 100 receives the layout information, the display box manager 106 registers the number of rows and the number of columns of display boxes specified by the transmitted layout information in the display box management information 4410 (see FIG. 37), and also registers the slice ID of the search query image in the display box management information (see FIG. 37) (S660).

FIG. 37 is a diagram illustrating a data structure of the display box management information 4410. The display box management information 4410 includes a table 4411 in which the number of rows and the number of columns are registered, and a table 4412 in which the slice ID of the slice image displayed in each display box is registered. Consequently, the display box manager 106 registers the number of rows and the number of columns specified by the layout information transmitted from the case search system 300 in the "Number of Rows" and "Number of Columns" fields of the table 4411. Also, in the present embodiment, a thumbnail image of the search query image is displayed in the top-left display box 721 from among the four display boxes 721 to 724. Accordingly, the display box manager 106 registers the slice ID of the search query image transmitted from the medical information management system 200 in the "Row 1 Column 1" item of the table 4412.

Herein, default values for the number of rows and the number of columns of the display boxes constituting the layout area 720 are preset by the case search system 300. Herein, the default values for the number of rows and the number of columns is two rows and two columns, for example. For this reason, "2" rows and "2" columns are registered in the display box management information 4410 illustrated in FIG. 37.

Next, the display controller 104 uses the similar case data transmitted in S640 and the display box management information 4410 saved in S660 to generate the initial basic screen K2 on which the similar case search results are displayed (S670).

In this case, the basic screen K2 illustrated in FIG. 6 is displayed on the display 101b. Also, the search query image is displayed on the display 101a.

Figure 28:
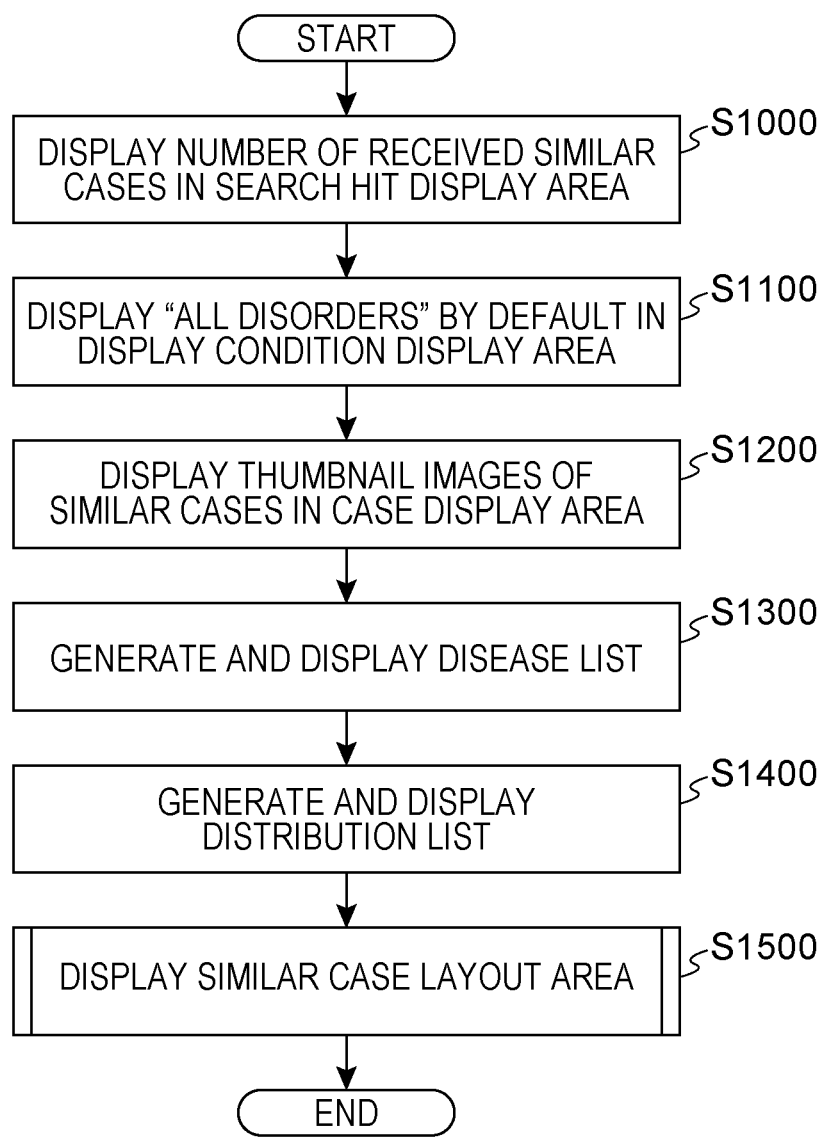
FIG. 28 is a flowchart illustrating details of a process of generating the initial basic screen illustrated in S670 of FIG. 27.

FIG. 28 is a flowchart illustrating details of a process of generating the initial basic screen K2 illustrated in S670 of FIG. 27.

First, in S1000, the display controller 104 counts the number of similar case data items received in S640 of FIG. 27, and displays the count value in the search hit display area 713.

Next, in S1100, the display controller 104 displays "All Disorders" in the display condition display area 714. At this point, "All Disorders" is displayed because on the initial basic screen K2, a filter by disease or lesion distribution has not been applied by the user.

Next, in S1200, the display controller 104 displays a number of thumbnail images of similar cases in the case display area 710 equal to the number of similar cases whose thumbnail images are displayable in the case display area 710 from among the similar cases corresponding to the similar case data received in S640 of FIG. 27. In addition, the display controller 104 displays the definite diagnosis and the similarity in correspondence with each of the thumbnail images.

The maximum number of similar cases displayable in the case display area 710 is 20 in the example of FIG. 6. This maximum value is predetermined. Also, the maximum value may be configured to be modifiable freely by the user. If the number of similar case data items received in S640 of FIG. 27 is greater than the maximum value, the display controller 104 displays the vertically elongated scrollbar 715 on the right side of the case display area 710. Consequently, the user is able to move the scrollbar 715 and view the thumbnail images of the similar cases that were hidden on the initial basic screen K2.

Next, in S1300, a disease list is generated and displayed. First, a disease list is generated from the similar case data received in S640 of FIG. 27. The disease list is a list in which the similar cases corresponding to the similar case data received in S640 are classified into the respective names of diseases according to the definite diagnosis.

At this point, suppose that NC is the number of cases of similar case data received in S640. The disease list manager 108 generates a disease list by using the definite diagnosis (major disease classification) 4700 and the definite diagnosis (fine disease classification) 4800 registered in each of the NC similar case data items 4000. The generated disease list is managed by the disease list manager 108 as data in a table format, as illustrated in FIG. 30.

FIG. 30 is a diagram illustrating a data structure of a disease list generated in S1300 of FIG. 28. The disease list includes "Disease ID", "Major Disease Classification", "Fine Disease Classification", "No. of Cases", and "Similar Case ID" fields. The "Disease ID" is an identifier assigned to each name of a disease according to a definite diagnosis. Herein, one disease ID is assigned to one combination of a major disease classification and a fine disease classification.

The "Major Disease Classification" is the name of the disease according to the definite diagnosis indicated by the definite diagnosis (major disease classification) 4700 registered in the similar case data 4000. The "Fine Disease Classification" is the name of the disease according to the definite diagnosis indicated by the definite diagnosis (fine disease classification) 4800 registered in the similar case data 4000. The "No. of Cases" is the number of similar cases corresponding to the name of the disease according to the definite diagnosis indicated by the "Disease ID". The "Similar Case IDs" are similar case IDs indicating similar cases corresponding to the disease indicated by the "Disease ID".

The disease list manager 108 extracts the definite diagnosis (major disease classification) 4700 and the definite diagnosis (fine disease classification) 4800 for all similar case data items 4000 received in S640, and classifies similar case data items 4000 having both of the same disease classifications as similar cases with the same disease according to the definite diagnosis. Subsequently, the disease list manager 108 counts the number of similar cases with the same disease according to the definite diagnosis, and registers the count in the "No. of Cases" field of the record for the corresponding disease according to the definite diagnosis. Additionally, the disease list manager 108 registers the similar case IDs of the similar cases classified into the same disease according to the definite diagnosis in the "Similar Case IDs" field of the record for the corresponding disease according to the definite diagnosis.

In the example of FIG. 30, the disease ID "DIS528" is assigned to the disease having the major disease classification "Neoplastic" and the fine disease classification "Lung Cancer" according to the definite diagnosis. Additionally, since there are 10 similar cases corresponding to this disease according to the definite diagnosis, 10 is registered in the "No. of Cases" field of the corresponding record, and similar case IDs such as "SIM258", "SIM551", "SIM1209", and "SIM2341" of similar cases corresponding to this disease according to the definite diagnosis are registered in the "Similar Case IDs" field of the corresponding record.

Subsequently, the display controller 104 uses the disease list generated in this way to generate and display the disease list display area 730 on the display 101.

FIGS. 31, 32, and 33 are diagrams illustrating a first display example, a second display example, and a third display example of the disease list display area 730, respectively. In the first display example as illustrated in FIG. 31, the similar cases obtained as a result of the similar case search are listed in association with the number of cases of the fine disease classification, in descending order by the number of cases.

In the second display example as illustrated in FIG. 32, the similar cases obtained as a result of the similar case search are listed in association with the number of cases of the major disease classification, in descending order by the number of cases.

In the third display example as illustrated in FIG. 33, the similar cases obtained as a result of the similar case search are listed in association with the number of cases of the major disease classification, in descending order by the number of cases, and additionally are listed in association with the fine disease classifications included in each of the major disease classifications, in descending order by the number of cases. In this case, the names of diseases according to the definite diagnosis are expressed in a hierarchical structure of a major disease classification and a fine disease classification.

Figure 34:
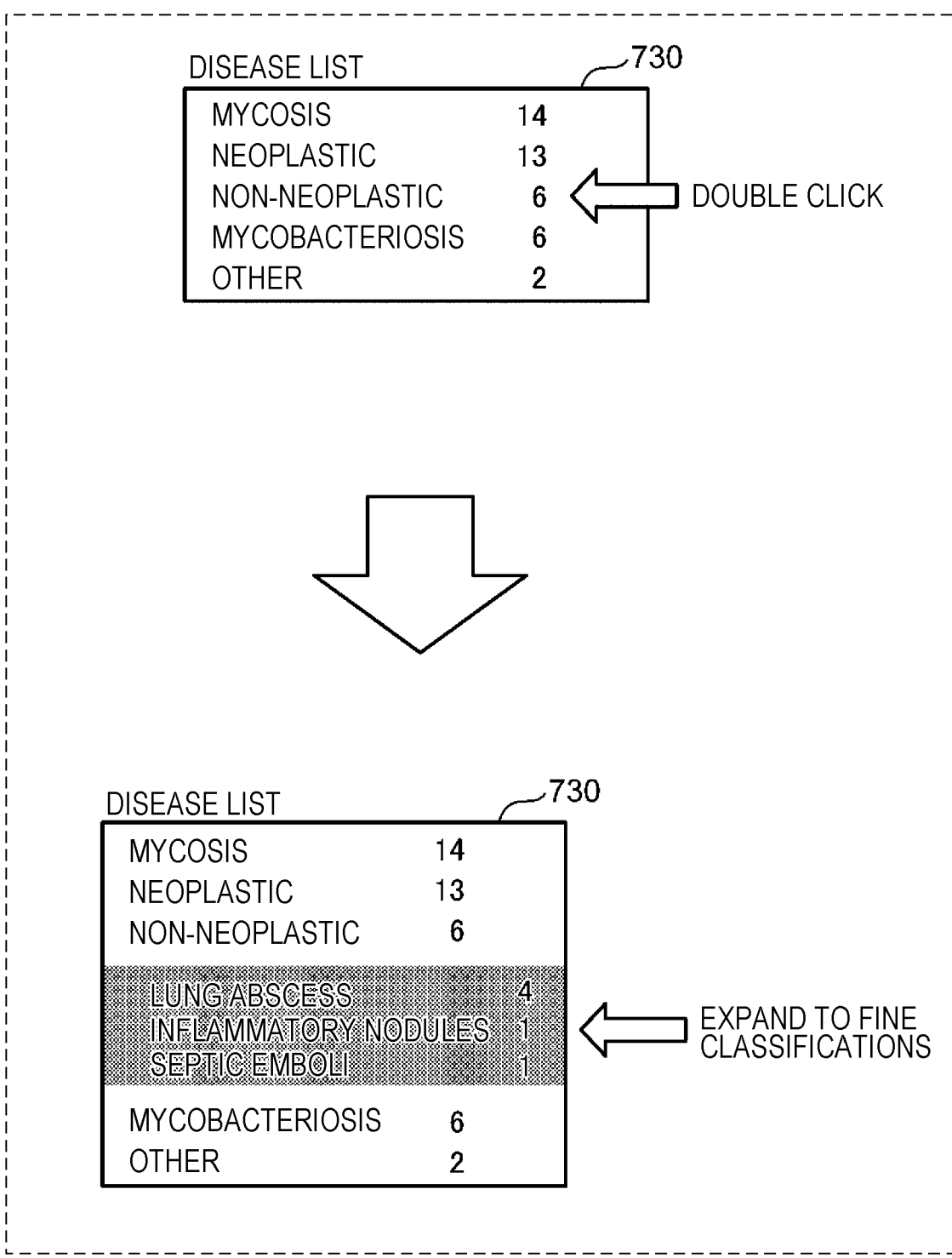
FIG. 34 is a diagram illustrating a screen transition of the disease list display area illustrated in FIG. 32.

FIG. 34 is a diagram illustrating a screen transition of the disease list display area 730 illustrated in FIG. 32. If the input controller 103 senses an operation of the user selecting one major disease classification from among the listed major disease classifications, as illustrated in the top part of FIG. 34, the display controller 104 displays the fine disease classifications belonging to the selected major disease classification in association with the number of cases in descending order, as illustrated in the bottom part of FIG. 34. At this point, the user may select a major disease classification by double-clicking or single-clicking the desired major disease classification from among the major disease classifications listed in the disease list display area 730, for example. In the example of FIG. 34, non-neoplastic has been doubled-clicked, and thus the fine disease classifications belonging to the non-neoplastic major disease classification are listed.

In the bottom part of FIG. 34, if the user double-clicks or single-clicks the area in which fine disease classifications are being listed, the display controller 104 may hide the fine disease classifications being displayed in the corresponding area.

Note that the display controller 104 may determine which fine disease classifications belong to which major disease classifications by referencing the disease list (see FIG. 30). For example, in the example of FIG. 30, since aspergillosis and cryptococcosis are associated with mycosis, the display controller 104 may determine that aspergillosis and cryptococcosis belong to mycosis.

Returning to FIG. 28, in S1400, a distribution list is generated and displayed. First, a distribution list is generated from the similar cases received in S640. The distribution list is a list in which the similar cases received in S640 are classified into respective lesion distributions.

The disease list manager 108 generates a distribution list by using the lesion distribution information 4600 registered in each of the NC similar case data items 4000. The generated distribution list is managed by the distribution list manager 109 as data in a table format, as illustrated in FIG. 35.

FIG. 35 is a diagram illustrating a data structure of the distribution list generated in S1400 of FIG. 28. The distribution list includes "Distribution Name", "No. of Cases", and "Similar Case IDs" fields. The "Distribution Name" is the names of multiple predetermined lesion distributions, such as diffuse and segmental. The "No. of Cases" is the number of similar cases corresponding to the lesion distribution. The "Similar Case IDs" are similar case IDs indicating similar cases corresponding to the lesion distribution.

The distribution list manager 109 extracts the lesion distribution information 4600 for all similar case data items 4000 received in S640, counts the number of lesion distributions for which the distribution flag value is set to 1 (applicable) in the extracted lesion distribution information 4600, and registers the count value in the "No. of Cases" of the record for the corresponding lesion distribution. Additionally, the distribution list manager 109 registers the similar case IDs of the similar cases in which the distribution flag value is set to 1 in the "Similar Case IDs" field of the record for the corresponding lesion distribution.

In the example of FIG. 35, there are three similar cases corresponding to the diffuse lesion distribution, and thus "3" is registered in the "No. of Cases" field of the record for "Diffuse". Also, the similar case IDs "SIM2521", "SIM4123", and "SIM5225" of similar cases corresponding to the diffuse lesion distribution are registered in the "Similar Case IDs" field of the record for "Diffuse".

Subsequently, the display controller 104 uses the distribution list generated in this way to generate and display the distribution list display area 750 on the display 101.

The distribution list display area 750 generated using the distribution list illustrated in FIG. 35 is as illustrated in FIG. 11. In FIG. 35, since the number of segmental and subpleural cases is 0, in FIG. 11, Segmental 752 and Subpleural 756 are displayed in an inactive state, whereas since the number of cases is at least 1 for the other lesion distributions, the other lesion distributions are displayed in an active state.

Returning to FIG. 28, in S1500, the layout area 720 is displayed. This process is conducted by the display controller 104.

Figure 29:
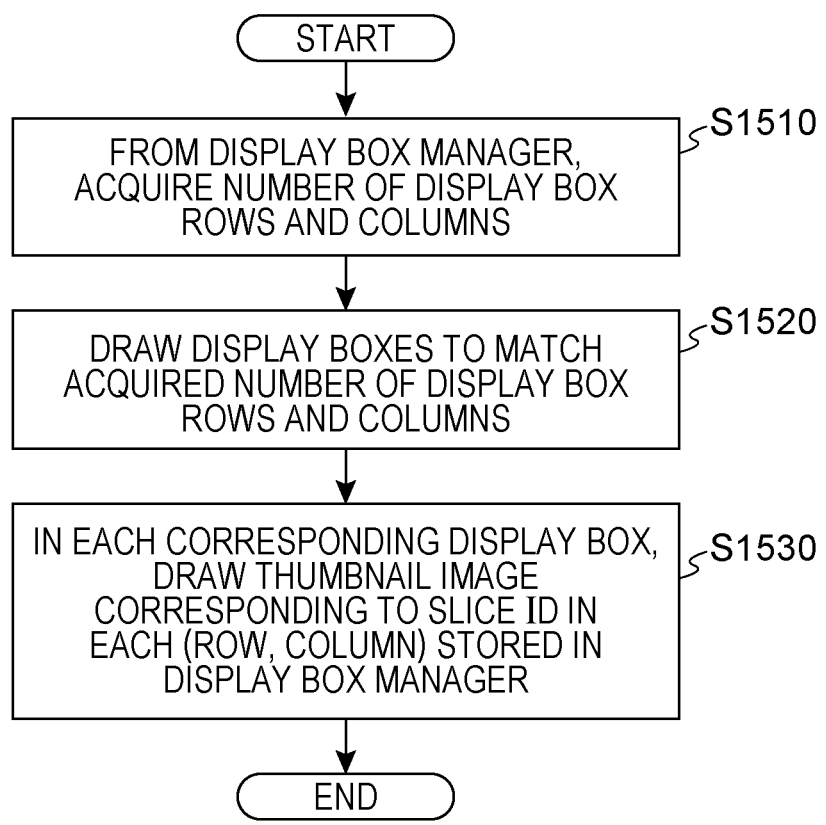
FIG. 29 is a flowchart illustrating the process of S1500 illustrated in FIG. 28.

FIG. 29 is a flowchart illustrating the process of S1500 illustrated in FIG. 28. In S1510, the display controller 104 acquires, from the display box management information 4410 set in S660, the number of rows and the number of columns of the display boxes constituting the layout area 720. In the example of the display box management information 4410 in FIG. 37, the number of rows and the number of columns are set to 2×2, and thus the information "2×2" is acquired.

Next, in S1520, the display controller 104 draws display boxes matching the number of rows and the number of columns of display boxes acquired in S1510.

Finally, in S1530, the display controller 104 specifies the slice ID of each display box from the display box management information 4410, and draws the thumbnail image corresponding to each specified slice ID inside each corresponding display box.

In the example of FIG. 37, the slice ID of the case to be diagnosed is stored in the display box in row 1 column 1. For this reason, the display controller 104 generates a thumbnail image from the slice image of the case to be diagnosed transmitted in S600 of FIG. 23, and draws the generated thumbnail image in the display box 721.

At this stage, slice IDs are not stored in the remaining display boxes (the display boxes 722, 723, and 724 in row 1 column 2, row 2 column 1, and row 2 column 2, respectively), and thus the display controller 104 does not display anything in these display boxes. Thumbnail images of similar cases will be displayed in these display boxes by a process discussed later.

Returning to FIG. 27, the communication controller 110 transmits the display box management information 4410 stored in the display box manager 106 to the display controller 104 (S680).

Next, the display controller 104 launches medical image viewers in the same display state and layout as the display state and layout of the layout area 720 (S690).

Figure 38:
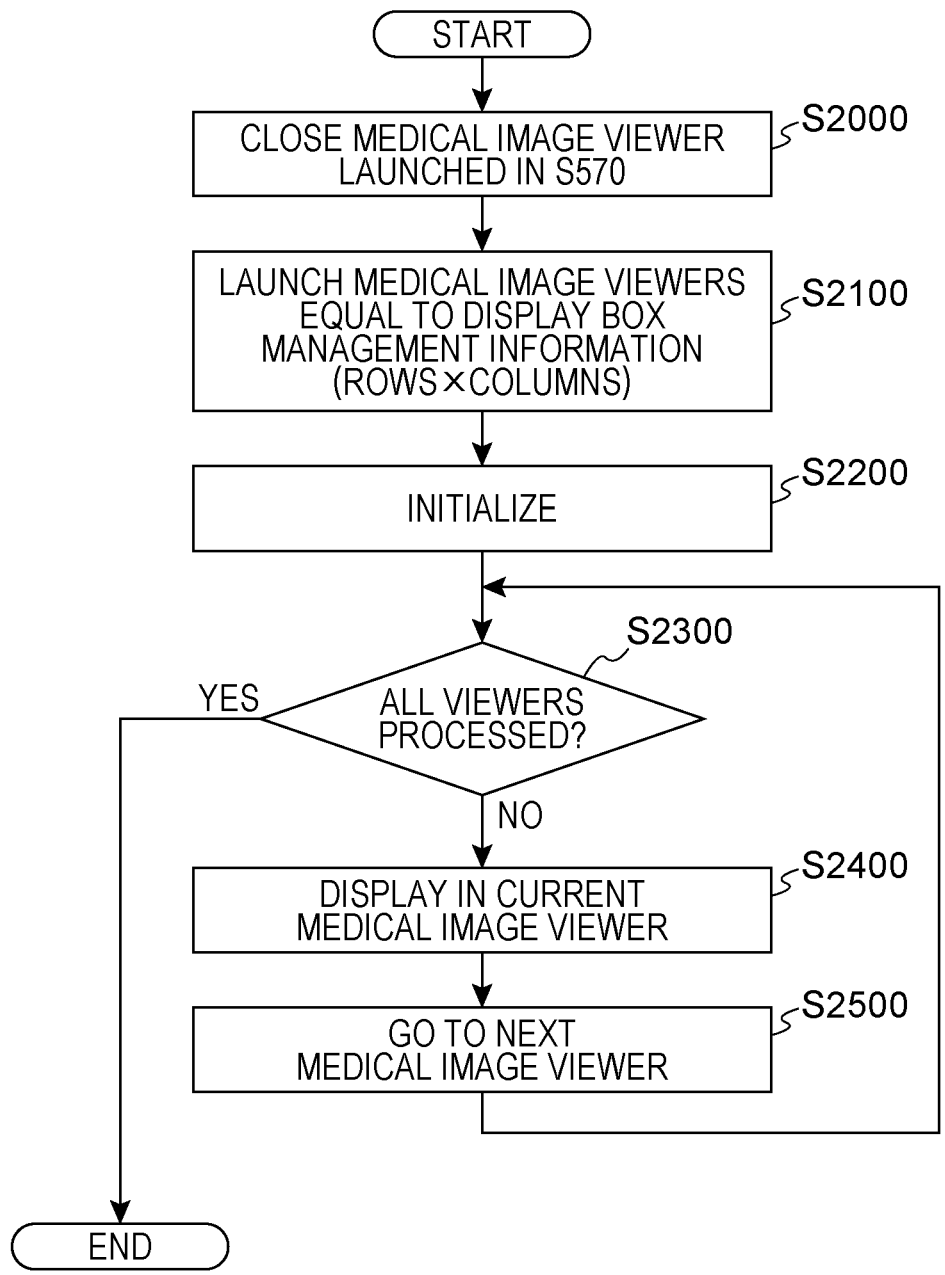
FIG. 38 is a flowchart illustrating a medical image viewer launching process.

FIG. 38 is a flowchart illustrating a medical image viewer launching process.

In S2000, the display controller 104 closes the medical image viewer launched in S570 of FIG. 23.

In S2100, the display controller 104 launches medical image viewers equal to the number of display boxes registered in the display box management information 4410, in the layout of the number of rows and the number of columns registered in the display box management information 4410. In the display box management information 4410 of FIG. 37, four display boxes in a 2×2 layout are registered. Thus, the display controller 104 launches four medical image viewers 610 to 640 in a 2×2 layout, as illustrated in FIG. 5.

In S2200, the display controller 104 initializes a variable for specifying the medical image viewer currently being processed. At this point, since the medical image viewer in row 1 column 1 is currently being processed, the variable is set to row 1 column 1.

In S2300, the display controller 104 checks whether or not all (in this case, four) medical image viewers have been processed. If all have been processed (S2300, Yes), the process ends, whereas if an unprocessed medical image viewer exists (S2300, No), the process proceeds to S2400.

In S2400, the display controller 104 displays, in the medical image viewer currently being processed, the slice image having the slice ID associated with the row number and the column number set as the variable, and associates the series including that slice ID with the current medical image viewer.

For example, in the example of the display box management information 4410 illustrated in FIG. 37, the slice ID "CT12353515" is registered in row 1 column 1. Thus, the slice image having the slice ID "CT12353515" is displayed in the medical image viewer 610. In addition, the display controller 104 draws a rectangle representing the region of interest set in the initially displayed slice image overlaid on top of the slice image. Note that the series including the slice ID registered in row 1 column 1 was acquired already in S550 of FIG. 23. Also, the region of interest was set already in S580 of FIG. 23.

Returning to FIG. 38, in S2500, the next medical image viewer is set as the medical image viewer currently being processed. The processing target is set so that after row 1 column 1, row 1 column 2 is set next, then row 2 column 1, and then row 2 column 2 next, for example.

In S2400 of the second loop, the medical image viewer 620 in row 1 column 2 is being processed, but in the display box management information 4410 of FIG. 37, slice IDs are not associated elsewhere than row 1 column 1. For this reason, the display controller 104 does not execute any processing on the medical image viewer in row 1 column 2, and leaves the medical image viewer in a blank state. This is also the same for the medical image viewers 630 and 640 in row 2 column 1 and row 2 column 2.

After the flowchart is finished, the basic screen K1 in the initial state illustrated in FIG. 5 is displayed on the display 101a. The search query image is displayed in the medical image viewer 610 in row 1 column 1 (top-left), and the region of interest is drawn overlaid on top of the search query image.

Figure 39:
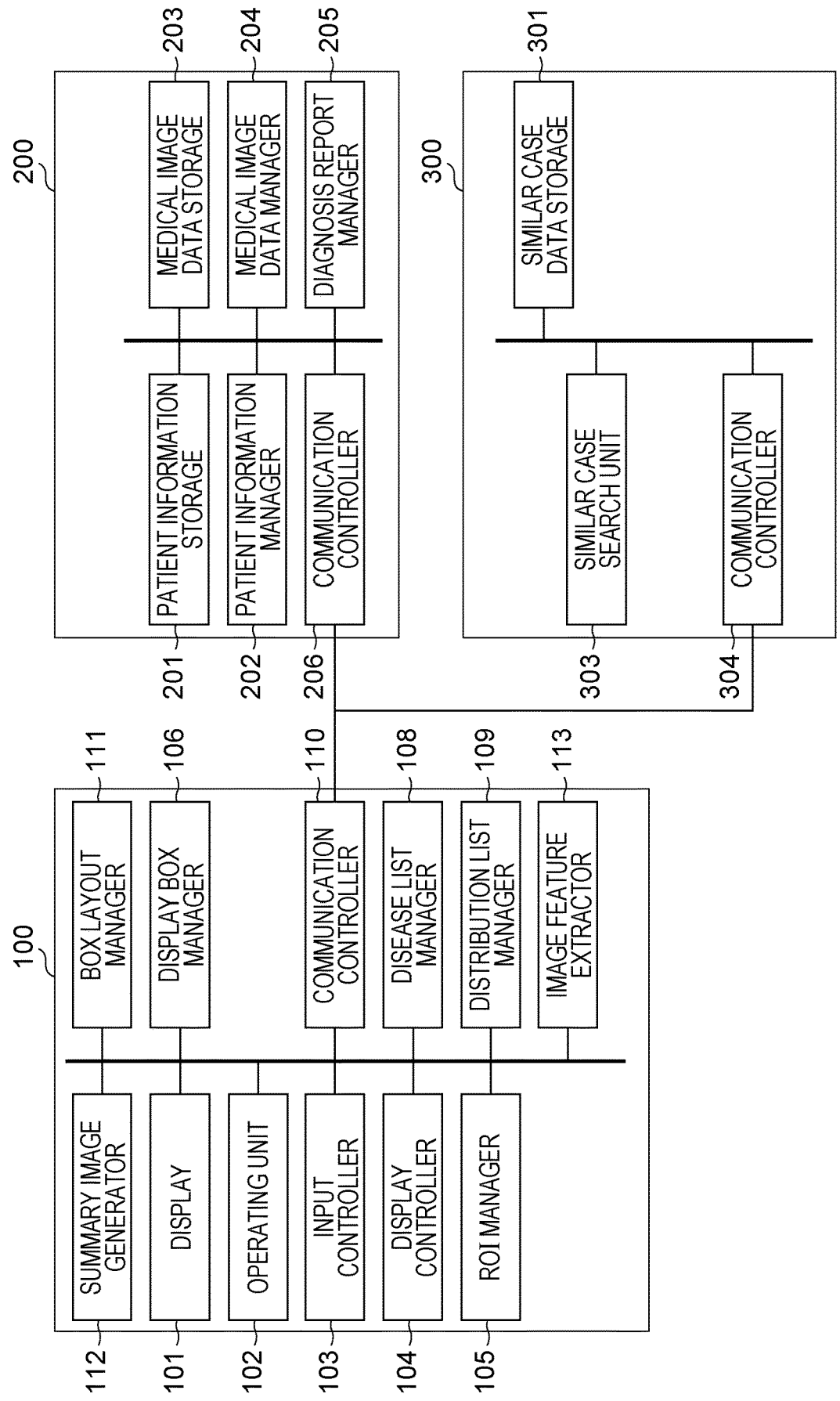
FIG. 39 is a block diagram of an information terminal, a medical information management system, and a case search system in a case of adopting an aspect in which the information terminal extracts image features.

Herein, an example of the case search system 300 extracting image features is illustrated, but the information terminal 100 may also extract image features. FIG. 39 is a block diagram of the information terminal 100, the medical information management system 200, and the case search system 300 in a case of adopting an aspect in which the information terminal 100 extracts image features.

FIG. 39 differs from FIG. 2 in that an image feature extractor 113 has been added to the information terminal 100, and the image feature extractor 302 has been omitted from the case search system 300.

Figure 40:
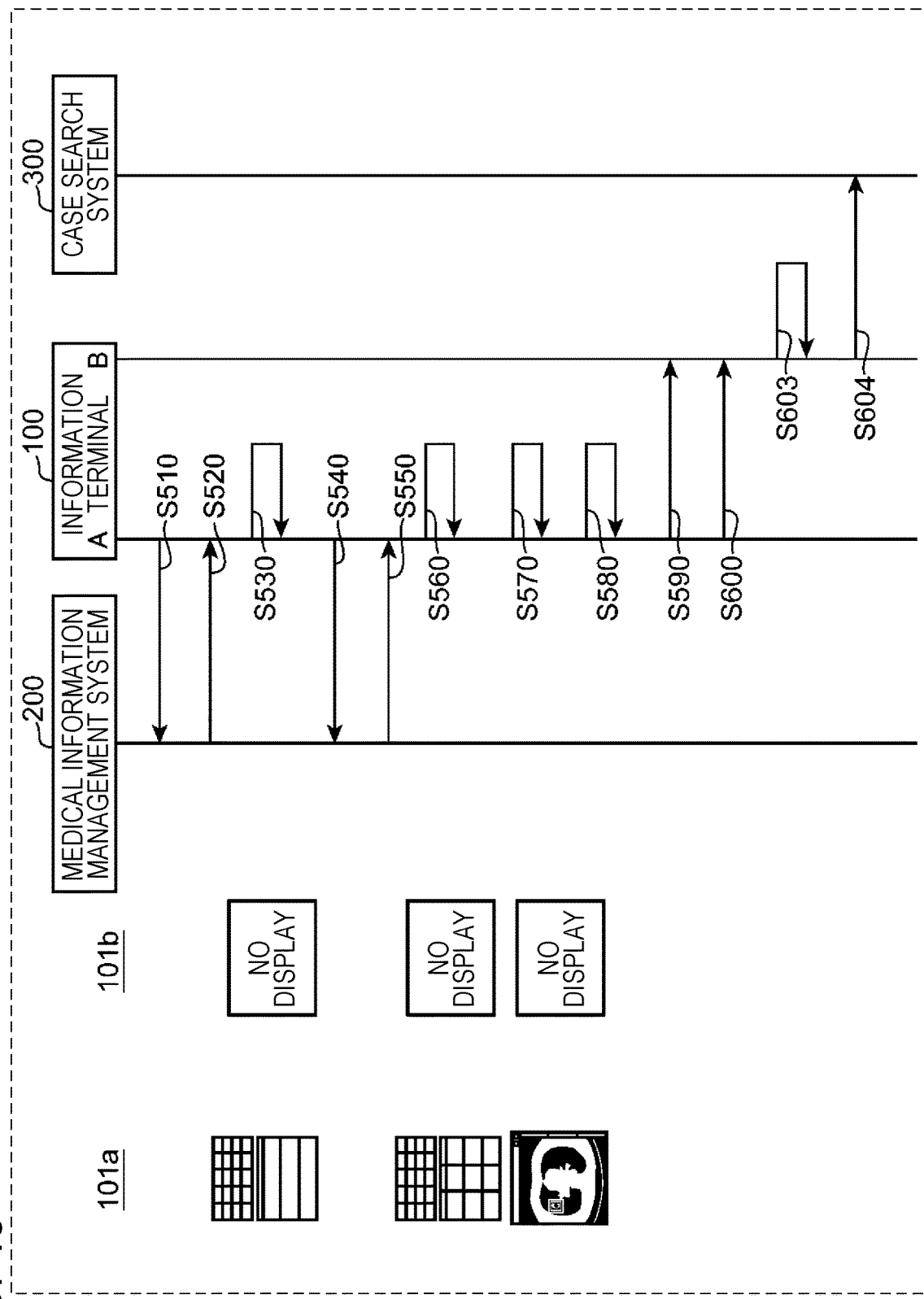
FIG. 40 is a sequence diagram illustrating a process in which an information terminal acquires a case to be diagnosed from a medical information management system, and a case search system receives a similar case search request.

FIG. 40 is a sequence diagram illustrating a process in which the information terminal 100 acquires a case to be diagnosed from the medical information management system 200, and the case search system 300 receives a similar case search request.

FIG. 40 differs from FIG. 23 in that, after the process of the ROI manager 105 transmitting the slice image of the case to be diagnosed to the communication controller 110 (S600), image feature extraction is conducted on the information terminal 100 (S603), and the extracted image features are transmitted to the case search system 300 (S604). The processing details of the image feature extraction (S604) is similar to the case in which image feature extraction is conducted on the case search system 300.

Figure 41:
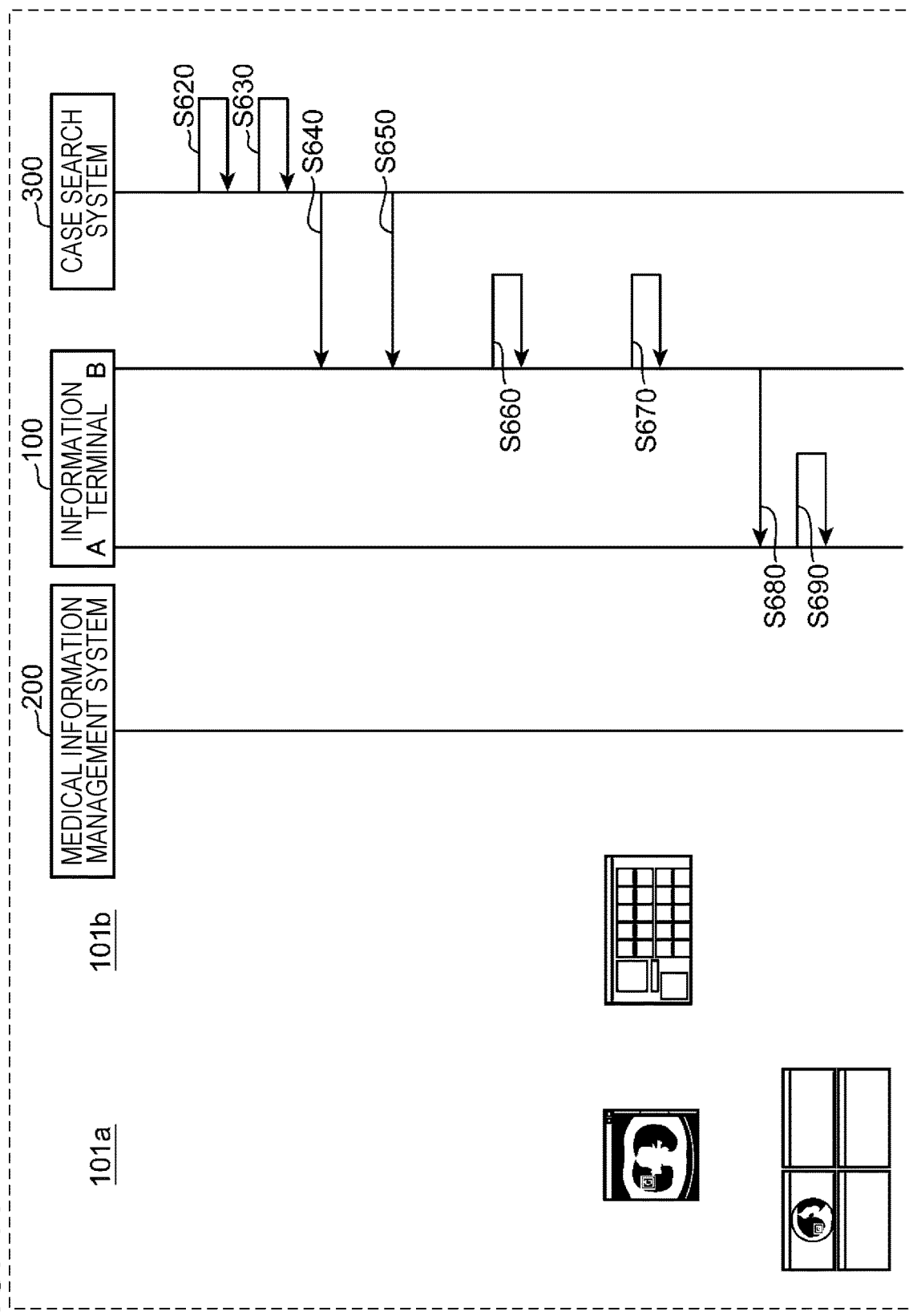
FIG. 41 is a sequence diagram illustrating a process in which a case search system receives a similar case search request, and replies to an information terminal with similar case search results.

FIG. 41 is a sequence diagram illustrating a process in which the case search system 300 receives a similar case search request, and replies to the information terminal 100 with similar case search results. FIG. 41 differs from FIG. 27 in that, since the image feature extraction is conducted on the information terminal 100, the image feature extraction (S610) illustrated in FIG. 27 is omitted from FIG. 41.

Figure 42:
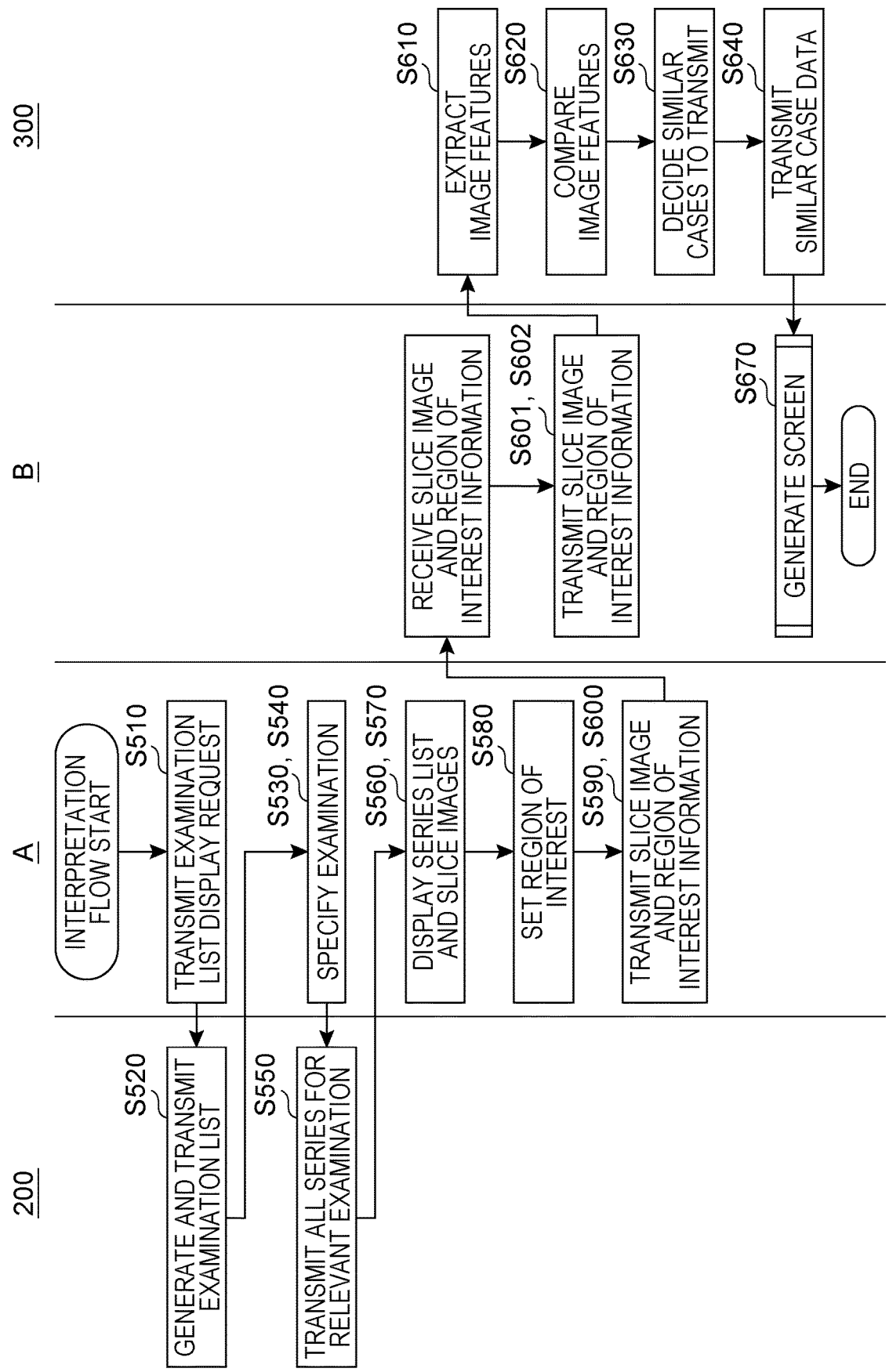
FIG. 42 is a sequence diagram for when the sequence diagrams in FIGS. 23 and 27 are focused on the application level.

Next, processes by the information terminal 100, the medical information management system 200, and the case search system 300 when interpreting the sequence diagrams in FIGS. 23 and 27 on the application level will be described. FIG. 42 is a sequence diagram for when the sequence diagrams in FIGS. 23 and 27 are focused on the application level. In FIG. 42, the same processes as in FIG. 23 are denoted with the same signs.

In FIG. 42, "A" indicates processes by the medical information management application executed by the information terminal 100, while "B" indicates processes by the similar case search application executed by the information terminal 100. Hereinafter, the medical information management application will be designated "Application A", while the similar case search application will be designated "Application B".

First, Application A receives from the user a request to display an examination list of examinations to be interpreted, and transmits the request to the medical information management system 200 (S510). After receiving the examination list display request, the medical information management system 200 lists examinations for which image scanning has been performed but for which interpretation is unfinished, generates an examination list of examinations to be interpreted, and transmits the generated examination list to Application A.

Upon receiving the examination list, Application A displays the examination list on the display 101 as illustrated in FIG. 24, and if one examination from the examination list is selected by the user (S530), Application A transmits a request to display the selected examination to the medical information management system 200 (S540).

Upon receiving the examination request, the medical information management system 200 transmits to Application A all slice images of all series included in the examination ID specified by the display request (S550).

Next, as illustrated in FIG. 25, Application A displays a series list that lists information related to all series included in the specified examination ID (S560).

Next, if a series to be interpreted from the series list is selected by the user, Application A displays the slice image in the first slice position of the selected series in the medical image viewer 610 (S570). At this point, the user inputs a slice-cycling operation to display a desired slice image in the medical image viewer 610.

Next, Application A receives from the user an operation of setting a region of interest in the slice image displayed in the medical image viewer 610 (S580).

Next, Application A generates region of interest information indicating the region of interest set by the user, and transmits generated region of interest information together with the slice image in which the region of interest is set (the slice image of the case to be diagnosed) to Application B (S590, S600).

Next, Application B, after receiving the slice image of the case to be diagnosed and the region of interest information, transmits the slice image and the region of interest information to the case search system (S601, S602).

After receiving the slice image and the region of interest information, the case search system 300 executes the processes from S610 to S640, similar to FIG. 27.

Next, Application B uses the similar case data transmitted in S640 and the display box management information 4410 to generate an initial basic screen (S670). Subsequently, Application B executes the processes of S670 illustrated in detail in FIG. 28.

(Flow from Initial Display to Thumbnail Selection)

Next, the flow of the process after similar case search results are displayed initially on the information terminal 100, in which the user selects a thumbnail image of a similar case search result on the information terminal 100, and a summary image corresponding to the selected thumbnail image is displayed, will be described.

Figure 53:
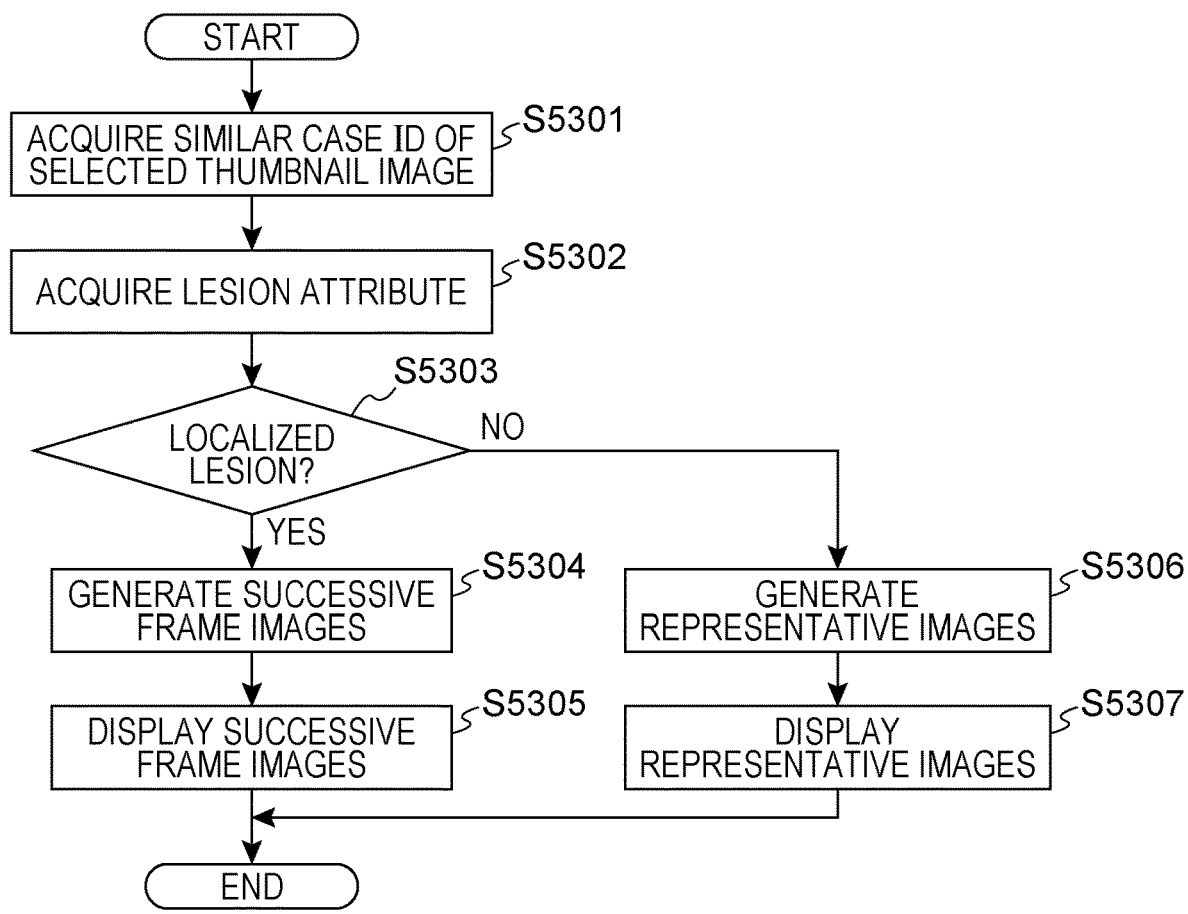
FIG. 53 is a flowchart of a summary image generation process.

FIG. 53 is a flowchart illustrating the flow of the process after similar case search results are displayed initially on the information terminal 100, in which a summary image corresponding to a thumbnail image selected by the user (summary image generation process).

(S5301)

The summary image generator 112 acquires the similar case ID 4100 of a thumbnail image selected by the user from among the thumbnail images of similar cases displayed in the case display area 710.

(S5302)

The summary image generator 112 references the similar case data 4000 of the thumbnail image selected by the user from the similar case ID 4100 acquired in S5301, and acquires the lesion attribute 4900.

(S5303)

If the lesion attribute 4900 acquired in S5302 indicates a localized lesion (S5303, Yes), the summary image generator 112 proceeds to S5340, whereas if the lesion attribute acquired in S5302 indicates a diffuse lesion (S5303, No), the summary image generator 112 proceeds to S5306.

(S5304)

The summary image generator 112 uses the similar case ID 4100 acquired in S5301 and the lesion attribute 4900 acquired in S5302 to generate successive frame images 717, and proceeds to S5305.

Specific methods of generating the successive frame images 717 are illustrated below.

(Successive Frame Image Generation Method 1)

Successive frame image generation method 1 is a method of generating the successive frame images 717 by using the slice IDs registered in the summary images 4910 of the similar case data 4000. In this case, it is sufficient to adopt the similar case data 4000 illustrated in FIG. 21A as the similar case data 4000. The summary image generator 112 references the similar case data 4000 corresponding to the similar case ID 4100 acquired in S5301, acquires the slice IDs registered in the summary images 4910, and acquires the thumbnail images corresponding to the acquired slice IDs from the medical information management system 200. Subsequently, the summary image generator 112 uses the acquired thumbnail images to generate the successive frame images 717.

Note that the medical information management system 200 may also create in advance thumbnail images for all slice IDs being managed, or alternatively, when a request to acquire thumbnail images corresponding to slice IDs is received from the summary image generator 112, the medical information management system 200 may generate thumbnail images corresponding to the relevant slice IDs. Subsequently, the medical information management system 200 may transmit the requested thumbnail images corresponding to the slice IDs to the information terminal 100. This also applies similarly to the successive frame generation methods and the representative image generation methods indicated below.

Herein, in the summary images 4910 of the similar case data 4000 illustrated in FIG. 21A, the slice IDs of slice images that successively illustrate from one end to another end of a localized lesion are registered. For this reason, the successive frame images 717 include thumbnail images corresponding to slice images from one end to another end of a localized lesion. Thus, by successively displaying the successive frame images 717, the thumbnail images illustrating from one end to another end of a localized lesion are displayed successively, and images of the abnormal shadow portion are displayed successively. As a result, the user is able to check information relevant to the diagnosis of a localized lesion, such as the three-dimensional shape of the affected area, and whether or not the affected area exists along the directions of blood vessels and the bronchi.

As a numerical value included in each slice ID included among the multiple slice IDs corresponding to one series ID becomes larger, the tomographic planes of the slice images specified by each slice ID may be taken to move in one direction of the patient's body.

The thumbnail images correspond to slice images, which are cross-sectional images of the patients body, and the order in which the thumbnail images are displayed may be the same as the order in which the tomographic planes of the slice images corresponding to each slice ID move in one direction of the patient's body as the numerical value included in each slice ID corresponding to each slice image becomes larger.

(Successive Frame Image Generation Method 2)

Successive frame image generation method 2 is a method of generating the successive frame images 717 by acquiring a certain number of adjacent thumbnail images including the thumbnail image selected by the user. The summary image generator 112 references the similar case data 4000 corresponding to the similar case ID 4100 acquired in S5301, and acquires a certain number of adjacent thumbnail images including the thumbnail image indicated by the slice ID 4200.

Figure 54:
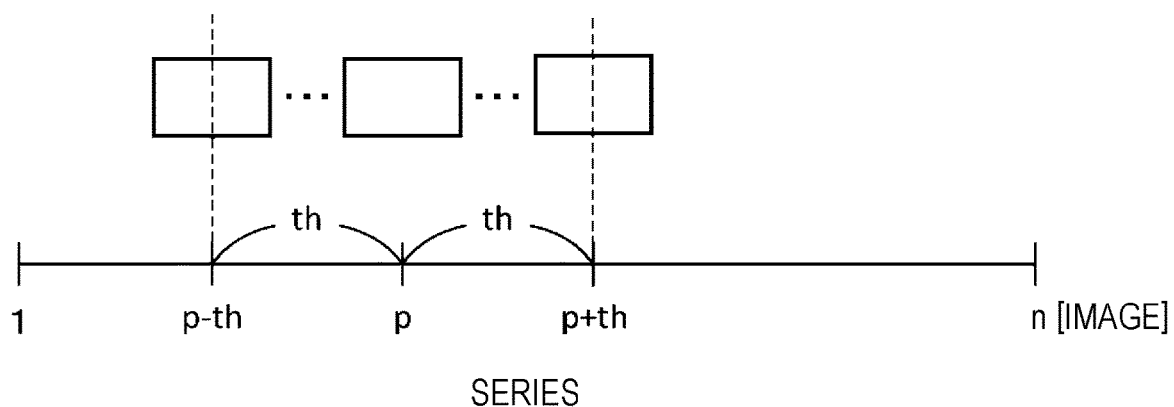
FIG. 54 is a conceptual diagram illustrating a process of acquiring a certain number of adjacent thumbnail images by a summary image generator.

FIG. 54 is a conceptual diagram illustrating a process of acquiring a certain number of adjacent thumbnail images by a summary image generator. In the example of FIG. 54, the slice ID of the thumbnail image selected by the user indicates the pth slice image among all slices constituting the same series. In this case, a preset number (th) of adjacent slice images become the slice images from p−th to p+th. In this case, the summary image generator 112 may specify the slice IDs corresponding to the slice images from p−th to p+th, and transmit a thumbnail image acquisition request to the medical information management system 200. Subsequently, the medical information management system 200 may transmit the thumbnail images from p−th to p+th to the information terminal 100.

In the case of adopting successive frame image generation method 2, the summary images 4910 field may be omitted from the similar case data 4000 illustrated in FIG. 21A, and the burden of creating the similar case data 4000 may be reduced. As a result, the efficiency of the work of creating the similar case data 4000 may be improved, the amount of data of the similar case data 4000 may be increased, and further improvements in radiological interpretation accuracy may be expected.

(Successive Frame Image Generation Method 3)

Successive frame image generation method 3 is a method of generating the successive frame images 717 by using all thumbnail images in a region of the organ where the affected region is included. FIG. 56 is a diagram illustrating a third example of the data structure of localized similar case data 4000. Compared to the similar case data 4000 of FIG. 21A, the similar case data 4000 in FIG. 56 includes intra-organ regions 4920 instead of the summary images 4910.

The intra-organ regions 4920 state per-region ranges of slice IDs in the series to which the relevant similar case data 4000 belongs. In the example of FIG. 56, the intra-organ regions 4920 include "Upper Lobe", "Middle Lobe", and "Lower Lobe" fields. In each of these fields, a range of slice IDs for a particular region (lung field) is stated.

The summary image generator 112 determines, from the slice ID registered in the slice ID 4200 illustrated in FIG. 56 and the ranges of slice IDs registered in the intra-organ regions 4920, which region of the organ is the region to which belongs the slice ID registered in the slice ID 4200. In the example of FIG. 56, "CT149391025" registered in the slice ID 4200 is inside the range "CT149391021-CT149391031". For this reason, the summary image generator 112 determines that this similar case is of the "Middle Lobe".

Subsequently, the summary image generator 112 specifies the slice ID range "CT149391021-CT149391031" registered in "Middle Lobe", and transmits a request to acquire the thumbnail images belonging to this range to the medical information management system 200. The medical information management system 200 receives the thumbnail image acquisition request, and transmits the thumbnail images belonging to the specified slice ID range to the information terminal 100. Subsequently, the summary image generator 112 uses the transmitted thumbnail images to generate the successive frame images 717.

In successive frame image generation method 3, thumbnail images of regions other than the region to which the affected area belongs are not displayed, thereby efficiently contributing to improvement in diagnosis accuracy.

(S5305)

The display controller 104 displays the successive frame images 717 generated in S5304 in the case display area 710, and the process ends. For the display method, as illustrated in FIG. 51, for example, a method of displaying a video of the successive frame images 717 generated in step S5304 in the display area 716a of the thumbnail image 716 selected by the user may be adopted. Specifically, the display controller 104 displays the successive frame images 717 as a video by cycling through the thumbnail images constituting the successive frame images 717 in ascending order of slice ID at a fixed frame rate in the display area 716a.

(S5306)

The summary image generator 112 uses the similar case ID 4100 acquired in S5301 and the lesion attribute 4900 acquired in S5302 to generate representative images 718, and proceeds to S5307.

(Representative Image Generation Method 1)

Representative image generation method 1 is a method of generating the representative images 718 by using the slice IDs registered in the summary images 4910 of the similar case data 4000. In this case, it is sufficient to adopt the similar case data 4000 illustrated in FIG. 20 as the similar case data 4000. The summary image generator 112 references the similar case data 4000 corresponding to the similar case ID 4100 acquired in S5301, and acquires the slice IDs registered in the summary images 4910.

In the example of the similar case data 4000 in FIG. 20, the slice IDs of slice images representing the lung fields of the upper lobe, middle lobe, and lower lobe, respectively, are registered in the summary images 4910. Consequently, the summary image generator 112 specifies the three slice IDs registered in the summary images 4910, and transmits a request to acquire thumbnail images to the medical information management system 200. As a result, the summary image generator 112 acquires thumbnail images corresponding to these three slice IDs, and uses the acquired thumbnail images to generate the representative images 718.

Consequently, as illustrated in FIG. 52, three representative images 718 representing each of the lung fields are listed in the case display area 710.

Representative image generation method 1 lists representative images 718 of respective regions inside an organ, and thus is able to omit the display of irrelevant affected regions. As a result, the user is able to grasp easily the relevant region invaded by the lesion when diagnosing a diffuse lesion.

(Representative Image Generation Method 2)

Figure 57:
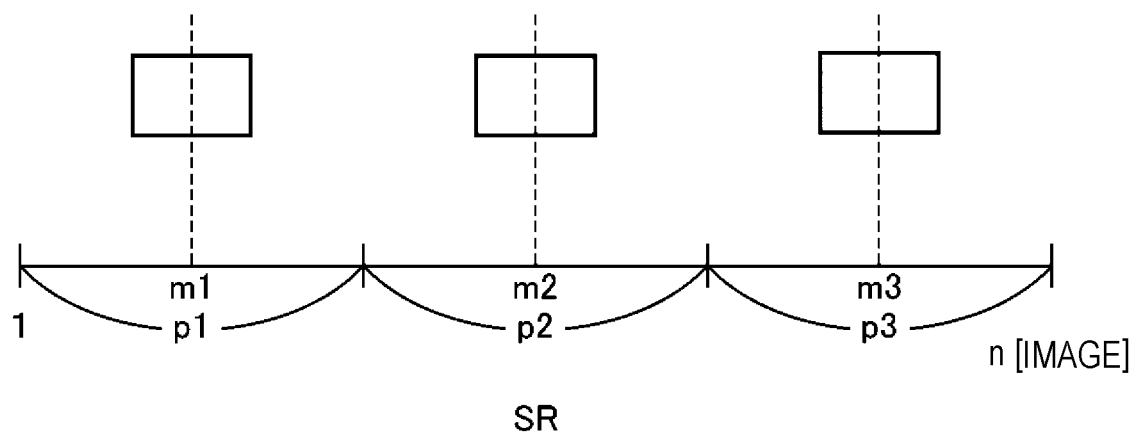
FIG. 57 is a conceptual diagram of a sampling process by a summary image generator.

Representative image generation method 2 is a method of generating the representative images 718 by sampling at a certain interval the series to which belongs the similar case corresponding to the thumbnail image selected by the user. FIG. 57 is a conceptual diagram of a sampling process by the summary image generator 112. In this case, the similar case data 4000 illustrated in FIG. 55 is adopted as the similar case data 4000, for example. FIG. 55 is a diagram illustrating a second example of the data structure of diffuse similar case data 4000.

As illustrated in FIG. 57, the summary image generator 112 divides into three parts a series SR to which belongs the similar case corresponding to the thumbnail image selected by the user. Herein, the summary image generator 112 divides into three parts the series SR by dividing into three parts the slice IDs from the first slice ID "CT149391000" to the last slice ID "CT149391055" registered in the intra-organ regions 4920 of the similar case data 4000 illustrated in FIG. 55.

In the example of FIG. 57, the series SR is divided into regions p1, p2, and p3. Note that the regions p1, p2, and p3 correspond to the upper lobe, the middle lobe, and the lower lobe, respectively. At this point, the summary image generator 112 may divide the series SR into three parts according to a predetermined ratio. The predetermined ratio may be p1:p2:p3=1:1:1, or a ratio accounting for the general size of each region may be adopted.

Next, the summary image generator 112 determines the slice IDs of the respective center positions m1, m2, and m3 of the regions p1, p2, and p3. Subsequently, the summary image generator 112 specifies the three determined slice IDs, and transmits a request to acquire the slice images indicated by these three slice IDs to the medical information management system 200. Consequently, the summary image generator 112 acquires a representative image 718 for each lung field.

With representative image generation method 2, the work of registering representative images illustrating the affected portion of an organ in the similar case data 4000 becomes unnecessary, and the work efficiency when creating the similar case data 4000 may be improved. For this reason, the amount of data of the similar case data 4000 may be increased, and further improvements in radiological interpretation accuracy may be expected.

Note that in the case of adopting representative image generation method 2, the intra-organ regions 4920 may be omitted from the similar case data 4000 illustrated in FIG. 55. In this case, it is sufficient for the summary image generator 112 to specify the slice ID of the similar case data 4000 selected by the user, and transmit a request to acquire a representative image for each lung field to the medical information management system 200. If the slice ID is known, the medical information management system 200 is able to determine the series to which the slice ID belongs by referencing the medical image database 2000 illustrated in FIG. 18A. Thus, after receiving the representative image acquisition request, the medical information management system 200 may use the method illustrated in FIG. 57 discussed earlier to determine a representative image for each lung field, and transmit the determined representative images to the information terminal 100.

(Representative Image Generation Method 3)

Representative image generation method 3 is a method of using the information registered in the intra-organ regions 4920 of the similar case data 4000 illustrated in FIG. 55 to acquire a representative image for each region of a thumbnail image selected by the user. The summary image generator 112 references the similar case data 4000 corresponding to the similar case ID acquired in step S5301, selects one slice ID from the range of slice IDs registered for each region in the intra-organ regions 4920, and thereby acquires the slice IDs of the representative images 718 for each of the regions. In the example of FIG. 55, in the intra-organ regions 4920, "CT149391000-CT149391020" is registered as the range of slice IDs in the upper lobe, "CT149391021-CT149391031" is registered as the range of slice IDs in the middle lobe, and "CT149391032-CT149391055" is registered as the range of slice IDs in the lower lobe. Accordingly, the summary image generator 112 may acquire the slice ID in the center position of each region constituting the intra-organ regions 4920, and acquire thumbnail images of these respective slice IDs from the medical information management system 200.

With representative image generation method 3, representative images 718 for respective regions are displayed, thereby enabling the user to more easily grasp the range of invasion of a lesion, and efficiently contributing to improvement in diagnosis accuracy. Note that in representative image generation method 3, the summary image generator 112 may also determine a certain number of one or more thumbnail images from each region for display as the representative images 718.

(S5307)

The display controller 104 displays the representative images 718 generated in S5306 in the case display area 710, and the process ends. For the display method, it is sufficient to adopt a method of displaying the representative images 718 below the selected thumbnail images, as illustrated in FIG. 52, for example.

As indicated in the process from S5301 to S5307, if the user selects one thumbnail image from the case display area 710, the summary image to present is changed according to whether the selected thumbnail image is a localized lesion or a diffuse lesion. Consequently, even if a very large number of medical images is registered in the medical image database 2000, the present disclosure is able to efficiently present to the physician similar medical images that serve as a reference for diagnosing a medical image to be interpreted. Thus, the present disclosure may contribute to improved diagnosis accuracy.

(Distribution List Selection)

Figure 43:
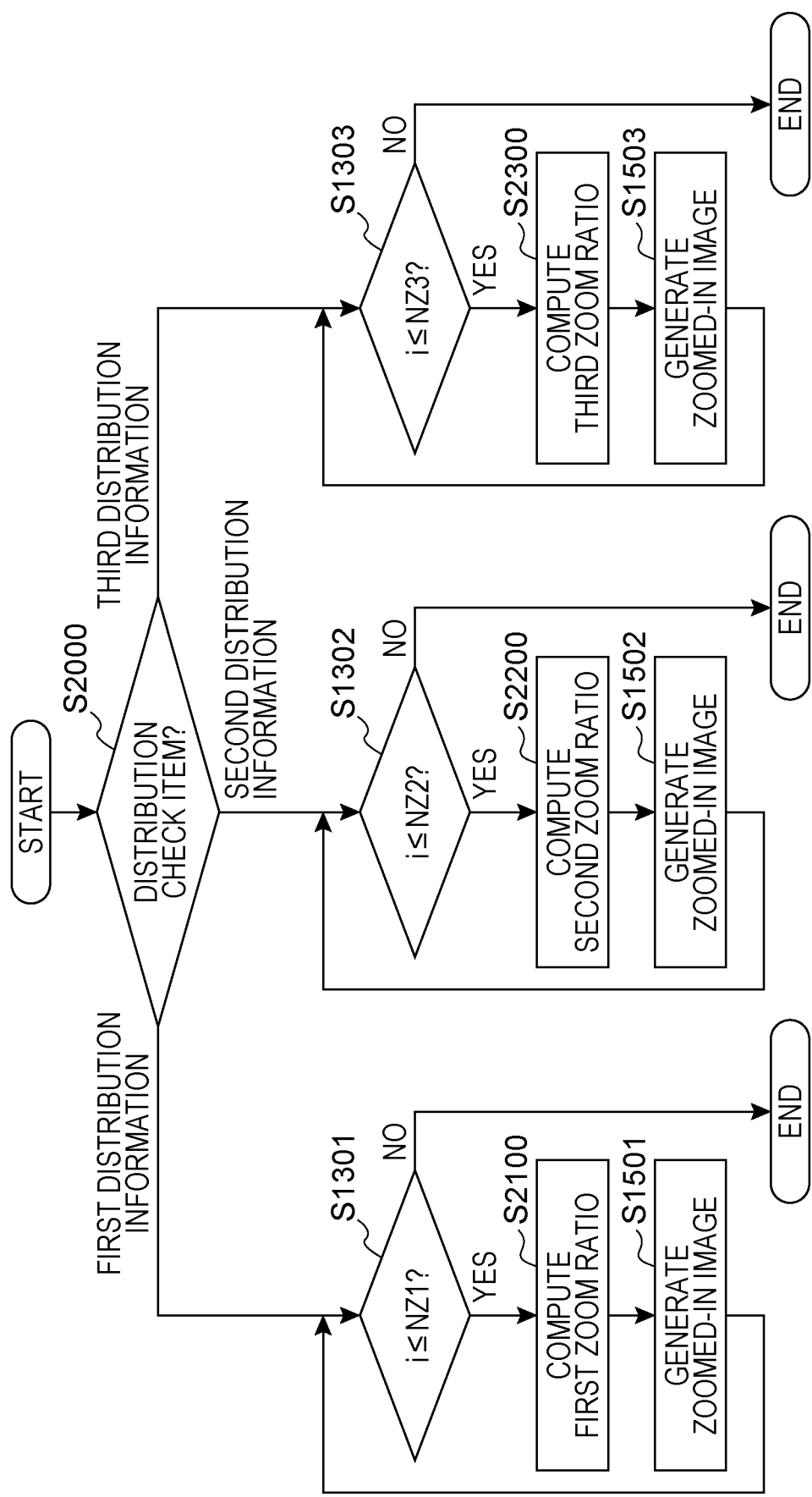
FIG. 43 is a flowchart illustrating a process when a lesion distribution displayed in a distribution list display area is selected.

Next, a process when a lesion distribution displayed in the distribution list display area 750 illustrated in FIG. 11 is selected will be described. FIG. 43 is a flowchart illustrating a process when a lesion distribution displayed in the distribution list display area 750 is selected.

In S2000, if the input controller 103 senses an operation of selecting any one distribution check item from among the lesion distributions (distribution check items) displayed in the distribution list display area 750, the display controller 104 determines whether the sensed distribution check item corresponds to first, second, or third distribution information. In the case of the first distribution information, the process proceeds to S1301, while in the case of the second distribution information, the process proceeds to S1302, and in the case of the third distribution information, the process proceeds to S1303.

The first distribution information is information for selecting, from among the thumbnail images of similar cases listed in the case display area 710, a thumbnail image in which the size of the region of interest belongs to a certain first range indicating a wide range of the lung region. Herein, the first distribution information corresponds to "Bilateral", "Multiple", "Diffuse", and "Hematogenous". Thus, for the first range, a value range is adopted so that the size of the region of interest set when diagnosing these lesion distributions belongs to that value range.

The second distribution information is information for selecting, from among the thumbnail images of similar cases listed in the case display area 710, a thumbnail image in which the size of the region corresponding to the region of interest belongs to a certain second range (lower than the first range; the upper limit value of the second range is less than or equal to the lower limit value of the first range) indicating a part of the lung region. Herein, the second distribution information corresponds to "Bronchial" and "Segmental". Thus, for the second range, a value range is adopted so that the size of the region of interest set when diagnosing these lesion distributions belongs to that value range.

The third distribution information is information for selecting, from among the thumbnail images of similar cases listed in the case display area 710, a thumbnail image in which the region of interest includes the pleura. Herein, the third distribution information corresponds to "Subpleural".

In S1301, the display controller 104 extracts, in order of highest similarity, a number of similar cases less than or equal to the maximum number of displayable thumbnail images in the case display area 710 (in the present embodiment, 20 cases) from among the similar cases obtained by a similar case search, which are similar cases of the lesion distribution selected by the user as the first distribution information. The display controller 104 sets the number of extracted similar cases as a number NZ1 of similar cases to zoom. Subsequently, the display controller 104 sets the thumbnail image of the extracted similar case i (where i is an integer equal to or greater than 1 that serves as an index specifying an extracted similar case) as the thumbnail image to process. Subsequently, the display controller 104 repeats the processes of S2100 and S1501 until i reaches NZ1. Every time the processes of S2100 and S1501 are executed, the display controller 104 increments i by 1. When i exceeds NZ1 (S1301, No), the process ends.

In S2100, the display controller 104 computes a first zoom ratio corresponding to the first distribution information for the similar case i. Herein, 1.0 is adopted as the first zoom ratio, for example. However, this is merely one example, and a zoom ratio other than 1.0 may also be adopted as the first zoom ratio, insofar as the zoom ratio is a value by which the entirety of the region of interest set when diagnosing a lesion distribution indicated by the first distribution information is contained in the display area.

In S1501, the display controller 104 zooms in the thumbnail image of the similar case i by the first zoom ratio of the similar case i.

Figure 44:
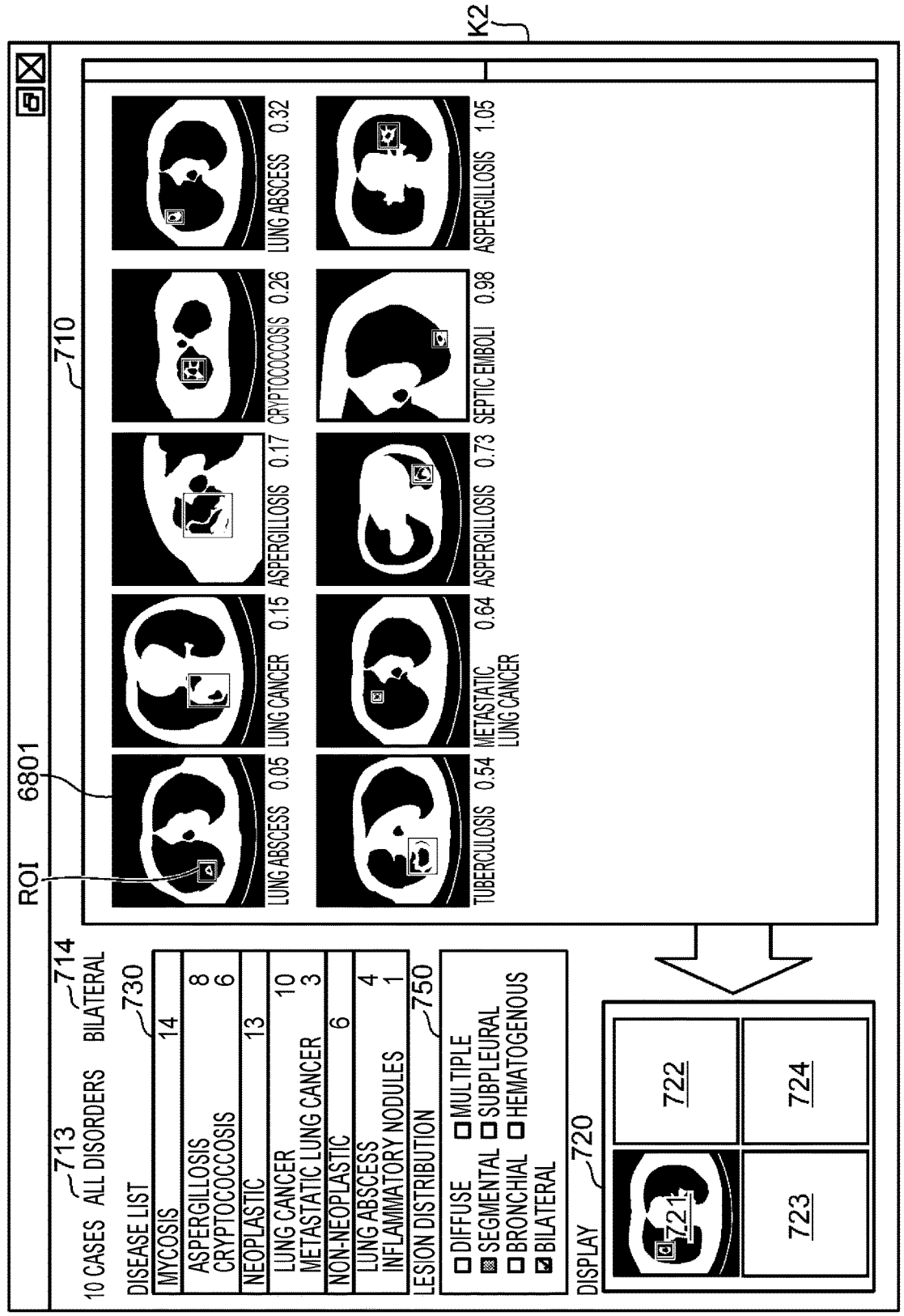
FIG. 44 is a diagram illustrating a basic screen when first distribution information is selected.

FIG. 44 is a diagram illustrating the basic screen K2 when the first distribution information is selected. In FIG. 44, bilateral is selected. In this case, only the thumbnail images of similar cases whose lesion distribution corresponds to bilateral from among the similar cases are displayed in the case display area 710. Also, in this case, since the zoom ratio is 1.0, in the case display area 710, thumbnail images are displayed in the same display mode as the thumbnail images displayed immediately after the similar case search results are obtained. In other words, the display positions of the thumbnail images are not adjusted so that the center of the region of interest ROI is positioned in the center of the display area 6801, and the thumbnail images are also displayed without being zoomed in.

In S1302, the display controller 104 extracts, in order of highest similarity, a number of similar cases less than or equal to the maximum number of displayable thumbnail images in the case display area 710 from among the similar cases obtained by a similar case search, which are similar cases of the lesion distribution selected by the user as the second distribution information. The display controller 104 determines the number of extracted similar cases as a number NZ2 of similar cases to zoom. Subsequently, the display controller 104 sets the thumbnail image of the extracted similar case i as the thumbnail image to process. Subsequently, the display controller 104 repeats the processes of S2200 and S1502 until i reaches NZ2. Every time the processes of S2200 and S1502 are executed, the display controller 104 increments i by 1. When i exceeds NZ2 (S1302, No), the process ends.

In S2200, the display controller 104 uses the predetermined size of the display area for one thumbnail image in the case display area 710 and the region of interest information for the similar case i to compute a second zoom ratio corresponding to the second distribution information for the similar case i.

When the second distribution information is selected, the similar case i is zoomed in so that the size of the region of interest is approximately ½ the size of the display area. For this reason, the display controller 104 calculates a second zoom ratio ki for the similar case i according to the following formula. Provided that Sd is the surface area of the display area, and Si is the surface area of the region of interest in the thumbnail image of the similar case i to be zoomed in, the second zoom ratio ki may be computed as follows.

$$ki = \tfrac{1}{2}(Sd/Si)$$

In S1502, the display controller 104 zooms in the thumbnail image of the similar case i by the second zoom ratio ki, and displays the thumbnail image in the case display area 710 so that the center of the region of interest in the thumbnail image is positioned in the center of the display area.

Figure 45:
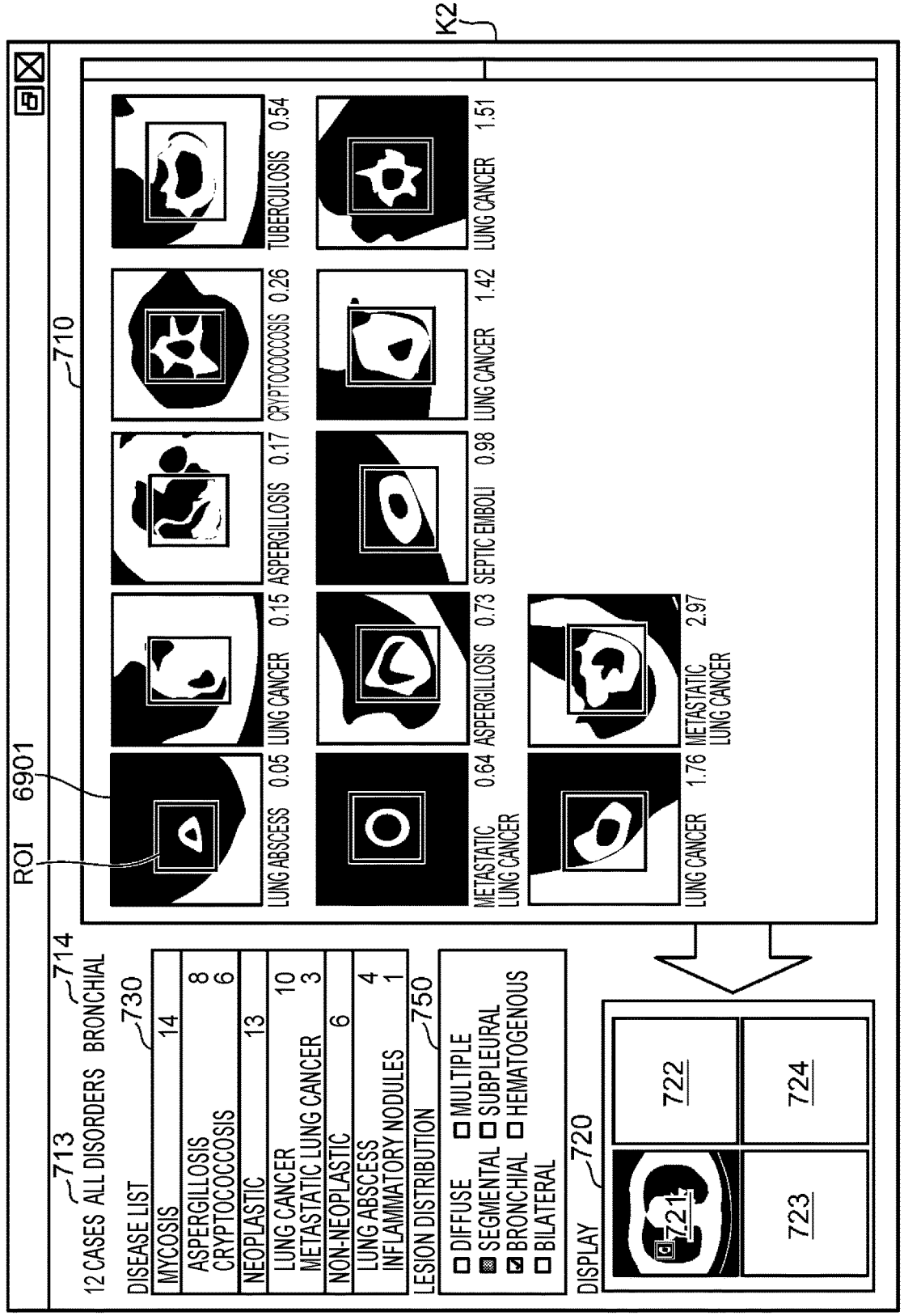
FIG. 45 is a diagram illustrating a basic screen when second distribution information is selected.

FIG. 45 is a diagram illustrating the basic screen K2 when the second distribution information is selected. In FIG. 45, bronchial is selected. In this case, only the thumbnail images of similar cases whose lesion distribution corresponds to bronchial from among the similar cases are displayed in the case display area 710. Also, in the case display area 710, all thumbnail images are zoomed in by the second zoom ratio so that the center of the region of interest ROI is positioned in the center of the display area 6901.

In S1303, the display controller 104 extracts, in order of highest similarity, a number of similar cases less than or equal to the maximum number of displayable thumbnail images in the case display area 710 from among the similar cases obtained by a similar case search, which are similar cases of the lesion distribution selected by the user as the third distribution information. The display controller 104 determines the number of extracted similar cases as a number NZ3 of similar cases to zoom. Subsequently, the display controller 104 sets the thumbnail image of the extracted similar case i as the thumbnail image to process. Subsequently, the display controller 104 repeats the processes of S2300 and S1503 until i reaches NZ3. Every time the processes of S2300 and S1503 are executed, the display controller 104 increments i by 1. When i exceeds NZ3 (S1303, No), the process ends.

In S2300, the display controller 104 uses the predetermined size of the display area for one thumbnail image in the case display area 710, the region of interest information for the similar case i, and pleural region information 4930 to compute a third zoom ratio corresponding to the third distribution information for the similar case i.

FIG. 48 is a diagram illustrating a data structure of similar case data 4000 with added pleural region information 4930. The similar case data 4000 illustrated in FIG. 48 is the similar case data 4000 illustrated in FIG. 20 with the addition of pleural region information 4930. The pleural region information 4930 may also be added to the similar case data 4000 illustrated in FIGS. 21A, 21B, 55, and 56.

Note that if the pleural region information 4930 is not registered in the similar case data 4000, the pleural region information 4930 is not obtained. In this case, the display controller 104 may set the third zoom ratio to the same value as the first zoom ratio, namely, 1.0. Herein, the pleural region information 4930 is information indicating the pleural region in a similar case.

In S1503, the display controller 104 zooms in the thumbnail image of the similar case i by the third zoom ratio ki, and displays the thumbnail image in the case display area 710 so that the center of the region of interest in the thumbnail image is positioned in the center of the display area.

Figure 47:
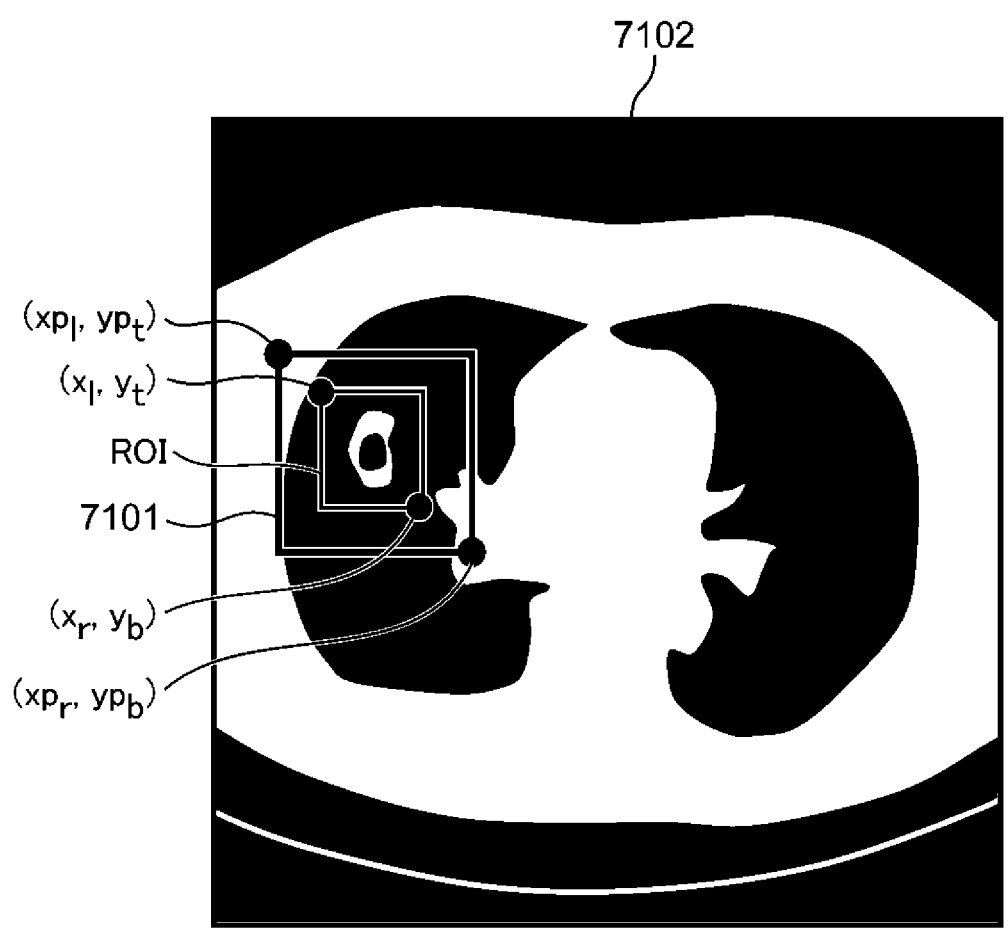
FIG. 47 is a diagram explaining a pleural region.

FIG. 47 is a diagram explaining a pleural region 7101. As illustrated in FIG. 47, the pleural region 7101 is a region including the pleura, and is a rectangular region whose center is positioned at the center of the region of interest ROI, and which is slighter larger in size than the region of interest ROI. Herein, the pleural region information 4930 includes four values: the coordinates of the top-left vertex $(xp_l, yp_t)$, and the coordinates of the bottom-right vertex $(xp_r, yp_b)$ of the pleural region 7101. When the third distribution information is selected, the pleural region is zoomed in, and thus the display controller 104 calculates the third zoom ratio ki according to the following formula. Provided that Sd is the surface area of the display area 7102 and Sp is the surface area of the pleural region 7101, the third zoom ratio ki may be computed as follows.

$$ki=Sd/Sp$$

Note that the pleural region information 4930 may also be input by the user together with the region of interest information when creating the similar case data 4000. Alternatively, the pleural region information 4930 may be created automatically by having an image processing device automatically extract the lung region from a slice image and determine the pleural position.

Figure 46:
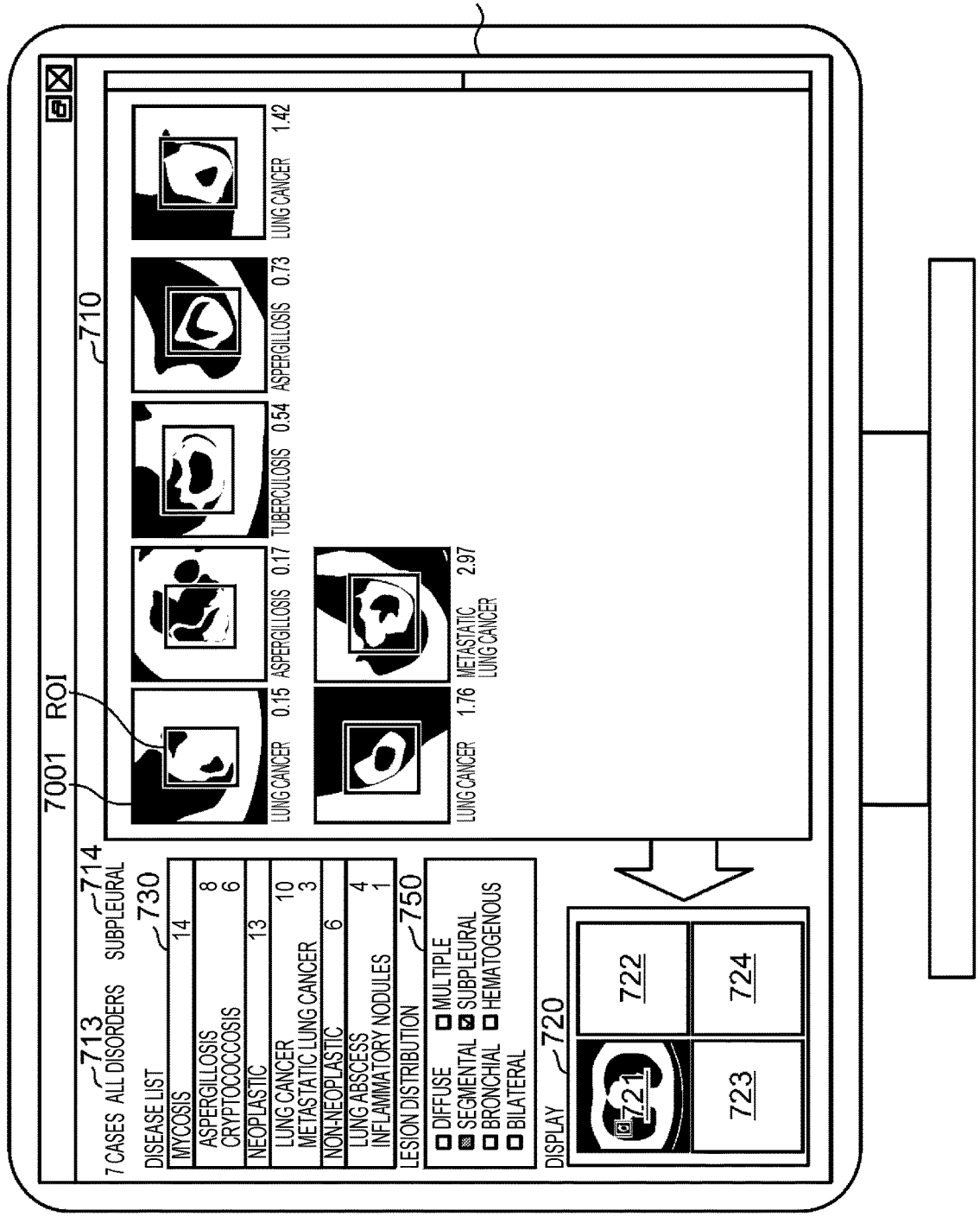
FIG. 46 is a diagram illustrating a basic screen when third distribution information is selected.

FIG. 46 is a diagram illustrating the basic screen K2 when the third distribution information is selected. In FIG. 46, subpleural is selected. In this case, only the thumbnail images of similar cases whose lesion distribution corresponds to subpleural from among the similar cases are displayed in the case display area 710. Also, in the case display area 710, all thumbnail images are zoomed in by the third zoom ratio so that the center of the region of interest ROI is positioned in the center of the display area 7001.

According to the above process, in the case display area 710, thumbnail images are displayed at a zoom ratio reflecting the diagnosis details related to the lesion distribution. Additionally, in the case display area 710, thumbnail images are displayed with consistent sizes of the region of interest. For this reason, since similar medical images having small regions of interest are zoomed in, it is possible to prevent situations in which such regions of interest are overlooked, thereby improving diagnosis accuracy. Furthermore, since the zoom process is conducted only on similar cases displayed in the case display area 710, and not on all similar cases obtained as the similar case search results, the load on the system is greatly reduced.

Note that although medical images of the lungs are used primarily in the present embodiment, the present disclosure is not limited thereto, and is also applicable to medical images of other organs, such as the heart, stomach, and pancreas.

Also, in FIG. 51, although the successive frame images 717 are displayed as a video in the display area 716a, the present disclosure is not limited thereto, and the successive frame images 717 may also be displayed as a video in a separately provided display area on the basic screen K2. Additionally, in FIG. 52, although the representative images 718 are displayed overlaid on top of the case display area 710, the representative images 718 may also be displayed in a separate display area on the basic screen K2.

In addition, after the display of the last frame of the successive frame images 717 is finished, the display controller 104 may also return to the first frame and repeatedly display the successive frame images 717 as a looping video.

In addition, if the input controller 103 senses a click on the successive frame images 717 while the successive frame images 717 are being displayed as a video, the display controller 104 may pause the video display at the clicked position, and display the thumbnail image that was being displayed at the time of the click as a still image. Consequently, the user is able to pause and view a still image of a thumbnail image the user wants to observe thoroughly from among the thumbnail images constituting the successive frame images 717.

The present disclosure may be utilized in devices such as a similar case search device that presents similar cases that serve as a reference when making a diagnosis using a medical image to be interpreted, as well as a radiological interpretation educational device for medical trainees studying radiological interpretation.

What is claimed is:

1. A control method for an information terminal, the control method being executed by a computer of the information terminal, and comprising:
  receiving medical case data items for medical cases, the medical case data items including thumbnail images corresponding to medical images for the medical cases, the medical images being determined on the basis of a target medical image that is interpreted;
  displaying a display screen including the thumbnail images on a display;
  detecting a selected thumbnail image from among the thumbnail images; and
  displaying a first thumbnail image, a second thumbnail image, and a third thumbnail image in a first way or a second way, wherein
  the medical case data items, the medical cases, the thumbnail images, and the medical images are in one-to-one relationship,
  the thumbnail images include the first thumbnail image, the second thumbnail image, and the third thumbnail image,
  each of the medical case data items includes first information indicating a corresponding medical image, second information indicating whether the corresponding medical case is diffuse or localized, and third information indicating first medical images for the medical case,
  the corresponding medical image and the first medical images are obtained through one medical examination performed on a subject,
  the corresponding medical image and the first medical images include a first image in a first tomographic plane of the subject, a second image in a second tomographic plane of the subject, and a third image in a third tomographic plane of the subject, the first tomographic plane is closest to a top of a head of the subject among the first tomographic plane, the second tomographic plane, and the third tomographic plane, the third tomographic plane is farthest away from the top among the first tomographic plane, the second tomographic plane, and the third tomographic plane, the first thumbnail image corresponds to the first image, the second thumbnail image corresponds to the second image, and the third thumbnail image corresponds to the third image, if the second information corresponding to the selected thumbnail image indicates that the medical case corresponding to the selected thumbnail image is diffuse, the first thumbnail image, the second thumbnail image, and the third thumbnail image are displayed in the first way, if the second information corresponding to the selected thumbnail image indicates that the medical case corresponding to the selected thumbnail image is localized, the first thumbnail image, the second thumbnail image, and the third thumbnail image are displayed in the second way, the first way is that the first thumbnail image, the second thumbnail image, and the third thumbnail image are displayed at a same time on the display, and the second way is that (i) the second thumbnail image is displayed on the display after the first thumbnail image is displayed on the display and the third thumbnail image is displayed on the display after the second thumbnail image is displayed on the display, or (ii) the second thumbnail image is displayed on the display after the third thumbnail image is displayed on the display and the first thumbnail image is displayed on the display after the second thumbnail image is displayed on the display.

2. A method comprising:

displaying a first image corresponding to a first medical case whose attribute is diffuse and a second image corresponding to a second medical case whose attribute is localized on a display;

detecting a selection of the first image or the second image;

displaying a third image corresponding to an image in a first tomographic plane of a first subject, a fourth image corresponding to an image in a second tomographic plane of the first subject, and a fifth image corresponding to an image in a third tomographic plane of the first subject in a first way after the detection of the first image; and displaying a sixth image corresponding to an image in a fourth tomographic plane of a second subject, a seventh image corresponding to an image in a fifth tomographic plane of the second subject, and an eighth image corresponding to an image in a sixth tomographic plane of the second subject in a second way after the detection of the second image, wherein the third image, the fourth image and the fifth image correspond to the first medical case, wherein the sixth image, the seventh image and the eighth image correspond to the second medical case, wherein the first tomographic plane is closest to a top of a head of the first subject among the first tomographic plane, the second tomographic plane, and the third tomographic plane, wherein the third tomographic plane is farthest away from the top among the first tomographic plane, the second tomographic plane, and the third tomographic plane, wherein the fourth tomographic plane is closest to a top of a head of the second subject among the fourth tomographic plane, the fifth tomographic plane, and the sixth tomographic plane, wherein the sixth tomographic plane is farthest away from the top among the fourth tomographic plane, the fifth tomographic plane, and the sixth tomographic plane, wherein the first way is that the third image, the fourth image, and the fifth image are displayed at a same time on the display, and wherein the second way is that (i) the seventh image is displayed on the display after the sixth image is displayed on the display and the eighth image is displayed on the display after the seventh image is displayed on the display, or (ii) the seventh image is displayed on the display after the eighth image is displayed on the display and the sixth image is displayed on the display after the seventh image is displayed on the display.

3. A method comprising:

displaying a first image corresponding to a first medical case whose attribute is localized on a display;

detecting a selection of the first image; and displaying a second image corresponding to an image in a first tomographic plane of a first subject, a third image corresponding to an image in a second tomographic plane of the first subject, and a fourth image corresponding to an image in a third tomographic plane of the first subject in a first way after the detection of the first image, wherein the second image, the third image and the fourth image correspond to the first medical case, wherein the first tomographic plane is closest to a top of a head of the first subject among the first tomographic plane, the second tomographic plane, and the third tomographic plane, wherein the third tomographic plane is farthest away from the top among the first tomographic plane, the second tomographic plane, and the third tomographic plane, wherein the first way is that (i) the third image is displayed on the display after the second image is displayed on the display and the fourth image is displayed on the display after the third image is displayed on the display, or (ii) the third image is displayed on the display after the fourth image is displayed on the display and the second image is displayed on the display after the third image is displayed on the display.

* * * * *